United States Patent
Feld et al.

(10) Patent No.: US 11,382,966 B2
(45) Date of Patent: Jul. 12, 2022

(54) METHOD FOR DESIGNING RIG-I LIGANDS

(71) Applicant: Rigontec GmbH, Bonn (DE)

(72) Inventors: Micha Feld, Fürstenfeldbruck (DE); Christine Schuberth-Wagner, Fürstenfeldbruck (DE)

(73) Assignee: Rigontec GmbH, Bonn (DE)

( * ) Notice: Subject to any disclaimer, the term of this patent is extended or adjusted under 35 U.S.C. 154(b) by 0 days.

(21) Appl. No.: 16/497,232

(22) PCT Filed: Mar. 23, 2018

(86) PCT No.: PCT/EP2018/057531
§ 371 (c)(1),
(2) Date: Sep. 24, 2019

(87) PCT Pub. No.: WO2018/172546
PCT Pub. Date: Sep. 27, 2018

(65) Prior Publication Data
US 2020/0016253 A1    Jan. 16, 2020

(30) Foreign Application Priority Data

Mar. 24, 2017 (EP) .................... 17162698
Apr. 12, 2017 (EP) .................... 17166320

(51) Int. Cl.
| A61K 39/00 | (2006.01) |
| A61K 31/713 | (2006.01) |
| A61K 39/12 | (2006.01) |
| A61K 39/39 | (2006.01) |
| C07H 21/04 | (2006.01) |

(52) U.S. Cl.
CPC .... *A61K 39/001102* (2018.08); *A61K 31/713* (2013.01); *A61K 39/12* (2013.01); *A61K 39/39* (2013.01); *A61K 2039/6075* (2013.01); *A61K 2039/804* (2018.08); *A61K 2039/812* (2018.08); *A61K 2039/844* (2018.08); *A61K 2039/884* (2018.08)

(58) Field of Classification Search
None
See application file for complete search history.

(56) References Cited

FOREIGN PATENT DOCUMENTS

| WO | 2008/017473 A2 | 2/2008 |
| WO | 2009/060281 A3 | 5/2009 |
| WO | 2009/141146 A1 | 11/2009 |
| WO | 2010/115202 A2 | 10/2010 |
| WO | 2012/039602 A1 | 3/2012 |
| WO | 2012/130886 A1 | 10/2012 |
| WO | 2014/049079 A1 | 4/2014 |
| WO | 2017/173427 A1 | 10/2017 |

OTHER PUBLICATIONS

Ablasser et al., "Selection of Molecular Structure and Delivery of RNA Oligonucleotides to Activate TLR7 versus TLR8 and to Induce High Amounts of IL-12p70 in Primary Human Monocytes," *J. Immunol.*, 182(11): 6824-6833 (Jun. 1, 2009).

Amparo-Hagmann et al., "RIG-I Detects Triphosphorylated RNA of Listeria monocytogenes during Infection in Non-Immune Cells," *PLoS One*, 8(4): e62872 (Apr. 20, 2013).

Besch et al., "Bifunctional siRNAs for Tumor Therapy," *Methods in Molecular Biology* (Methods and Protocols), 1169: 181-192 (May 31, 2014).

Brunner et al., "Cell-Penetrating and Neurotargeting Dendritic siRNA Nanostructures," *Angew. Chem. Int. Ed. Engl.*, 54(6): 1946-1949 (2015).

Buers et al., "Novel interferonopathies associated with mutations in RIG-I like Receptors," *Cyt Grow Fac Rev.*, 29: 101-107 (Mar. 11, 2016).

Devarkar et al., "Structural basis for m7G recognition and 2'-O-methyl discrimination in capped RNAs by the innate immune receptor RIG-I," *PNAS*, 113(3): 596-601 (Jan. 19, 2016).

Duewell et al., "RIG-I-like helicases induce immunogenic cell death of pancreatic cancer cells and sensitize tumors toward killing by CD8 $^+$T cells," *Cell Death Differ.*, 21 (12): 1825-1837 (Jul. 11, 2014).

Ebert et al., "5' Triphosphorylated Small Interfering RNAs Control Replication of Hepatitis B Virus and Induce an Interferon Response in Human Liver Cells and Mice," *Gastroenterology*, 141(2): 696-706 (May 2, 2011).

Ellermeier et al., "Therapeutic Efficacy of Bifunctional siRNA Combining TGF-β1 Silencing with RIG-I Activation in Pancreatic Cancer," *Cancer Research*, 73(6): 1709-1720 (Mar. 15, 2013).

Gold et al., "Human Growth FactorCream and Hyaluronic Acid Serum in Conjunction with Micro Laser Peel An Efficient Regimen for Skin Rejuvenation," *J Clin Aesthet Dermatol.*, 3(12): 37-42 (Dec. 2010).

Goubau et al., "Antiviral immunity via RIG-I-mediated recognition of RNA bearing 59-diphosphates," *Nature*, 514: 372-375 (Oct. 16, 2014).

Goulet et al., "Systems Analysis of a RIG-I Agonist Inducing Broad Spectrum Inhibition of Virus Infectivity," *PLoS Pathog.*, 9(4): e1003298 (Apr. 25, 2013).

Han et al., "Reversal of Hepatitis B Virus-Induced Immune Tolerance By an Immunostimulatory 3p-HBx-siRNAs in a Retinoic Acid Inducible Gene I—Dependent Manner," *Hepatology*, 54(4): 1179-1189 (Jun. 5, 2011).

Jang et al., "Mutations in DDX58, which Encodes RIG-I, Cause Atypical Singleton-Merten Syndrome," *Am J Hum Genet.*, 96(2): 266-274 (Feb. 5, 2015).

(Continued)

*Primary Examiner* — Kimberly Chong
(74) *Attorney, Agent, or Firm* — Leydig, Voit & Mayer, Ltd.

(57) ABSTRACT

The present invention belongs to the field of biotechnology and pharmaceuticals. The present inventors found a sequence motif for identifying potent RIG-I agonists. Accordingly, the present invention is directed to a method for producing RIG-I agonists, the RIG-I agonists produced by said methods, and uses of said RIG-I agonists, as defined in the claims.

43 Claims, 7 Drawing Sheets

Specification includes a Sequence Listing.

(56) References Cited

OTHER PUBLICATIONS

Junt and Barchet, "Translating nucleic acid-sensing pathways into therapies," *Nat. Rev. Immunol.*, 15(9): 529-544 (Aug. 21, 2015).
Kohlway et al., "Defining the functional determinants for RNA surveillance by RIG-I," *EMBO Rep.*, 14(9): 772-779 (Jul. 30, 2013).
Lin et al., "5'-Triphosphate-Short Interfering RNA: Potent Inhibition of Influenza A Virus Infection by Gene Silencing and RIG-I Activation," *J Virol.*, 86(19): 10359-10369 (Oct. 2012).
Louber et al., "Kinetic discrimination of self/non-self RNA by the ATPase activity of RIG-I and MDA5," *BMC Biol.*, 13: 54 (2015).
Ludwig and Eckstein, "Rapid and Efficient Synthesis of Nucleoside 5'-O-(1-Thiotriphosphates), 5'-Triphosphates and 2',3'-Cyclophosphorothioates Using 2-Chloro-4H-1,3,2-benzodioxaphosphorin-4-one," *J. Org. Chem.*, 54(3): 631-635 (1989).
Martin et al., "Negative impact on clinical outcome of the mutational co-occurrence of SF3B1 and DNMT3A in refractory anemia with ring sideroblasts (RARS)," *Leuk Lymphoma*, 58(7): 1686-1693 (Oct. 24, 2016).
Pasquale et al., "Vaccine Adjuvants: from 1920 to 2015 and Beyond," *Vaccines*, 3: 320-343 (Apr. 16, 2015).
Pichlmair et al. "RIG-I-Mediated Antiviral Responses to Single-Stranded RNA Bearing 5'-Phosphates," *Science*, 314: 997-1001 (Oct. 12, 2006).
Poeck et al., "5'-triphosphate-siRNA: turning gene silencing and Rig-I activation against melanoma," *Nature Medicine*, 14(11): 1256-1262 (Nov. 2008).
Ranoa et al., "Cancer therapies activate RIG-I-like receptor pathway through endogenous non-coding RNAs," *Oncotarget*, 7(18): 26496-26515 (Mar. 28, 2016).
Reikine et al., "Pattern recognition and signaling mechanisms of RIG-I and MDA5," *Front Immunol.*, 5: 324 (Jul. 23, 2014).
Schuberth-Wagner et al., "A Conserved Histidine in the RNA Sensor RIG-I Controls Immune Tolerance to $N_1$-2'O-Methylated Self RNA," *Immunity*, 43(1): 41-51 (Jul. 21, 2015).
Schwarz et al., "Asymmetry in the Assembly of the RNAi Enzyme Complex," *Cell*, 115(2): 199-208 (Oct. 17, 2003).
Van Den Boorn and Hartmann, "Turning Tumors into Vaccines: Co-opting the Innate Immune System," *Immunity*, 39(1): 27-37 (Jul. 25, 2013).
Wu et al., "RIG-I and TLR3 are both required for maximum interferon induction by influenza virus in human lung alveolar epithelial cells," *Virology*, 482: 181-188 (Apr. 11, 2015).
Xue et al., "SRSF1 Facilitates Cytosolic DNA-Induced Production of Type I Interferons Recognized by RIG-I," *PLoS One*, 10(2): e0115354 (Feb. 6, 2015).
Chiang et al., "Sequence-specific modifications enhance the broad-spectrum antiviral response activated by RIG-I agonists," *J. of Virology*, 89(15): 8011-8025 (May 27, 2015).
Lee et al., "Systematic editing of synthetic RIG-I ligands to produce effective antiviral and anti-tumor RNA immunotherapies," *Nucleic Acids Research*, 46(4): 1635-1647 (Feb. 28, 2018).
Schlee, "Master sensors of pathogenic RNA-RIG-I like receptors," *Immunobiology*, 218(11): 1322-1335 (Jul. 1, 2013).
Schlee et al., "Recognition of 5' triphosphate by RIG-I helicase requires short blunt double-stranded RNA as contained in panhandle of negative-strand virus," *Immunity*, 31(1): 25-34 (Jul. 17, 2009).
Wang et al., "Structural and functional insights into 5'-ppp RNA pattern recognition by the innate immune receptor RIG-I," *Nature Structural & Molecular Biology*, 17(7): 781 (Jul. 1, 2010).
European Patent Office, International Search Report in International Patent Application No. PCT/EP2018/057531, 6 pp. (dated May 16, 2018).
European Patent Office, Written Opinion in International Patent Application No. PCT/EP2018/057531, 5 pp. (dated May 16, 2018).
European Patent Office, International Preliminary Report on Patentability in International Patent Application No. PCT/EP2018/057531, 17 pp. (dated Mar. 3, 2019).

RIG-I

TLR7

TLR8

SEQUENCE LISTING

```
<160> NUMBER OF SEQ ID NOS: 120

<210> SEQ ID NO 1
<211> LENGTH: 19
<212> TYPE: RNA
<213> ORGANISM: Artificial Sequence
<220> FEATURE:
<223> OTHER INFORMATION: tail sequence box1 and box2
<220> FEATURE:
<221> NAME/KEY: misc_feature
<222> LOCATION: (2)..(2)
<223> OTHER INFORMATION: n is a, c, g, or u
<220> FEATURE:
<221> NAME/KEY: misc_feature
<222> LOCATION: (4)..(11)
<223> OTHER INFORMATION: n is a, c, g, or u
<220> FEATURE:
<221> NAME/KEY: misc_feature
<222> LOCATION: (13)..(13)
<223> OTHER INFORMATION: n is a, c, g, or u
<220> FEATURE:
<221> NAME/KEY: misc_feature
<222> LOCATION: (15)..(19)
<223> OTHER INFORMATION: n is a, c, g, or u

<400> SEQUENCE: 1
dnwnnnnnnn nunsnnnnn                                              19

<210> SEQ ID NO 2
<211> LENGTH: 19
<212> TYPE: RNA
<213> ORGANISM: Artificial Sequence
<220> FEATURE:
<223> OTHER INFORMATION: consensus tail sequence
<220> FEATURE:
<221> NAME/KEY: misc_feature
<222> LOCATION: (5)..(11)
<223> OTHER INFORMATION: n is a, c, g, or u
<220> FEATURE:
<221> NAME/KEY: misc_feature
<222> LOCATION: (15)..(19)
<223> OTHER INFORMATION: n is a, c, g, or u

<400> SEQUENCE: 2
ugaannnnnn nuucnnnnn                                              19

<210> SEQ ID NO 3
<211> LENGTH: 19
<212> TYPE: RNA
<213> ORGANISM: Artificial Sequence
```

```
<220> FEATURE:
<223> OTHER INFORMATION: consensus tail sequence with 5-mer in
      complementary strand
<220> FEATURE:
<221> NAME/KEY: misc_feature
<222> LOCATION: (5)..(11)
<223> OTHER INFORMATION: n is a, c, g, or u
<220> FEATURE:
<221> NAME/KEY: misc_feature
<222> LOCATION: (15)..(15)
<223> OTHER INFORMATION: n is a, c, g, or u

<400> SEQUENCE: 3 ugaannnnn nuucngavc                                                 19

<210> SEQ ID NO 4
<211> LENGTH: 19
<212> TYPE: RNA
<213> ORGANISM: Artificial Sequence
<220> FEATURE:
<223> OTHER INFORMATION: consensus tail sequence with 5-mer and Box1 in
      complementary strand
<220> FEATURE:
<221> NAME/KEY: misc_feature
<222> LOCATION: (5)..(11)
<223> OTHER INFORMATION: n is a, c, g, or u
<220> FEATURE:
<221> NAME/KEY: misc_feature
<222> LOCATION: (15)..(15)
<223> OTHER INFORMATION: n is a, c, g, or u

<400> SEQUENCE: 4 ugaannnnn nuucngavc                                                 19

<210> SEQ ID NO 5
<211> LENGTH: 19
<212> TYPE: RNA
<213> ORGANISM: Artificial Sequence
<220> FEATURE:
<223> OTHER INFORMATION: consensus tail sequence with 5-mer, Box1, and
      A9 in complementary strand
<220> FEATURE:
<221> NAME/KEY: misc_feature
<222> LOCATION: (5)..(10)
<223> OTHER INFORMATION: n is a, c, g, or u
<220> FEATURE:
<221> NAME/KEY: misc_feature
<222> LOCATION: (15)..(15)
<223> OTHER INFORMATION: n is a, c, g, or u

<400> SEQUENCE: 5 ugaannnnn uuucngavc                                                 19

<210> SEQ ID NO 6
<211> LENGTH: 19
<212> TYPE: RNA
<213> ORGANISM: Artificial Sequence
<220> FEATURE:
<223> OTHER INFORMATION: consensus tail sequence with 5-mer, Box1, A9,
      and Box 2 in complementary strand
<220> FEATURE:
<221> NAME/KEY: misc_feature
<222> LOCATION: (5)..(11)
<223> OTHER INFORMATION: n is a, c, g, or u
<220> FEATURE:
<221> NAME/KEY: misc_feature
<222> LOCATION: (15)..(15)
<223> OTHER INFORMATION: n is a, c, g, or u

<400> SEQUENCE: 6 gaaannnnn nuucngavc                                                 19
```

```
<210> SEQ ID NO 7
<211> LENGTH: 24
<212> TYPE: RNA
<213> ORGANISM: Artificial Sequence
<220> FEATURE:
<223> OTHER INFORMATION: consensus sequence 5-mer and tail
<220> FEATURE:
<221> NAME/KEY: misc_feature
<222> LOCATION: (5)..(5)
<223> OTHER INFORMATION: n is a, c, g, or u
<220> FEATURE:
<221> NAME/KEY: misc_feature
<222> LOCATION: (10)..(16)
<223> OTHER INFORMATION: n is a, c, g, or u
<220> FEATURE:
<221> NAME/KEY: misc_feature
<222> LOCATION: (20)..(24)
<223> OTHER INFORMATION: n is a, c, g, or u

<400> SEQUENCE: 7
gbucnugaan nnnnnnuucn nnnn                                              24

<210> SEQ ID NO 8
<211> LENGTH: 24
<212> TYPE: RNA
<213> ORGANISM: Artificial Sequence
<220> FEATURE:
<223> OTHER INFORMATION: consensus 5-mer and tail sequence with
      consensus 5-mer in complementary strand
<220> FEATURE:
<221> NAME/KEY: misc_feature
<222> LOCATION: (5)..(5)
<223> OTHER INFORMATION: n is a, c, g, or u
<220> FEATURE:
<221> NAME/KEY: misc_feature
<222> LOCATION: (10)..(16)
<223> OTHER INFORMATION: n is a, c, g, or u
<220> FEATURE:
<221> NAME/KEY: misc_feature
<222> LOCATION: (20)..(20)
<223> OTHER INFORMATION: n is a, c, g, or u

<400> SEQUENCE: 8
gbucnugaan nnnnnnuucn gavc                                              24

<210> SEQ ID NO 9
<211> LENGTH: 24
<212> TYPE: RNA
<213> ORGANISM: Artificial Sequence
<220> FEATURE:
<223> OTHER INFORMATION: consensus sequence of 5-mer and tail, and 5-mer
      and Box1 in complementary strand
<220> FEATURE:
<221> NAME/KEY: misc_feature
<222> LOCATION: (5)..(5)
<223> OTHER INFORMATION: n is a, c, g, or u
<220> FEATURE:
<221> NAME/KEY: misc_feature
<222> LOCATION: (10)..(16)
<223> OTHER INFORMATION: n is a, c, g, or u
<220> FEATURE:
<221> NAME/KEY: misc_feature
<222> LOCATION: (20)..(20)
<223> OTHER INFORMATION: n is a, c, g, or u

<400> SEQUENCE: 9
gbucnugaan nnnnnnuucn gavc                                              24

<210> SEQ ID NO 10
<211> LENGTH: 24
<212> TYPE: RNA
<213> ORGANISM: Artificial Sequence
```

```
<220> FEATURE:
<223> OTHER INFORMATION: consensus sequence of 5-mer and tail, and
      5-mer, Box1 and A9 in complementary strand
<220> FEATURE:
<221> NAME/KEY: misc_feature
<222> LOCATION: (5)..(5)
<223> OTHER INFORMATION: n is a, c, g, or u
<220> FEATURE:
<221> NAME/KEY: misc_feature
<222> LOCATION: (10)..(15)
<223> OTHER INFORMATION: n is a, c, g, or u
<220> FEATURE:
<221> NAME/KEY: misc_feature
<222> LOCATION: (20)..(20)
<223> OTHER INFORMATION: n is a, c, g, or u

<400> SEQUENCE: 10
gbucnugaan nnnnnuuucn gavc                                          24

<210> SEQ ID NO 11
<211> LENGTH: 24
<212> TYPE: RNA
<213> ORGANISM: Artificial Sequence
<220> FEATURE:
<223> OTHER INFORMATION: consensus sequence of 5-mer and tail with
      5-mer, Box1, A9, and Box2 in complementary strand
<220> FEATURE:
<221> NAME/KEY: misc_feature
<222> LOCATION: (5)..(5)
<223> OTHER INFORMATION: n is a, c, g, or u
<220> FEATURE:
<221> NAME/KEY: misc_feature
<222> LOCATION: (10)..(16)
<223> OTHER INFORMATION: n is a, c, g, or u
<220> FEATURE:
<221> NAME/KEY: misc_feature
<222> LOCATION: (20)..(20)
<223> OTHER INFORMATION: n is a, c, g, or u

<400> SEQUENCE: 11
gbucngaaan nnnnnnuucn gavc                                          24

<210> SEQ ID NO 12
<211> LENGTH: 21
<212> TYPE: RNA
<213> ORGANISM: Artificial Sequence
<220> FEATURE:
<223> OTHER INFORMATION: RIG-I agonist
<220> FEATURE:
<221> NAME/KEY: misc_feature
<222> LOCATION: (5)..(5)
<223> OTHER INFORMATION: n is a, c, g, or u
<220> FEATURE:
<221> NAME/KEY: misc_feature
<222> LOCATION: (7)..(7)
<223> OTHER INFORMATION: n is a, c, g, or u
<220> FEATURE:
<221> NAME/KEY: misc_feature
<222> LOCATION: (9)..(16)
<223> OTHER INFORMATION: n is a, c, g, or u
<220> FEATURE:
<221> NAME/KEY: misc_feature
<222> LOCATION: (18)..(18)
<223> OTHER INFORMATION: n is a, c, g, or u
<220> FEATURE:
<221> NAME/KEY: misc_feature
<222> LOCATION: (20)..(21)
<223> OTHER INFORMATION: n is a, c, g, or u

<400> SEQUENCE: 12
gbucndnwnn nnnnnwnsn n                                              21

<210> SEQ ID NO 13
```

```
<211> LENGTH: 21
<212> TYPE: RNA
<213> ORGANISM: Artificial Sequence
<220> FEATURE:
<223> OTHER INFORMATION: RIG-I agonist
<220> FEATURE:
<221> NAME/KEY: misc_feature
<222> LOCATION: (7)..(7)
<223> OTHER INFORMATION: n is a, c, g, or u
<220> FEATURE:
<221> NAME/KEY: misc_feature
<222> LOCATION: (9)..(16)
<223> OTHER INFORMATION: n is a, c, g, or u
<220> FEATURE:
<221> NAME/KEY: misc_feature
<222> LOCATION: (18)..(18)
<223> OTHER INFORMATION: n is a, c, g, or u
<220> FEATURE:
<221> NAME/KEY: misc_feature
<222> LOCATION: (20)..(21)
<223> OTHER INFORMATION: n is a, c, g, or u

<400> SEQUENCE: 13
gucuadnwnn nnnnnnwnsn n                                              21

<210> SEQ ID NO 14
<211> LENGTH: 21
<212> TYPE: RNA
<213> ORGANISM: Artificial Sequence
<220> FEATURE:
<223> OTHER INFORMATION: RIG-I agonist
<220> FEATURE:
<221> NAME/KEY: misc_feature
<222> LOCATION: (7)..(7)
<223> OTHER INFORMATION: n is a, c, g, or u
<220> FEATURE:
<221> NAME/KEY: misc_feature
<222> LOCATION: (9)..(16)
<223> OTHER INFORMATION: n is a, c, g, or u
<220> FEATURE:
<221> NAME/KEY: misc_feature
<222> LOCATION: (18)..(18)
<223> OTHER INFORMATION: n is a, c, g, or u
<220> FEATURE:
<221> NAME/KEY: misc_feature
<222> LOCATION: (20)..(21)
<223> OTHER INFORMATION: n is a, c, g, or u

<400> SEQUENCE: 14
guagudnwnn nnnnnwnsn n                                               21

<210> SEQ ID NO 15
<211> LENGTH: 21
<212> TYPE: RNA
<213> ORGANISM: Artificial Sequence
<220> FEATURE:
<223> OTHER INFORMATION: RIG-I agonist
<220> FEATURE:
<221> NAME/KEY: misc_feature
<222> LOCATION: (7)..(7)
<223> OTHER INFORMATION: n is a, c, g, or u
<220> FEATURE:
<221> NAME/KEY: misc_feature
<222> LOCATION: (9)..(16)
<223> OTHER INFORMATION: n is a, c, g, or u
<220> FEATURE:
<221> NAME/KEY: misc_feature
<222> LOCATION: (18)..(18)
<223> OTHER INFORMATION: n is a, c, g, or u
<220> FEATURE:
<221> NAME/KEY: misc_feature
<222> LOCATION: (20)..(21)
<223> OTHER INFORMATION: n is a, c, g, or u

<400> SEQUENCE: 15
```

```
gguaadnwnn nnnnnwnsn n                                           21
```

<210> SEQ ID NO 16
<211> LENGTH: 21
<212> TYPE: RNA
<213> ORGANISM: Artificial Sequence
<220> FEATURE:
<223> OTHER INFORMATION: RIG-I agonist
<220> FEATURE:
<221> NAME/KEY: misc_feature
<222> LOCATION: (7)..(7)
<223> OTHER INFORMATION: n is a, c, g, or u
<220> FEATURE:
<221> NAME/KEY: misc_feature
<222> LOCATION: (9)..(16)
<223> OTHER INFORMATION: n is a, c, g, or u
<220> FEATURE:
<221> NAME/KEY: misc_feature
<222> LOCATION: (18)..(18)
<223> OTHER INFORMATION: n is a, c, g, or u
<220> FEATURE:
<221> NAME/KEY: misc_feature
<222> LOCATION: (20)..(21)
<223> OTHER INFORMATION: n is a, c, g, or u

<400> SEQUENCE: 16

```
ggcagdnwnn nnnnnwnsn n                                           21
```

<210> SEQ ID NO 17
<211> LENGTH: 21
<212> TYPE: RNA
<213> ORGANISM: Artificial Sequence
<220> FEATURE:
<223> OTHER INFORMATION: RIG-I agonist
<220> FEATURE:
<221> NAME/KEY: misc_feature
<222> LOCATION: (7)..(7)
<223> OTHER INFORMATION: n is a, c, g, or u
<220> FEATURE:
<221> NAME/KEY: misc_feature
<222> LOCATION: (9)..(16)
<223> OTHER INFORMATION: n is a, c, g, or u
<220> FEATURE:
<221> NAME/KEY: misc_feature
<222> LOCATION: (18)..(18)
<223> OTHER INFORMATION: n is a, c, g, or u
<220> FEATURE:
<221> NAME/KEY: misc_feature
<222> LOCATION: (20)..(21)
<223> OTHER INFORMATION: n is a, c, g, or u

<400> SEQUENCE: 17

```
gcuucdnwnn nnnnnwnsn n                                           21
```

<210> SEQ ID NO 18
<211> LENGTH: 21
<212> TYPE: RNA
<213> ORGANISM: Artificial Sequence
<220> FEATURE:
<223> OTHER INFORMATION: RIG-I agonist
<220> FEATURE:
<221> NAME/KEY: misc_feature
<222> LOCATION: (7)..(7)
<223> OTHER INFORMATION: n is a, c, g, or u
<220> FEATURE:
<221> NAME/KEY: misc_feature
<222> LOCATION: (9)..(16)
<223> OTHER INFORMATION: n is a, c, g, or u
<220> FEATURE:
<221> NAME/KEY: misc_feature
<222> LOCATION: (18)..(18)
<223> OTHER INFORMATION: n is a, c, g, or u
<220> FEATURE:

```
<221> NAME/KEY: misc_feature
<222> LOCATION: (20)..(21)
<223> OTHER INFORMATION: n is a, c, g, or u

<400> SEQUENCE: 18
gcccadnwnn nnnnnwnsn n                                              21

<210> SEQ ID NO 19
<211> LENGTH: 21
<212> TYPE: RNA
<213> ORGANISM: Artificial Sequence
<220> FEATURE:
<223> OTHER INFORMATION: RIG-I agonist
<220> FEATURE:
<221> NAME/KEY: misc_feature
<222> LOCATION: (7)..(7)
<223> OTHER INFORMATION: n is a, c, g, or u
<220> FEATURE:
<221> NAME/KEY: misc_feature
<222> LOCATION: (9)..(16)
<223> OTHER INFORMATION: n is a, c, g, or u
<220> FEATURE:
<221> NAME/KEY: misc_feature
<222> LOCATION: (18)..(18)
<223> OTHER INFORMATION: n is a, c, g, or u
<220> FEATURE:
<221> NAME/KEY: misc_feature
<222> LOCATION: (20)..(21)
<223> OTHER INFORMATION: n is a, c, g, or u

<400> SEQUENCE: 19
gcgcudnwnn nnnnnwnsn n                                              21

<210> SEQ ID NO 20
<211> LENGTH: 21
<212> TYPE: RNA
<213> ORGANISM: Artificial Sequence
<220> FEATURE:
<223> OTHER INFORMATION: RIG-I agonist
<220> FEATURE:
<221> NAME/KEY: misc_feature
<222> LOCATION: (5)..(5)
<223> OTHER INFORMATION: n is a, c, g, or u
<220> FEATURE:
<221> NAME/KEY: misc_feature
<222> LOCATION: (10)..(16)
<223> OTHER INFORMATION: n is a, c, g, or u
<220> FEATURE:
<221> NAME/KEY: misc_feature
<222> LOCATION: (20)..(21)
<223> OTHER INFORMATION: n is a, c, g, or u

<400> SEQUENCE: 20
gbucnugaan nnnnnnuucn n                                             21

<210> SEQ ID NO 21
<211> LENGTH: 21
<212> TYPE: RNA
<213> ORGANISM: Artificial Sequence
<220> FEATURE:
<223> OTHER INFORMATION: RIG-I agonist
<220> FEATURE:
<221> NAME/KEY: misc_feature
<222> LOCATION: (10)..(16)
<223> OTHER INFORMATION: n is a, c, g, or u
<220> FEATURE:
<221> NAME/KEY: misc_feature
<222> LOCATION: (20)..(21)
<223> OTHER INFORMATION: n is a, c, g, or u

<400> SEQUENCE: 21
gucuaugaan nnnnnnuucn n                                             21
```

```
<210> SEQ ID NO 22
<211> LENGTH: 21
<212> TYPE: RNA
<213> ORGANISM: Artificial Sequence
<220> FEATURE:
<223> OTHER INFORMATION: RIG-I agonist
<220> FEATURE:
<221> NAME/KEY: misc_feature
<222> LOCATION: (10)..(16)
<223> OTHER INFORMATION: n is a, c, g, or u
<220> FEATURE:
<221> NAME/KEY: misc_feature
<222> LOCATION: (20)..(21)
<223> OTHER INFORMATION: n is a, c, g, or u

<400> SEQUENCE: 22
guaguugaan nnnnnnuucn n                                              21

<210> SEQ ID NO 23
<211> LENGTH: 21
<212> TYPE: RNA
<213> ORGANISM: Artificial Sequence
<220> FEATURE:
<223> OTHER INFORMATION: RIG-I agonist
<220> FEATURE:
<221> NAME/KEY: misc_feature
<222> LOCATION: (10)..(16)
<223> OTHER INFORMATION: n is a, c, g, or u
<220> FEATURE:
<221> NAME/KEY: misc_feature
<222> LOCATION: (20)..(21)
<223> OTHER INFORMATION: n is a, c, g, or u

<400> SEQUENCE: 23
gguaaugaan nnnnnnuucn n                                              21

<210> SEQ ID NO 24
<211> LENGTH: 21
<212> TYPE: RNA
<213> ORGANISM: Artificial Sequence
<220> FEATURE:
<223> OTHER INFORMATION: RIG-I agonist
<220> FEATURE:
<221> NAME/KEY: misc_feature
<222> LOCATION: (10)..(16)
<223> OTHER INFORMATION: n is a, c, g, or u
<220> FEATURE:
<221> NAME/KEY: misc_feature
<222> LOCATION: (20)..(21)
<223> OTHER INFORMATION: n is a, c, g, or u

<400> SEQUENCE: 24
ggcagugaan nnnnnnuucn n                                              21

<210> SEQ ID NO 25
<211> LENGTH: 21
<212> TYPE: RNA
<213> ORGANISM: Artificial Sequence
<220> FEATURE:
<223> OTHER INFORMATION: RIG-I agonist
<220> FEATURE:
<221> NAME/KEY: misc_feature
<222> LOCATION: (10)..(16)
<223> OTHER INFORMATION: n is a, c, g, or u
<220> FEATURE:
<221> NAME/KEY: misc_feature
<222> LOCATION: (20)..(21)
<223> OTHER INFORMATION: n is a, c, g, or u

<400> SEQUENCE: 25
```

```
gcuucugaan nnnnnnuucn n                                    21
```

<210> SEQ ID NO 26
<211> LENGTH: 21
<212> TYPE: RNA
<213> ORGANISM: Artificial Sequence
<220> FEATURE:
<223> OTHER INFORMATION: RIG-I agonist
<220> FEATURE:
<221> NAME/KEY: misc_feature
<222> LOCATION: (10)..(16)
<223> OTHER INFORMATION: n is a, c, g, or u
<220> FEATURE:
<221> NAME/KEY: misc_feature
<222> LOCATION: (20)..(21)
<223> OTHER INFORMATION: n is a, c, g, or u

<400> SEQUENCE: 26

```
gcccaugaan nnnnnnuucn n                                    21
```

<210> SEQ ID NO 27
<211> LENGTH: 21
<212> TYPE: RNA
<213> ORGANISM: Artificial Sequence
<220> FEATURE:
<223> OTHER INFORMATION: RIG-I agonist
<220> FEATURE:
<221> NAME/KEY: misc_feature
<222> LOCATION: (10)..(16)
<223> OTHER INFORMATION: n is a, c, g, or u
<220> FEATURE:
<221> NAME/KEY: misc_feature
<222> LOCATION: (20)..(21)
<223> OTHER INFORMATION: n is a, c, g, or u

<400> SEQUENCE: 27

```
gcgcuugaan nnnnnnuucn n                                    21
```

<210> SEQ ID NO 28
<211> LENGTH: 19
<212> TYPE: RNA
<213> ORGANISM: Artificial Sequence
<220> FEATURE:
<223> OTHER INFORMATION: random tail

<400> SEQUENCE: 28

```
uggaugguug gcuaggaua                                       19
```

<210> SEQ ID NO 29
<211> LENGTH: 19
<212> TYPE: RNA
<213> ORGANISM: Artificial Sequence
<220> FEATURE:
<223> OTHER INFORMATION: GFP-2 tail

<400> SEQUENCE: 29

```
ugacccugaa guucaucuu                                       19
```

<210> SEQ ID NO 30
<211> LENGTH: 20
<212> TYPE: DNA
<213> ORGANISM: Artificial Sequence
<220> FEATURE:
<223> OTHER INFORMATION: Primer HPV16E7 forward

<400> SEQUENCE: 30

```
agtgtgactc tacgcttcgg                                      20
```

```
<210> SEQ ID NO 31
<211> LENGTH: 20
<212> TYPE: DNA
<213> ORGANISM: Artificial Sequence
<220> FEATURE:
<223> OTHER INFORMATION: HPV16E7 reverse

<400> SEQUENCE: 31
tgtgcccatt aacaggtctt                                              20

<210> SEQ ID NO 32
<211> LENGTH: 20
<212> TYPE: DNA
<213> ORGANISM: Artificial Sequence
<220> FEATURE:
<223> OTHER INFORMATION: Primer hIFNbeta forward

<400> SEQUENCE: 32
gtcactgtgc ctggaccata                                              20

<210> SEQ ID NO 33
<211> LENGTH: 20
<212> TYPE: DNA
<213> ORGANISM: Artificial Sequence
<220> FEATURE:
<223> OTHER INFORMATION: Primer hIFNbeta reverse

<400> SEQUENCE: 33
agaggcacag gctaggagat                                              20

<210> SEQ ID NO 34
<211> LENGTH: 15
<212> TYPE: DNA
<213> ORGANISM: Artificial Sequence
<220> FEATURE:
<223> OTHER INFORMATION: Primer hbeta-Actin forward

<400> SEQUENCE: 34
gagaccgcgt ccgcc                                                   15

<210> SEQ ID NO 35
<211> LENGTH: 20
<212> TYPE: DNA
<213> ORGANISM: Artificial Sequence
<220> FEATURE:
<223> OTHER INFORMATION: Primer hbeta-Actin reverse

<400> SEQUENCE: 35
atcatccatg gtgagctggc                                              20

<210> SEQ ID NO 36
<211> LENGTH: 19
<212> TYPE: RNA
<213> ORGANISM: Artificial Sequence
<220> FEATURE:
<223> OTHER INFORMATION: independent 19-mer tail sequence

<400> SEQUENCE: 36
ugacccugaa guucaucuu                                               19

<210> SEQ ID NO 37
<211> LENGTH: 18
<212> TYPE: RNA
<213> ORGANISM: Artificial Sequence
<220> FEATURE:
<223> OTHER INFORMATION: independent 19-mer tail sequence
```

```
<400> SEQUENCE: 37
ugacccugaa guucaucu                                              18

<210> SEQ ID NO 38
<211> LENGTH: 19
<212> TYPE: RNA
<213> ORGANISM: Artificial Sequence
<220> FEATURE:
<223> OTHER INFORMATION: independent 19-mer tail sequence

<400> SEQUENCE: 38
ucaaggugaa cuucaagau                                             19

<210> SEQ ID NO 39
<211> LENGTH: 19
<212> TYPE: RNA
<213> ORGANISM: Artificial Sequence
<220> FEATURE:
<223> OTHER INFORMATION: independent 19-mer tail sequence

<400> SEQUENCE: 39
ggcuacgucc aggagcgca                                             19

<210> SEQ ID NO 40
<211> LENGTH: 24
<212> TYPE: RNA
<213> ORGANISM: Artificial Sequence
<220> FEATURE:
<223> OTHER INFORMATION: 121212

<400> SEQUENCE: 40
gacgcugacc cugaaguuca ucuu                                       24

<210> SEQ ID NO 41
<211> LENGTH: 24
<212> TYPE: RNA
<213> ORGANISM: Artificial Sequence
<220> FEATURE:
<223> OTHER INFORMATION: 24R40#5

<400> SEQUENCE: 41
guucuuggau gguuggcuag gaua                                       24

<210> SEQ ID NO 42
<211> LENGTH: 23
<212> TYPE: RNA
<213> ORGANISM: Artificial Sequence
<220> FEATURE:
<223> OTHER INFORMATION: biEGFP1-GUUCU-CDR

<400> SEQUENCE: 42
guucuugacc cugaaguuca ucu                                        23

<210> SEQ ID NO 43
<211> LENGTH: 24
<212> TYPE: RNA
<213> ORGANISM: Artificial Sequence
<220> FEATURE:
<223> OTHER INFORMATION: biEGFP2-GUUCU-CDR

<400> SEQUENCE: 43
guucuucaag gugaacuuca agau                                       24

<210> SEQ ID NO 44
<211> LENGTH: 24
```

```
<212> TYPE: RNA
<213> ORGANISM: Artificial Sequence
<220> FEATURE:
<223> OTHER INFORMATION: 24R60#6

<400> SEQUENCE: 44
gcucuuggau gguuggcuag gaua                                              24

<210> SEQ ID NO 45
<211> LENGTH: 23
<212> TYPE: RNA
<213> ORGANISM: Artificial Sequence
<220> FEATURE:
<223> OTHER INFORMATION: biEGFP1-GCUCU-CDR

<400> SEQUENCE: 45
gcucuugacc cugaaguuca ucu                                               23

<210> SEQ ID NO 46
<211> LENGTH: 24
<212> TYPE: RNA
<213> ORGANISM: Artificial Sequence
<220> FEATURE:
<223> OTHER INFORMATION: biEGFP2-GCUCU-CDR

<400> SEQUENCE: 46
gcucuucaag gugaacuuca agau                                              24

<210> SEQ ID NO 47
<211> LENGTH: 24
<212> TYPE: RNA
<213> ORGANISM: Artificial Sequence
<220> FEATURE:
<223> OTHER INFORMATION: 24R80#1

<400> SEQUENCE: 47
gguccuggau gguuggcuag gaua                                              24

<210> SEQ ID NO 48
<211> LENGTH: 22
<212> TYPE: RNA
<213> ORGANISM: Artificial Sequence
<220> FEATURE:
<223> OTHER INFORMATION: biEGFP1-GGUCC-CDR

<400> SEQUENCE: 48
gguccugacc cugaaguuca uc                                                22

<210> SEQ ID NO 49
<211> LENGTH: 24
<212> TYPE: RNA
<213> ORGANISM: Artificial Sequence
<220> FEATURE:
<223> OTHER INFORMATION: biEGFP2-GGUCC-CDR

<400> SEQUENCE: 49
gguccucaag gugaacuuca agau                                              24

<210> SEQ ID NO 50
<211> LENGTH: 24
<212> TYPE: RNA
<213> ORGANISM: Artificial Sequence
<220> FEATURE:
<223> OTHER INFORMATION: 24R40#14

<400> SEQUENCE: 50
```

```
gacaauggau gguuggcuag gaua                                              24

<210> SEQ ID NO 51
<211> LENGTH: 23
<212> TYPE: RNA
<213> ORGANISM: Artificial Sequence
<220> FEATURE:
<223> OTHER INFORMATION: biEGFP1-GACAA-CDR

<400> SEQUENCE: 51
gacaaugacc cugaaguuca ucu                                               23

<210> SEQ ID NO 52
<211> LENGTH: 24
<212> TYPE: RNA
<213> ORGANISM: Artificial Sequence
<220> FEATURE:
<223> OTHER INFORMATION: biEGFP2-GACAA-CDR

<400> SEQUENCE: 52
gacaaucaag gugaacuuca agau                                              24

<210> SEQ ID NO 53
<211> LENGTH: 24
<212> TYPE: RNA
<213> ORGANISM: Artificial Sequence
<220> FEATURE:
<223> OTHER INFORMATION: 24R60#5

<400> SEQUENCE: 53
gagguuggau gguuggcuag gaua                                              24

<210> SEQ ID NO 54
<211> LENGTH: 23
<212> TYPE: RNA
<213> ORGANISM: Artificial Sequence
<220> FEATURE:
<223> OTHER INFORMATION: biEGFP1-GAGGU-CDR

<400> SEQUENCE: 54
gagguugacc cugaaguuca ucu                                               23

<210> SEQ ID NO 55
<211> LENGTH: 24
<212> TYPE: RNA
<213> ORGANISM: Artificial Sequence
<220> FEATURE:
<223> OTHER INFORMATION: biEGFP2-GAGGU-CDR

<400> SEQUENCE: 55
gagguucaag gugaacuuca agau                                              24

<210> SEQ ID NO 56
<211> LENGTH: 24
<212> TYPE: RNA
<213> ORGANISM: Artificial Sequence
<220> FEATURE:
<223> OTHER INFORMATION: 24R60#11

<400> SEQUENCE: 56
gacgauggau gguuggcuag gaua                                              24

<210> SEQ ID NO 57
<211> LENGTH: 23
<212> TYPE: RNA
<213> ORGANISM: Artificial Sequence
```

```
<220> FEATURE:
<223> OTHER INFORMATION: biEGFP1-GACGA-CDR

<400> SEQUENCE: 57
gacgaugacc cugaaguuca ucu                                              23

<210> SEQ ID NO 58
<211> LENGTH: 24
<212> TYPE: RNA
<213> ORGANISM: Artificial Sequence
<220> FEATURE:
<223> OTHER INFORMATION: biEGFP2-GACGA-CDR

<400> SEQUENCE: 58
gacgaucaag gugaacuuca agau                                             24

<210> SEQ ID NO 59
<211> LENGTH: 24
<212> TYPE: RNA
<213> ORGANISM: Artificial Sequence
<220> FEATURE:
<223> OTHER INFORMATION: biGFP-GUUCU

<400> SEQUENCE: 59
guucuggcua cguccaggag cgca                                             24

<210> SEQ ID NO 60
<211> LENGTH: 24
<212> TYPE: RNA
<213> ORGANISM: Artificial Sequence
<220> FEATURE:
<223> OTHER INFORMATION: biGFP-GAGGU

<400> SEQUENCE: 60
gagguggcua cguccaggag cgca                                             24

<210> SEQ ID NO 61
<211> LENGTH: 24
<212> TYPE: RNA
<213> ORGANISM: Artificial Sequence
<220> FEATURE:
<223> OTHER INFORMATION: biGFP-GACGA

<400> SEQUENCE: 61
gacgaggcua cguccaggag cgca                                             24

<210> SEQ ID NO 62
<211> LENGTH: 24
<212> TYPE: RNA
<213> ORGANISM: Artificial Sequence
<220> FEATURE:
<223> OTHER INFORMATION: biGFP-GGUCC

<400> SEQUENCE: 62
gguccggcua cguccaggag cgca                                             24

<210> SEQ ID NO 63
<211> LENGTH: 24
<212> TYPE: RNA
<213> ORGANISM: Artificial Sequence
<220> FEATURE:
<223> OTHER INFORMATION: biEGFP1-GACAA-CDR

<400> SEQUENCE: 63
gacaaggcua cguccaggag cgca                                             24
```

```
<210> SEQ ID NO 64
<211> LENGTH: 19
<212> TYPE: RNA
<213> ORGANISM: Artificial Sequence
<220> FEATURE:
<223> OTHER INFORMATION: siEGFP#4

<400> SEQUENCE: 64
ucaagauccg ccacaacau                                                       19

<210> SEQ ID NO 65
<211> LENGTH: 19
<212> TYPE: RNA
<213> ORGANISM: Artificial Sequence
<220> FEATURE:
<223> OTHER INFORMATION: siEGFP#5

<400> SEQUENCE: 65
ggcuacgucc aggagcgca                                                       19

<210> SEQ ID NO 66
<211> LENGTH: 21
<212> TYPE: RNA
<213> ORGANISM: Artificial Sequence
<220> FEATURE:
<223> OTHER INFORMATION: 5-mer and tail sequence; Box1 and A9 in
      complementary strand
<220> FEATURE:
<221> NAME/KEY: misc_feature
<222> LOCATION: (5)..(5)
<223> OTHER INFORMATION: n is a, c, g, or u
<220> FEATURE:
<221> NAME/KEY: misc_feature
<222> LOCATION: (11)..(15)
<223> OTHER INFORMATION: n is a, c, g, or u
<220> FEATURE:
<221> NAME/KEY: misc_feature
<222> LOCATION: (20)..(21)
<223> OTHER INFORMATION: n is a, c, g, or u

<400> SEQUENCE: 66
gbucnugaaa nnnnnuuucn n                                                    21

<210> SEQ ID NO 67
<211> LENGTH: 19
<212> TYPE: RNA
<213> ORGANISM: Artificial Sequence
<220> FEATURE:
<223> OTHER INFORMATION: tail sequence; 5-mer, Box1 and Box2 in
      complementary strand
<220> FEATURE:
<221> NAME/KEY: misc_feature
<222> LOCATION: (5)..(10)
<223> OTHER INFORMATION: n is a, c, g, or u
<220> FEATURE:
<221> NAME/KEY: misc_feature
<222> LOCATION: (15)..(15)
<223> OTHER INFORMATION: n is a, c, g, or u

<400> SEQUENCE: 67
gaaannnnnn uucangavc                                                       19

<210> SEQ ID NO 68
<211> LENGTH: 19
<212> TYPE: RNA
<213> ORGANISM: Artificial Sequence
<220> FEATURE:
<223> OTHER INFORMATION: tail sequence; 5-mer, Box1, A9, and Box2 in
      complementary strand
<220> FEATURE:
```

```
<221> NAME/KEY: misc_feature
<222> LOCATION: (5)..(9)
<223> OTHER INFORMATION: n is a, c, g, or u
<220> FEATURE:
<221> NAME/KEY: misc_feature
<222> LOCATION: (15)..(15)
<223> OTHER INFORMATION: n is a, c, g, or u

<400> SEQUENCE: 68
gaaannnnnu uucangavc                                                       19

<210> SEQ ID NO 69
<211> LENGTH: 24
<212> TYPE: RNA
<213> ORGANISM: Artificial Sequence
<220> FEATURE:
<223> OTHER INFORMATION: 5-mer and tailsequence; 5-mer, Box 1, and Box 2
      in complementary strand
<220> FEATURE:
<221> NAME/KEY: misc_feature
<222> LOCATION: (5)..(5)
<223> OTHER INFORMATION: n is a, c, g, or u
<220> FEATURE:
<221> NAME/KEY: misc_feature
<222> LOCATION: (10)..(16)
<223> OTHER INFORMATION: n is a, c, g, or u
<220> FEATURE:
<221> NAME/KEY: misc_feature
<222> LOCATION: (20)..(20)
<223> OTHER INFORMATION: n is a, c, g, or u

<400> SEQUENCE: 69
gbucngaaan nnnnnnuucn gavc                                                 24

<210> SEQ ID NO 70
<211> LENGTH: 24
<212> TYPE: RNA
<213> ORGANISM: Artificial Sequence
<220> FEATURE:
<223> OTHER INFORMATION: 5-mer and tailsequence; 5-mer, Box 1, A9 and
      Box 2 in complementary strand
<220> FEATURE:
<221> NAME/KEY: misc_feature
<222> LOCATION: (5)..(5)
<223> OTHER INFORMATION: n is a, c, g, or u
<220> FEATURE:
<221> NAME/KEY: misc_feature
<222> LOCATION: (10)..(15)
<223> OTHER INFORMATION: n is a, c, g, or u
<220> FEATURE:
<221> NAME/KEY: misc_feature
<222> LOCATION: (20)..(20)
<223> OTHER INFORMATION: n is a, c, g, or u

<400> SEQUENCE: 70
gbucngaaan nnnnnuuucn gavc                                                 24

<210> SEQ ID NO 71
<211> LENGTH: 24
<212> TYPE: RNA
<213> ORGANISM: Artificial Sequence
<220> FEATURE:
<223> OTHER INFORMATION: 121212 with C7G7

<400> SEQUENCE: 71
gacgccgacc cugaaguuca ucuu                                                 24

<210> SEQ ID NO 72
<211> LENGTH: 24
<212> TYPE: RNA
<213> ORGANISM: Artificial Sequence
```

```
<220> FEATURE:
<223> OTHER INFORMATION: 24R60#11.7

<400> SEQUENCE: 72
gacgacgguu uuaguuccaa aagu                                          24

<210> SEQ ID NO 73
<211> LENGTH: 24
<212> TYPE: RNA
<213> ORGANISM: Artificial Sequence
<220> FEATURE:
<223> OTHER INFORMATION: 24R60#5.7

<400> SEQUENCE: 73
gaggucgguu uuaguuccaa aagu                                          24

<210> SEQ ID NO 74
<211> LENGTH: 24
<212> TYPE: RNA
<213> ORGANISM: Artificial Sequence
<220> FEATURE:
<223> OTHER INFORMATION: 24R40#14.7

<400> SEQUENCE: 74
gacaacgguu uuaguuccaa aagu                                          24

<210> SEQ ID NO 75
<211> LENGTH: 24
<212> TYPE: RNA
<213> ORGANISM: Artificial Sequence
<220> FEATURE:
<223> OTHER INFORMATION: 24R60#1.7

<400> SEQUENCE: 75
guggucgguu uuaguuccaa aagu                                          24

<210> SEQ ID NO 76
<211> LENGTH: 24
<212> TYPE: RNA
<213> ORGANISM: Artificial Sequence
<220> FEATURE:
<223> OTHER INFORMATION: 24R60#6.7

<400> SEQUENCE: 76
gcucucgguu uuaguuccaa aagu                                          24

<210> SEQ ID NO 77
<211> LENGTH: 24
<212> TYPE: RNA
<213> ORGANISM: Artificial Sequence
<220> FEATURE:
<223> OTHER INFORMATION: 24R60#11.5

<400> SEQUENCE: 77
gacgagcugu gauuuugga uuug                                           24

<210> SEQ ID NO 78
<211> LENGTH: 24
<212> TYPE: RNA
<213> ORGANISM: Artificial Sequence
<220> FEATURE:
<223> OTHER INFORMATION: 24R60#5.5

<400> SEQUENCE: 78
gaggugcugu gauuuugga uuug                                           24
```

<210> SEQ ID NO 79
<211> LENGTH: 24
<212> TYPE: RNA
<213> ORGANISM: Artificial Sequence
<220> FEATURE:
<223> OTHER INFORMATION: 24R40#14.5

<400> SEQUENCE: 79
gacaagcugu gauuuuugga uuug                                              24

<210> SEQ ID NO 80
<211> LENGTH: 24
<212> TYPE: RNA
<213> ORGANISM: Artificial Sequence
<220> FEATURE:
<223> OTHER INFORMATION: 24R60#1.5

<400> SEQUENCE: 80
guggugcugu gauuuuugga uuug                                              24

<210> SEQ ID NO 81
<211> LENGTH: 24
<212> TYPE: RNA
<213> ORGANISM: Artificial Sequence
<220> FEATURE:
<223> OTHER INFORMATION: 24R60#6.5

<400> SEQUENCE: 81
gcucugcugu gauuuuugga uuug                                              24

<210> SEQ ID NO 82
<211> LENGTH: 24
<212> TYPE: RNA
<213> ORGANISM: Artificial Sequence
<220> FEATURE:
<223> OTHER INFORMATION: 24R60#11.4

<400> SEQUENCE: 82
gacgagcaau cagcuaaacg uuau                                              24

<210> SEQ ID NO 83
<211> LENGTH: 24
<212> TYPE: RNA
<213> ORGANISM: Artificial Sequence
<220> FEATURE:
<223> OTHER INFORMATION: 24R60#5.4

<400> SEQUENCE: 83
gaggugcaau cagcuaaacg uuau                                              24

<210> SEQ ID NO 84
<211> LENGTH: 24
<212> TYPE: RNA
<213> ORGANISM: Artificial Sequence
<220> FEATURE:
<223> OTHER INFORMATION: 24R40#14.4

<400> SEQUENCE: 84
gacaagcaau cagcuaaacg uuau                                              24

<210> SEQ ID NO 85
<211> LENGTH: 24
<212> TYPE: RNA
<213> ORGANISM: Artificial Sequence
<220> FEATURE:
<223> OTHER INFORMATION: 24R60#1.4

```
<400> SEQUENCE: 85
guggugcaau cagcuaaacg uuau                                          24

```
<223> OTHER INFORMATION: biHPV16E7#001-3dAdA (sense)
<220> FEATURE:
<221> NAME/KEY: misc_feature
<222> LOCATION: (25)..(26)
<223> OTHER INFORMATION: desoxy A

<400> SEQUENCE: 91
gguccugacu cuacgcuucg guugaa                                        26

<210> SEQ ID NO 92
<211> LENGTH: 26
<212> TYPE: RNA
<213> ORGANISM: Artificial Sequence
<220> FEATURE:
<223> OTHER INFORMATION: biHPV16E7#001-3dAdA (antisense)
<220> FEATURE:
<221> NAME/KEY: misc_feature
<222> LOCATION: (25)..(26)
<223> OTHER INFORMATION: desoxy A

<400> SEQUENCE: 92
caaccgaagc guagagucag gaccaa                                        26

<210> SEQ ID NO 93
<211> LENGTH: 24
<212> TYPE: RNA
<213> ORGANISM: Artificial Sequence
<220> FEATURE:
<223> OTHER INFORMATION: biHPV16E7#001 (sense)

<400> SEQUENCE: 93
gguccugacu cuacgcuucg guug                                          24

<210> SEQ ID NO 94
<211> LENGTH: 24
<212> TYPE: RNA
<213> ORGANISM: Artificial Sequence
<220> FEATURE:
<223> OTHER INFORMATION: biHPV16E7#001 (antisense)

<400> SEQUENCE: 94
caaccgaagc guagagucag gacc                                          24

<210> SEQ ID NO 95
<211> LENGTH: 21
<212> TYPE: RNA
<213> ORGANISM: Artificial Sequence
<220> FEATURE:
<223> OTHER INFORMATION: RIG-I Agonist
<220> FEATURE:
<221> NAME/KEY: misc_feature
<222> LOCATION: (5)..(5)
<223> OTHER INFORMATION: n is a, c, g, or u
<220> FEATURE:
<221> NAME/KEY: misc_feature
<222> LOCATION: (7)..(7)
<223> OTHER INFORMATION: n is a, c, g, or u
<220> FEATURE:
<221> NAME/KEY: misc_feature
<222> LOCATION: (9)..(16)
<223> OTHER INFORMATION: n is a, c, g, or u
<220> FEATURE:
<221> NAME/KEY: misc_feature
<222> LOCATION: (18)..(18)
<223> OTHER INFORMATION: n is a, c, g, or u
<220> FEATURE:
<221> NAME/KEY: misc_feature
<222> LOCATION: (20)..(21)
<223> OTHER INFORMATION: n is a, c, g, or u

<400> SEQUENCE: 95
```

```
gbucndnwnn nnnnnnunsn n                                             21

<210> SEQ ID NO 96
<211> LENGTH: 21
<212> TYPE: RNA
<213> ORGANISM: Artificial Sequence
<220> FEATURE:
<223> OTHER INFORMATION: RIG-I Agonist
<220> FEATURE:
<221> NAME/KEY: misc_feature
<222> LOCATION: (7)..(7)
<223> OTHER INFORMATION: n is a, c, g, or u
<220> FEATURE:
<221> NAME/KEY: misc_feature
<222> LOCATION: (9)..(16)
<223> OTHER INFORMATION: n is a, c, g, or u
<220> FEATURE:
<221> NAME/KEY: misc_feature
<222> LOCATION: (18)..(18)
<223> OTHER INFORMATION: n is a, c, g, or u
<220> FEATURE:
<221> NAME/KEY: misc_feature
<222> LOCATION: (20)..(21)
<223> OTHER INFORMATION: n is a, c, g, or u

<400> SEQUENCE: 96
gucuadnwnn nnnnnnunsn n                                             21

<210> SEQ ID NO 97
<211> LENGTH: 21
<212> TYPE: RNA
<213> ORGANISM: Artificial Sequence
<220> FEATURE:
<223> OTHER INFORMATION: RIG-I Agonist
<220> FEATURE:
<221> NAME/KEY: misc_feature
<222> LOCATION: (7)..(7)
<223> OTHER INFORMATION: n is a, c, g, or u
<220> FEATURE:
<221> NAME/KEY: misc_feature
<222> LOCATION: (9)..(16)
<223> OTHER INFORMATION: n is a, c, g, or u
<220> FEATURE:
<221> NAME/KEY: misc_feature
<222> LOCATION: (18)..(18)
<223> OTHER INFORMATION: n is a, c, g, or u
<220> FEATURE:
<221> NAME/KEY: misc_feature
<222> LOCATION: (20)..(21)
<223> OTHER INFORMATION: n is a, c, g, or u

<400> SEQUENCE: 97
guagudnwnn nnnnnnunsn n                                             21

<210> SEQ ID NO 98
<211> LENGTH: 21
<212> TYPE: RNA
<213> ORGANISM: Artificial Sequence
<220> FEATURE:
<223> OTHER INFORMATION: RIG-I Agonist
<220> FEATURE:
<221> NAME/KEY: misc_feature
<222> LOCATION: (7)..(7)
<223> OTHER INFORMATION: n is a, c, g, or u
<220> FEATURE:
<221> NAME/KEY: misc_feature
<222> LOCATION: (9)..(16)
<223> OTHER INFORMATION: n is a, c, g, or u
<220> FEATURE:
<221> NAME/KEY: misc_feature
<222> LOCATION: (18)..(18)
<223> OTHER INFORMATION: n is a, c, g, or u
<220> FEATURE:
```

```
<221> NAME/KEY: misc_feature
<222> LOCATION: (20)..(21)
<223> OTHER INFORMATION: n is a, c, g, or u

<400> SEQUENCE: 98
gguaadnwnn nnnnnnunsn n                                              21

<210> SEQ ID NO 99
<211> LENGTH: 21
<212> TYPE: RNA
<213> ORGANISM: Artificial Sequence
<220> FEATURE:
<223> OTHER INFORMATION: RIG-I Agonist
<220> FEATURE:
<221> NAME/KEY: misc_feature
<222> LOCATION: (7)..(7)
<223> OTHER INFORMATION: n is a, c, g, or u
<220> FEATURE:
<221> NAME/KEY: misc_feature
<222> LOCATION: (9)..(16)
<223> OTHER INFORMATION: n is a, c, g, or u
<220> FEATURE:
<221> NAME/KEY: misc_feature
<222> LOCATION: (18)..(18)
<223> OTHER INFORMATION: n is a, c, g, or u
<220> FEATURE:
<221> NAME/KEY: misc_feature
<222> LOCATION: (20)..(21)
<223> OTHER INFORMATION: n is a, c, g, or u

<400> SEQUENCE: 99
ggcagdnwnn nnnnnnunsn n                                              21

<210> SEQ ID NO 100
<211> LENGTH: 21
<212> TYPE: RNA
<213> ORGANISM: Artificial Sequence
<220> FEATURE:
<223> OTHER INFORMATION: RIG-I Agonist
<220> FEATURE:
<221> NAME/KEY: misc_feature
<222> LOCATION: (7)..(7)
<223> OTHER INFORMATION: n is a, c, g, or u
<220> FEATURE:
<221> NAME/KEY: misc_feature
<222> LOCATION: (9)..(16)
<223> OTHER INFORMATION: n is a, c, g, or u
<220> FEATURE:
<221> NAME/KEY: misc_feature
<222> LOCATION: (18)..(18)
<223> OTHER INFORMATION: n is a, c, g, or u
<220> FEATURE:
<221> NAME/KEY: misc_feature
<222> LOCATION: (20)..(21)
<223> OTHER INFORMATION: n is a, c, g, or u

<400> SEQUENCE: 100
gcuucdnwnn nnnnnnunsn n                                              21

<210> SEQ ID NO 101
<211> LENGTH: 21
<212> TYPE: RNA
<213> ORGANISM: Artificial Sequence
<220> FEATURE:
<223> OTHER INFORMATION: RIG-I Agonist
<220> FEATURE:
<221> NAME/KEY: misc_feature
<222> LOCATION: (7)..(7)
<223> OTHER INFORMATION: n is a, c, g, or u
<220> FEATURE:
<221> NAME/KEY: misc_feature
<222> LOCATION: (9)..(16)
<223> OTHER INFORMATION: n is a, c, g, or u
```

```
<220> FEATURE:
<221> NAME/KEY: misc_feature
<222> LOCATION: (18)..(18)
<223> OTHER INFORMATION: n is a, c, g, or u
<220> FEATURE:
<221> NAME/KEY: misc_feature
<222> LOCATION: (20)..(21)
<223> OTHER INFORMATION: n is a, c, g, or u

<400> SEQUENCE: 101
gcccadnwnn nnnnnnunsn n                                        21

<210> SEQ ID NO 102
<211> LENGTH: 21
<212> TYPE: RNA
<213> ORGANISM: Artificial Sequence
<220> FEATURE:
<223> OTHER INFORMATION: RIG-I Agonist
<220> FEATURE:
<221> NAME/KEY: misc_feature
<222> LOCATION: (7)..(7)
<223> OTHER INFORMATION: n is a, c, g, or u
<220> FEATURE:
<221> NAME/KEY: misc_feature
<222> LOCATION: (9)..(16)
<223> OTHER INFORMATION: n is a, c, g, or u
<220> FEATURE:
<221> NAME/KEY: misc_feature
<222> LOCATION: (18)..(18)
<223> OTHER INFORMATION: n is a, c, g, or u
<220> FEATURE:
<221> NAME/KEY: misc_feature
<222> LOCATION: (20)..(21)
<223> OTHER INFORMATION: n is a, c, g, or u

<400> SEQUENCE: 102
gcgcudnwnn nnnnnnunsn n                                        21

<210> SEQ ID NO 103
<211> LENGTH: 24
<212> TYPE: RNA
<213> ORGANISM: Artificial Sequence
<220> FEATURE:
<223> OTHER INFORMATION: RIG-I Agonist sense

<400> SEQUENCE: 103
guucugcaau cagcuaaacg uuau                                     24

<210> SEQ ID NO 104
<211> LENGTH: 24
<212> TYPE: RNA
<213> ORGANISM: Artificial Sequence
<220> FEATURE:
<223> OTHER INFORMATION: RIG-I Agonist sense

<400> SEQUENCE: 104
guucugcaau cagcuauacg uuau                                     24

<210> SEQ ID NO 105
<211> LENGTH: 24
<212> TYPE: RNA
<213> ORGANISM: Artificial Sequence
<220> FEATURE:
<223> OTHER INFORMATION: RIG-I Agonist antisense

<400> SEQUENCE: 105
auaacguuua gcugauugca gaac                                     24

<210> SEQ ID NO 106
```

```
<211> LENGTH: 26
<212> TYPE: RNA
<213> ORGANISM: Artificial Sequence
<220> FEATURE:
<223> OTHER INFORMATION: RIG-I Agonist antisense

<400> SEQUENCE: 106
aaauaacguu uagcugauug cagaac                                              26

<210> SEQ ID NO 107
<211> LENGTH: 24
<212> TYPE: RNA
<213> ORGANISM: Artificial Sequence
<220> FEATURE:
<223> OTHER INFORMATION: RGT522 RGT526 RGT552 RGT555 sense
<220> FEATURE:
<221> NAME/KEY: misc_feature
<222> LOCATION: (1)..(1)
<223> OTHER INFORMATION: 5'-triphosphate
<220> FEATURE:
<221> NAME/KEY: misc_feature
<222> LOCATION: (1)..(3)
<223> OTHER INFORMATION: phosphorothioate linkage between positions 1&2
      and 2&3
<220> FEATURE:
<221> NAME/KEY: misc_feature
<222> LOCATION: (5)..(5)
<223> OTHER INFORMATION: 2'-O-methyl
<220> FEATURE:
<221> NAME/KEY: misc_feature
<222> LOCATION: (9)..(9)
<223> OTHER INFORMATION: 2'-fluoro
<220> FEATURE:
<221> NAME/KEY: misc_feature
<222> LOCATION: (13)..(13)
<223> OTHER INFORMATION: 2'-fluoro
<220> FEATURE:
<221> NAME/KEY: misc_feature
<222> LOCATION: (22)..(24)
<223> OTHER INFORMATION: phosphorothioate linkage between positions
      22&23 and 23&24

<400> SEQUENCE: 107
guucugcaau cagcuaaacg uuau                                                24

<210> SEQ ID NO 108
<211> LENGTH: 24
<212> TYPE: RNA
<213> ORGANISM: Artificial Sequence
<220> FEATURE:
<223> OTHER INFORMATION: RGT568 RGT569 RGT570 RGT571 sense
<220> FEATURE:
<221> NAME/KEY: misc_feature
<222> LOCATION: (1)..(1)
<223> OTHER INFORMATION: 5'-triphosphate
<220> FEATURE:
<221> NAME/KEY: misc_feature
<222> LOCATION: (1)..(3)
<223> OTHER INFORMATION: phosphorothioate linkage between positions 1&2
      and 2&3
<220> FEATURE:
<221> NAME/KEY: misc_feature
<222> LOCATION: (5)..(5)
<223> OTHER INFORMATION: 2'-O-methyl
<220> FEATURE:
<221> NAME/KEY: misc_feature
<222> LOCATION: (9)..(9)
<223> OTHER INFORMATION: 2'-fluoro
<220> FEATURE:
<221> NAME/KEY: misc_feature
<222> LOCATION: (13)..(13)
<223> OTHER INFORMATION: 2'-fluoro
<220> FEATURE:
<221> NAME/KEY: misc_feature
<222> LOCATION: (22)..(24)
```

<223> OTHER INFORMATION: phosphorothioate linkage between positions
      22&23 and 23&24

<400> SEQUENCE: 108
guucugcaau cagcuauacg uuau                                          24

<210> SEQ ID NO 109
<211> LENGTH: 24
<212> TYPE: RNA
<213> ORGANISM: Artificial Sequence
<220> FEATURE:
<223> OTHER INFORMATION: RGT522 RGT568 antisense
<220> FEATURE:
<221> NAME/KEY: misc_feature
<222> LOCATION: (1)..(3)
<223> OTHER INFORMATION: phosphorothioate linkage between positions 1&2
      and 2&3
<220> FEATURE:
<221> NAME/KEY: misc_feature
<222> LOCATION: (3)..(3)
<223> OTHER INFORMATION: 2'-O-methyl
<220> FEATURE:
<221> NAME/KEY: misc_feature
<222> LOCATION: (8)..(8)
<223> OTHER INFORMATION: 2'-fluoro
<220> FEATURE:
<221> NAME/KEY: misc_feature
<222> LOCATION: (12)..(12)
<223> OTHER INFORMATION: 2'-fluoro
<220> FEATURE:
<221> NAME/KEY: misc_feature
<222> LOCATION: (24)..(24)
<223> OTHER INFORMATION: 3'-monophosphate

<400> SEQUENCE: 109
auaacguuua gcugauugca gaac                                          24

<210> SEQ ID NO 110
<211> LENGTH: 24
<212> TYPE: RNA
<213> ORGANISM: Artificial Sequence
<220> FEATURE:
<223> OTHER INFORMATION: RGT526 RGT569 antisense
<220> FEATURE:
<221> NAME/KEY: misc_feature
<222> LOCATION: (1)..(3)
<223> OTHER INFORMATION: phosphorothioate linkage between positions 1&2
      and 2&3
<220> FEATURE:
<221> NAME/KEY: misc_feature
<222> LOCATION: (3)..(3)
<223> OTHER INFORMATION: 2'-O-methyl
<220> FEATURE:
<221> NAME/KEY: misc_feature
<222> LOCATION: (8)..(8)
<223> OTHER INFORMATION: 2'-fluoro
<220> FEATURE:
<221> NAME/KEY: misc_feature
<222> LOCATION: (12)..(12)
<223> OTHER INFORMATION: 2'-fluoro

<400> SEQUENCE: 110
auaacguuua gcugauugca gaac                                          24

<210> SEQ ID NO 111
<211> LENGTH: 26
<212> TYPE: RNA
<213> ORGANISM: Artificial Sequence
<220> FEATURE:
<223> OTHER INFORMATION: RGT552 RGT570 antisense
<220> FEATURE:
<221> NAME/KEY: misc_feature
<222> LOCATION: (3)..(5)

```
<223> OTHER INFORMATION: phosphorothioate linkage between positions 3&4
      and 4&5
<220> FEATURE:
<221> NAME/KEY: misc_feature
<222> LOCATION: (5)..(5)
<223> OTHER INFORMATION: 2'-O-methyl
<220> FEATURE:
<221> NAME/KEY: misc_feature
<222> LOCATION: (10)..(10)
<223> OTHER INFORMATION: 2'-fluoro
<220> FEATURE:
<221> NAME/KEY: misc_feature
<222> LOCATION: (14)..(14)
<223> OTHER INFORMATION: 2'-fluoro
<220> FEATURE:
<221> NAME/KEY: misc_feature
<222> LOCATION: (26)..(26)
<223> OTHER INFORMATION: 3'-monophospahte

<400> SEQUENCE: 111
aaauaacguu uagcugauug cagaac                                          26

<210> SEQ ID NO 112
<211> LENGTH: 26
<212> TYPE: RNA
<213> ORGANISM: Artificial Sequence
<220> FEATURE:
<223> OTHER INFORMATION: RGT555 RGT571 antisense
<220> FEATURE:
<221> NAME/KEY: misc_feature
<222> LOCATION: (3)..(5)
<223> OTHER INFORMATION: phosphorothioate linkage between positions 3&4
      and 4&5
<220> FEATURE:
<221> NAME/KEY: misc_feature
<222> LOCATION: (5)..(5)
<223> OTHER INFORMATION: 2'-O-methyl
<220> FEATURE:
<221> NAME/KEY: misc_feature
<222> LOCATION: (10)..(10)
<223> OTHER INFORMATION: 2'-fluoro
<220> FEATURE:
<221> NAME/KEY: misc_feature
<222> LOCATION: (14)..(14)
<223> OTHER INFORMATION: 2'-fluoro

<400> SEQUENCE: 112
aaauaacguu uagcugauug cagaac                                          26

<210> SEQ ID NO 113
<211> LENGTH: 24
<212> TYPE: RNA
<213> ORGANISM: Artificial Sequence
<220> FEATURE:
<223> OTHER INFORMATION: 3P-GFP2 1S2F sense
<220> FEATURE:
<221> NAME/KEY: misc_feature
<222> LOCATION: (1)..(1)
<223> OTHER INFORMATION: 5'-triphosphate
<220> FEATURE:
<221> NAME/KEY: misc_feature
<222> LOCATION: (7)..(7)
<223> OTHER INFORMATION: 2'-fluoro
<220> FEATURE:
<221> NAME/KEY: misc_feature
<222> LOCATION: (15)..(15)
<223> OTHER INFORMATION: 2'-O-methyl
<220> FEATURE:
<221> NAME/KEY: misc_feature
<222> LOCATION: (22)..(24)
<223> OTHER INFORMATION: phosphorothioate linkage
<220> FEATURE:
<221> NAME/KEY: misc_feature
<222> LOCATION: (23)..(23)
<223> OTHER INFORMATION: 2'-fluoro
```

```
<400> SEQUENCE: 113
gacgcugacc cugaaguuca ucuu                                           24

<210> SEQ ID NO 114
<211> LENGTH: 24
<212> TYPE: RNA
<213> ORGANISM: Artificial Sequence
<220> FEATURE:
<223> OTHER INFORMATION: 3P-GFP2 1S2F antisense
<220> FEATURE:
<221> NAME/KEY: misc_feature
<222> LOCATION: (1)..(3)
<223> OTHER INFORMATION: phosphorothioate linkage
<220> FEATURE:
<221> NAME/KEY: misc_feature
<222> LOCATION: (12)..(12)
<223> OTHER INFORMATION: 2'-fluoro
<220> FEATURE:
<221> NAME/KEY: misc_feature
<222> LOCATION: (22)..(22)
<223> OTHER INFORMATION: 2'-O-methyl

<400> SEQUENCE: 114
aagaugaacu ucaggucag cguc                                            24

<210> SEQ ID NO 115
<211> LENGTH: 24
<212> TYPE: RNA
<213> ORGANISM: Artificial Sequence
<220> FEATURE:
<223> OTHER INFORMATION: RIG-I Agonist antisense

<400> SEQUENCE: 115
auaacguaua gcugauugca gaac                                           24

<210> SEQ ID NO 116
<211> LENGTH: 26
<212> TYPE: RNA
<213> ORGANISM: Artificial Sequence
<220> FEATURE:
<223> OTHER INFORMATION: RIG-I Agonist antisense

<400> SEQUENCE: 116
aaauaacgua uagcugauug cagaac                                         26

<210> SEQ ID NO 117
<211> LENGTH: 24
<212> TYPE: RNA
<213> ORGANISM: Artificial Sequence
<220> FEATURE:
<223> OTHER INFORMATION: RIG-I Agonist antisense
<220> FEATURE:
<221> NAME/KEY: misc_feature
<222> LOCATION: (1)..(3)
<223> OTHER INFORMATION: phosphorothioate linkage between positions 1&2
      and 2&3
<220> FEATURE:
<221> NAME/KEY: misc_feature
<222> LOCATION: (3)..(3)
<223> OTHER INFORMATION: 2'-O-methyl
<220> FEATURE:
<221> NAME/KEY: misc_feature
<222> LOCATION: (8)..(8)
<223> OTHER INFORMATION: 2'-fluoro
<220> FEATURE:
<221> NAME/KEY: misc_feature
<222> LOCATION: (12)..(12)
<223> OTHER INFORMATION: 2'-fluoro
<220> FEATURE:
<221> NAME/KEY: misc_feature
```

<222> LOCATION: (24)..(24)
<223> OTHER INFORMATION: 3'-monophosphate

<400> SEQUENCE: 117
auaacguaua gcugauugca gaac                                               24

<210> SEQ ID NO 118
<211> LENGTH: 24
<212> TYPE: RNA
<213> ORGANISM: Artificial Sequence
<220> FEATURE:
<223> OTHER INFORMATION: RIG-I Agonist antisense
<220> FEATURE:
<221> NAME/KEY: misc_feature
<222> LOCATION: (1)..(3)
<223> OTHER INFORMATION: phosphorothioate linkage between positions 1&2
      and 2&3
<220> FEATURE:
<221> NAME/KEY: misc_feature
<222> LOCATION: (3)..(3)
<223> OTHER INFORMATION: 2'-O-methyl
<220> FEATURE:
<221> NAME/KEY: misc_feature
<222> LOCATION: (8)..(8)
<223> OTHER INFORMATION: 2'-fluoro
<220> FEATURE:
<221> NAME/KEY: misc_feature
<222> LOCATION: (12)..(12)
<223> OTHER INFORMATION: 2'-fluoro

<400> SEQUENCE: 118
auaacguaua gcugauugca gaac                                               24

<210> SEQ ID NO 119
<211> LENGTH: 26
<212> TYPE: RNA
<213> ORGANISM: Artificial Sequence
<220> FEATURE:
<223> OTHER INFORMATION: RIG-I Agonist antisense
<220> FEATURE:
<221> NAME/KEY: misc_feature
<222> LOCATION: (3)..(5)
<223> OTHER INFORMATION: phosphorothioate linkage between positions 3&4
      and 4&5
<220> FEATURE:
<221> NAME/KEY: misc_feature
<222> LOCATION: (5)..(5)
<223> OTHER INFORMATION: 2'-O-methyl
<220> FEATURE:
<221> NAME/KEY: misc_feature
<222> LOCATION: (10)..(10)
<223> OTHER INFORMATION: 2'-fluoro
<220> FEATURE:
<221> NAME/KEY: misc_feature
<222> LOCATION: (14)..(14)
<223> OTHER INFORMATION: 2'-fluoro
<220> FEATURE:
<221> NAME/KEY: misc_feature
<222> LOCATION: (26)..(26)
<223> OTHER INFORMATION: 3'-monophosphate

<400> SEQUENCE: 119
aaauaacgua uagcugauug cagaac                                             26

<210> SEQ ID NO 120
<211> LENGTH: 26
<212> TYPE: RNA
<213> ORGANISM: Artificial Sequence
<220> FEATURE:
<223> OTHER INFORMATION: RIG-I Agonist antisense
<220> FEATURE:
<221> NAME/KEY: misc_feature
<222> LOCATION: (3)..(5)

```
<223> OTHER INFORMATION: phosphorothioate linkage between positions 3&4
      and 4&5
<220> FEATURE:
<221> NAME/KEY: misc_feature
<222> LOCATION: (5)..(5)
<223> OTHER INFORMATION: 2'-O-methyl
<220> FEATURE:
<221> NAME/KEY: misc_feature
<222> LOCATION: (10)..(10)
<223> OTHER INFORMATION: 2'-fluoro
<220> FEATURE:
<221> NAME/KEY: misc_feature
<222> LOCATION: (14)..(14)
<223> OTHER INFORMATION: 2'-fluoro

<400> SEQUENCE: 120
aaauaacgua uagcugauug cagaac                                          26
```

METHOD FOR DESIGNING RIG-I LIGANDS

CROSS-REFERENCE TO RELATED APPLICATIONS

This application is the U.S. national phase of International Application No. PCT/EP2018/057531, filed on Mar. 23, 2018, which designates the United States, and which claims the benefit of European Patent Application No. 17162698.9, filed on Mar. 24, 2017, and European Patent Application No. 17166320.6, filed on Apr. 12, 2017, the contents of each of which are incorporated in their entireties by reference herein.

INCORPORATION BY REFERENCE OF ELECTRONICALLY SUBMITTED MATERIALS

Incorporated by reference in its entirety herein is a computer-readable nucleotide/amino acid sequence listing submitted herewith and identified as follows: 38,047 bytes ASCII (Text) file named "745939_ST25.TXT" created Sep. 19, 2019.

BACKGROUND OF THE INVENTION

The mammalian immune system has evolved a diverse array of pattern recognition receptors (PRRs) to detect invading pathogens and to clear infection (Goulet et al., 2013, PLoS Pathogens). During infection, foreign ribonucleic acids released from bacterial and viral threats are recognized by Toll-like receptors (TLRs) and RIG-I-like helicases (RLRs) (Amparo-Hagmann et al., 2013, PLoS One). The RLR-family comprises three DExD/H box RNA helicases RIG-I, MDA5 and LGP-2 all of which are located to the cytoplasm (Goulet et al., 2013, PLoS Pathogens). Interestingly, RLRs diverge in their pathophysiological action and have been suggested to trigger either anti-(LGP-2) or pro-inflammatory responses (MDA-5 and RIG-I) (Ranoa et al., 2016, Oncotarget). Consistently, gain-of-function mutations of the RIG-I encoding gene DDX58 are associated with rare inherited immune pathologies (Buers et al., 2016, Cyt Grow Fac Rev; Jang et al., 2015, Am J Hum Genetics). Further, DDX58 177 C>T polymorphisms are implicated in the pathogenesis of classical Hodgkin lymphomas (Martin et al., 2016, Leuk Lymphoma).

Classically, RIG-I plays a crucial role in promoting the release of type I and type III interferons to fortify host's anti-viral immunity (Wu et al., 2015, Virology). Moreover, transcriptome analysis reveals a RIG-I-related signature covering the canonical pathway categories "IFN signaling", "activation of IRFs by cytosolic PRRs", "TNFR2 signaling" and "antigen presentation" indicating that RIG-I bridges the innate and adaptive immune system (Goulet et al., 2013, PLoS Pathogens). Intriguingly, RIG-I-induced immunogenic tumor cell death triggers adaptive immunity engaging dendritic cells and T-cells to kill tumors in vivo providing a second innate/adaptive immune system loop (Duewell et al., 2014, Cell death and differentiation). Of note, RIG-I-induced apoptosis is restricted to tumor-cells only (Duewell et al., 2014, Cell death and differentiation).

Recent studies identify key structural features of optimal RIG-I ligands. Short length, double-strandedness, 5'-triphosphorylation and blunt base pairing characterize the prototypic RNA-based RIG-I agonist (Schlee et al., 2009, Immunity; Pichlmair et al., 2006, Science; Schlee, 2013, Immunobiology; WO 2008/017473; WO 2009/141146; WO 2014/049079). Structural and functional analysis of RIG-I reveal that single amino acids and a lysine-rich patch located at the C-terminal domain (CTD) of RIG-I sense the structural properties of RNAs (Wang et al., Nat Struc Mol Biol). Remarkably, typical eukaryotic 2'-O-methylation pattern and 7-methyl guanosine capping of the 5'-triphosphate group of RNAs prevent binding to RIG-I and thus allow distinguishing host from pathogenic non-self RNA. Specifically, modifications at the very 5' end decrease RNA affinity, ATPase activity and production of pro-inflammatory cytokines (Schuberth-Wagner et al., 2016, Immunity; Devarkar et al., 2016, PNAS). It is hypothesized that the ATP turnover kinetics of RIG-I fine-tune self/non-self-discrimination (Louber et al., 2015, BMC Biology). However, recent findings indicate that also endogenous small non-coding RNAs leaking to the cytoplasm can activate RIG-I during ionizing radiation therapy (Ranoa et al., 2016, Oncotarget). In addition, a hetero-trimeric complex of RIG-I/RNA polymerase III/serine-arginine-rich splicing factor 1 facilitates RIG-I activation in response to delocalized, cytosolic DNA via a 5' triphosphorylated RNA intermediate (Ablasser et al., 2009, Nat Immunol; Xue et al., 2015, PLoS One).

Kohlway and colleagues showed the HEL2i domain of RIG-I to slide along the dsRNA recognizing and contacting with the dsRNA at position 5-9 (from the 5' end of the sense strand) (Kohlway et al., 2013, EMBO). Recently, investigations on oligonucleotide sequence modifications demonstrated that nucleotide sequence exchanges can negatively affect stimulatory activity (Chiang et al., 2015, Journal of Virology). Moreover, crystal structural studies demonstrated that specific amino acids of RIG-I sense particular nucleotides and structural conformations of the dsRNA backbone to promote immune activation (Wang et al., 2010, Nat Struc Mol Biol).

The cytosolic PAMP sensor RIG-I detects foreign RNA and mounts an effective anti-pathogenic immune response. The 5'-phosphorylation status, 5'-capping, 5'-blunt end formation and 2% modifications are crucial structural moieties of dsRNA shaping the RIG-I-dependent immune activation. However, decoding of RNA sequence-specific signatures remains largely elusive. Thus the present inventors aimed (i) to evaluate the role of defined 5-mer sequences at the very 5'-end of a RNA, (ii) to dissect the contribution of single nucleotide substitutions on RIG-I activation and (iii) to translate identified functional boxes to novel optimized RIG-I agonists. Screening of different dsRNAs revealed an optimal 5' 5-mer box harboring a $G_1$ N(no A)$_2$ $U_3$ $C_4$ $N_5$ motif (5-mer). Moreover, two additional regulatory boxes at positions 6-8 (box 1) and 17-19 (box 2) (5'-3' direction on the sense strand) were identified. Interestingly, guanosine and cytidine doublets can be detrimental in box 1. Novel optimized, box-based RIG-I ligands showed profound immune activation.

SUMMARY OF THE INVENTION

All sequences provided herein are indicated in accordance with Appendix 2, Table 1 of the WIPO ST.25 standard. Accordingly, a nucleotide "b" means "g or c or u" (i.e. not a), a nucleotide "d" means "a or g or u" (i.e. not c), a nucleotide "w" means "a or u" (i.e. a weak interaction), a nucleotide "s" means "g or c" (i.e. a strong interaction), a nucleotide "v" means "a or g or c" (i.e. not u), and a nucleotide "n" means "a or g or c or u" (i.e. any).

The present inventors found new structural requirements for optimal RIG-I activation. Starting from these new findings, the inventors developed new design rules which allow identifying highly active RIG-I agonists.

Accordingly, the present invention is directed to a method for producing a RIG-I agonist, comprising the steps of
(a) preparing a first polyribonucleotide with 21-300 nucleotides in length, which polyribonucleotide starts at the 5' end with a sequence selected from

```
5'-gbucndnwnnnnnnnnwnsnn-3',    (SEQ ID NO: 12)

5'-gucuadnwnnnnnnnnwnsnn-3',    (SEQ ID NO: 13)

5'-guagudnwnnnnnnnnwnsnn-3',    (SEQ ID NO: 14)

5'-gguaadnwnnnnnnnnwnsnn-3',    (SEQ ID NO: 15)

5'-ggcagdnwnnnnnnnnwnsnn-3',    (SEQ ID NO: 16)

5'-gcuucdnwnnnnnnnnwnsnn-3',    (SEQ ID NO: 17)

5'-gcccadnwnnnnnnnnwnsnn-3',    (SEQ ID NO: 18)
and

5'-gcgcudnwnnnnnnnnwnsnn-3';    (SEQ ID NO: 19)
```

(b) preparing a second polyribonucleotide with 21-300 nucleotides in length which is at least 80% complementary to the first polyribonucleotide of step (a) over the whole length of the first polyribonucleotide of step (a), and which, if annealed to the first polyribonucleotide of step (a), exhibits a 3' overhang of at most 2 nucleotides, or at most 1 nucleotide, or forms a blunt end with the 5' end of the polyribonucleotide of step (a); and
(c) annealing the first polyribonucleotide of step (a) with the second polyribonucleotide of step (b), thereby obtaining a RIG-I agonist.

As noted above, the RIG-I agonists identified and prepared by one of the above methods have high type-I IFN inducing activity. Therefore, RIG-I agonists are also provided which are obtainable by one of the foregoing methods.

Also described is a pharmaceutical composition comprising at least one such RIG-I agonist, and a pharmaceutically acceptable carrier. These pharmaceutical compositions are particular useful in medicine, such as for use in preventing and/or treating a disease or condition selected from a tumor, an infection, and an immune disorder or to be used as or part of a prophylactic regimen, e.g. vaccine adjuvant or immune protective agent.

Alternatively, the RIG-I agonists identified and prepared by one of the above methods are useful as a research tool. Hence, also described is an ex vivo method for inducing type I IFN production in a cell, comprising the step of contacting a cell expressing RIG-I with at least one RIG-I agonist of the present disclosure, optionally in mixture with a complexation agent.

DETAILED DESCRIPTION OF THE INVENTION

Accordingly, the present disclosure provides a method for producing a RIG-I agonist, comprising the steps of
(a) preparing a first polyribonucleotide with 21-300 nucleotides in length, which polyribonucleotide starts at the 5' end with a sequence selected from

```
5'-gbucndnwnnnnnnnnwnsnn-3',    (SEQ ID NO: 12)

5'-gucuadnwnnnnnnnnwnsnn-3',    (SEQ ID NO: 13)

5'-guagudnwnnnnnnnnwnsnn-3',    (SEQ ID NO: 14)

5'-gguaadnwnnnnnnnnwnsnn-3',    (SEQ ID NO: 15)

5'-ggcagdnwnnnnnnnnwnsnn-3',    (SEQ ID NO: 16)

5'-gcuucdnwnnnnnnnnwnsnn-3',    (SEQ ID NO: 17)

5'-gcccadnwnnnnnnnnwnsnn-3',    (SEQ ID NO: 18)
and

5'-gcgcudnwnnnnnnnnwnsnn-3';    (SEQ ID NO: 19)
```

(b) preparing a second polyribonucleotide with 21-300 nucleotides in length which is at least 80% complementary to the first polyribonucleotide of step (a) over the whole length of the first polyribonucleotide of step (a), and which, if annealed to the first polyribonucleotide of step (a), exhibits a 3' overhang of at most 2 nucleotides, or at most 1 nucleotide, or forms a blunt end with the 5' end of the polyribonucleotide of step (a); and
(c) annealing the first polyribonucleotide of step (a) with the second polyribonucleotide of step (b), thereby obtaining a RIG-I agonist.

As shown in FIGS. 3 to 6, there are also certain structural requirements by way of two boxes for the RNA sequence of step (a) (the tail sequence in FIG. 6) in order to obtain optimal IFNα inducing activity. For example, it could be demonstrated that selecting a cytosine at position 6, or cytosine or guanosine at position 8 abrogates IFNα inducing activity. Likewise, lower IFNα inducing activity is found when selecting a nucleotide other than adenosine or uracil in the position indicated as position 17 in FIG. 6, or when selecting a RNA sequence having an adenosine or uracil in the position indicated as position 19 in FIG. 6.

Moreover, certain nucleotides at position 6-8 of the RNA sequence of step (a) showed particular high IFNα inducing activity. This sequence is shown in FIG. 6 as "Box 1". An embodiment of the invention is realized when in the sequence of the polyribonucleotide of step (a) the ribonucleotide at position 6 ("d" in SEQ ID NO: 12-19) is u, and/or the ribonucleotide at position 7 ("n" in SEQ ID NO: 12-19) is g, and/or the ribonucleotide at position 8 ("w" in SEQ ID NO: 12-19) is a. In another embodiment the ribonucleotide at position 6 ("d" in SEQ ID NO: 12-19) is g, and the ribonucleotide at position 7 ("n" in SEQ ID NO: 12-19) is c. Other embodiments is wherein in the RNA sequence of step (a) the ribonucleotides at position 6-8 are UGA (Box 1). In another embodiment, the ribonucleotide at position 6 ("d" in SEQ ID NO: 12-19) is u, the ribonucleotide at position 7 ("n" in SEQ ID NO: 12-19) is g, and the ribonucleotide at position 8 ("w" in SEQ ID NO: 12-19) is a. On the other hand, it was shown that a guanosine at position 6 and a cytosine at position 7 is also well tolerated. Hence, in another embodiment the ribonucleotide at position 6 ("d" in in SEQ ID NO: 12-19) is g, the ribonucleotide at position 7 ("n" following "d" in SEQ ID NO: 12-19) is c.

In addition, it could be shown that an adenosine at position 9 further increases the IFNα inducing activity. Hence, in another embodiment, in the sequence of the polyribonucleotide of step (a) (any one of SEQ ID NO: 12-19) the ribonucleotide at position 9 is a. Accordingly, another embodiment is wherein in the RNA sequence of step (a) the ribonucleotides at position 6-8 are GM (Box 1), in particular wherein in the RNA sequence of step (a) the ribonucleotides at position 6-9 are GAAA.

Apart from Box1, the inventors also identified another Box2 at positions 17-19. The nucleotide at position 17 is defined as adenosine or uracil ("w") in SEQ ID NOs: 12-19.

An embodiment is realized when "w" is uracil. Another embodiment is realized when "w" is adenosine. Other embodiments include those wherein the sequence at the 5'end of the polyribonucleotide in step (a) is selected from

| | |
|---|---|
| 5'-gbucndnwnnnnnnnnunsnn-3', | (SEQ ID NO: 95) |
| 5'-gucuadnwnnnnnnnnunsnn-3', | (SEQ ID NO: 96) |
| 5'-guagudnwnnnnnnnnunsnn-3', | (SEQ ID NO: 97) |
| 5'-gguaadnwnnnnnnnnunsnn-3', | (SEQ ID NO: 98) |
| 5'-ggcagdnwnnnnnnnnunsnn-3', | (SEQ ID NO: 99) |
| 5'-gcuucdnwnnnnnnnnunsnn-3', | (SEQ ID NO: 100) |
| 5'-gcccadnwnnnnnnnnunsnn-3', and | (SEQ ID NO: 101) |
| 5'-gcgcudnwnnnnnnnnunsnn-3'. | (SEQ ID NO: 102) |

In another embodiment, in the sequence of the polyribonucleotide of step (a) the ribonucleotide at position 18 (the "n" preceding "s" in SEQ ID NO: 12-19) is u, and/or the ribonucleotide at position 19 ("s" in SEQ ID NO: 12-19) is c. Along with the defined "u" at position 17 in SEQ ID NOs: 12-19, the latter reflects the consensus sequence of Box2 "uuc" (cf. FIG. 6).

It follows from the foregoing that an embodiment is one which combines the previous embodiments. Such embodiments include those wherein the sequence at the 5'end of the polyribonucleotide in step (a) is selected from

| | |
|---|---|
| 5'-gbucnugaannnnnnnuucnn-3', | (SEQ ID NO: 20) |
| 5'-gucuaugaannnnnnnuucnn-3', | (SEQ ID NO: 21) |
| 5'-guaguugaannnnnnnuucnn-3', | (SEQ ID NO: 22) |
| 5'-gguaaugaannnnnnnuucnn-3', | (SEQ ID NO: 23) |
| 5'-ggcagugaannnnnnnuucnn-3', | (SEQ ID NO: 24) |
| 5'-gcuucugaannnnnnnuucnn-3', | (SEQ ID NO: 25) |
| 5'-gcccaugaannnnnnnuucnn-3', and | (SEQ ID NO: 26) |
| 5'-gcgcuugaannnnnnnuucnn-3'.; | (SEQ ID NO: 27) |

Among these, is when the sequence at the 5'end of the polyribonucleotide in step (a) is 5'-gbucnugaannnnnnnuucnn-3' (SEQ ID NO: 20).

Generally, it was shown that active RIG-I agonists may have a length of 21-300 base pairs (cf. FIGS. 4B and 5 in Schlee et al., Immunity, 31(1): 25-34 (2009); and page in Reikine et al., Front Immunol. 5: 324 (2014)). Accordingly, the polyribonucleotide in step (a) may have a length of 21-300 nucleotides. Still, in embodiments the polyribonucleotide in step (a) may have a length of at most 250 nucleotides, at most 200 nucleotides, at most 150 nucleotides, at most 100 nucleotides, at most 90 nucleotides, at most 80 nucleotides, at most 70 nucleotides, at most 60 nucleotides, at most 55 nucleotides, at most 50 nucleotides, at most 45 nucleotides, at most 40 nucleotides, at most 38 nucleotides, such as 37 nucleotides, at most 36 nucleotides, such as 35 nucleotides, at most 34 nucleotides, such as 33 nucleotides, at most 32 nucleotides, such as 31 nucleotides, at most 30 nucleotides, such as 29 nucleotides, at most 28 nucleotides, such as 27 nucleotides, at most 26 nucleotides, such as 25 nucleotides, or 21-24 nucleotides.

Likewise, the complementary polyribonucleotide in step (b) may have a length of 21-300 nucleotides. Still, in embodiments the polyribonucleotide in step (a) may have a length of at most 250 nucleotides, at most 200 nucleotides, at most 150 nucleotides, at most 100 nucleotides, at most 90 nucleotides, at most 80 nucleotides, at most 70 nucleotides, at most 60 nucleotides, at most 55 nucleotides, at most 50 nucleotides, at most 45 nucleotides, at most 40 nucleotides, at most 38 nucleotides, such as 37 nucleotides, at most 36 nucleotides, such as 35 nucleotides, at most 34 nucleotides, such as 33 nucleotides, at most 32 nucleotides, such as 31 nucleotides, at most 30 nucleotides, such as 29 nucleotides, at most 28 nucleotides, such as 27 nucleotides, at most 26 nucleotides, such as 25 nucleotides, or 21-24 nucleotides.

It is also contemplated that the complementary polyribonucleotide in step (b) starts at the 5' end with a sequence as described above with regard to the polyribonucleotide of step (a), wherein said sequence at the 5' end of the complementary polyribonucleotide of step (b) differs or is the same as said sequence at the 5' end of the polyribonucleotide of step (a).

The complementary polyribonucleotide in step (b) has at most 2 nucleotides more in length than the polyribonucleotide of step (a); or at most 1 nucleotide more in length than the polyribonucleotide of step (a); or the complementary polyribonucleotide in step (b) has the same length than the polyribonucleotide of step (a). In an embodiment, the annealed polyribonucleotide of step (c) has a blunt end at the 5'end of the polyribonucleotide of step (a). In another embodiment the annealed polyribonucleotide of step (c) has two blunt ends.

In a another embodiment, the annealed polyribonucleotide of step (c) has two blunt ends and a length of 24 nucleotides.

The inventors further found that the aforementioned 5-mer, Box1, adenosine at position 9, and Box2 can additionally be introduced into the complementary strand. For example, the ribonucleotides in BOX1 can be selected in a way such that the complementary strand comprises the "Box2" of UUC. Still in another embodiment in the sequence of the polyribonucleotide of step (a) the ribonucleotide at position 6 ("d" in SEQ ID NO: 12-19) is g, and/or the ribonucleotide at position 7 ("n" following "d" in SEQ ID NO: 12-19) is a, and/or the ribonucleotide at position 8 ("w" in SEQ ID NO: 12-19) is a. In another embodiment, in the sequence of the polyribonucleotide of step (a) the ribonucleotide at position 6 ("d" in SEQ ID NO: 12-19) is g, the ribonucleotide at position 7 ("n" following "d" in SEQ ID NO: 12-19) is a, and the ribonucleotide at position 8 ("w" in SEQ ID NO: 12-19) is a. In this case, the complementary strand of step (b) will encompass a sequence which closely reflects the preferred consensus sequence of Box2 "uuc" as shown in FIG. 6.

In order to introduce the adenosine at position 9 into the complementary strand, in the sequence of the polyribonucleotide of step (a) the ribonucleotide at position 16 is u. The adenine at position 9 has been shown to further increase type I IFN induction. As noted above, a BOX1 motif of GCA is well tolerated. Thus, in another embodiment, such Box1 motif is introduced into the complementary strandby way that in the sequence of the polyribonucleotide of step (a) the ribonucleotide at position 17 is u, the ribonucleotide at position 18 is g, and the ribonucleotide at position 19 is c, in which case the complementary strand will comprise Box1 ($G_6C_7A_8$). Likewise, the last five ribonucleotides can be selected from any nucleotide. Accordingly, it can be selected such that the complementary strand comprises the 5-mer sequence for which high type-I IFN inducing activity could be demonstrated. In another embodiment in the polyribonucleotide of step (a) the ribonucleotide sequence at positions 20-24 is selected from 5'-ngavc-3', 5'-uagac-3', 5'-acuac-3', 5'-uuacc-3', 5'-cugcc-3', 5'-gaagc-3', 5'-ugggc-3' and 5'-agcgc-3'. An embodiment is realized when the consensus sequence is 5'-ngavc-3'. Thus, in another embodiment in the polyribonucleotide of step (a) the sequence at position 6-24 is 5'-ugaannnnnnnuucngavc-3' (SEQ ID NO: 3; thereby comprising the consensus tail sequence in the polyribonucleotide of step (a), and at the same time the consensus 5-mer sequence (and box 1) in the complementary strand of step (b)); 5'-ugaannnnnnnuucngavc-3' (SEQ ID NO: 4; thereby complying with the tail sequence in the polyribonucleotide of step (a), and at the same time comprising the consensus 5-mer sequence and Box1 in the complementary polyribonucleotide of step (b)); 5'-ugaannnnnnnuucngavc-3' (SEQ ID NO: 5; thereby complying with the tail sequence in the polyribonucleotide of step (a), and at the same time comprising the consensus 5-mer sequence, Box1, and $a_9$ in the complementary polyribonucleotide of step (b)); 5'-gaaannnnnnnuucngavc-3' (SEQ ID NO: 6, thereby complying with the tail sequence in the polyribonucleotide of step (a), and at the same time comprising the consensus 5-mer sequence, Box1, $a_9$, and Box2 in the complementary polyribonucleotide of step (b)); 5'-gaaannnnnnnuucngavc-3' (SEQ ID NO: 67), thereby complying with the tail sequence in the polyribonucleotide of step (a), and at the same time comprising the consensus 5-mer, Box1, adenosine at position 9, and Box 2 in the complementary polyribonucleotide of step (b); or 5'-gaaannnnnnnuucngavc-3' (SEQ ID NO: 68), thereby comprising the consensus 5-mer, Box1, adenosine at position 9, and Box 2 in both strands.

In combination with the 5-mer of 5'-gbucn-3', an embodiment of the invention is realized with the following ribonucleotide sequences: 5'-gbucnugaannnnnnnuucngavc-3' (SEQ ID NO: 9); 5'-gbucnugaannnnnnuucngavc-3' (SEQ ID NO: 10); 5'-gbucngaaannnnnnnuucngavc-3' (SEQ ID NO: 11); 5'-gbucngaaannnnnnnuucngavc-3' (SEQ ID NO: 69); and 5'-gbucngaaannnnnnnuucngavc-3' (SEQ ID NO: 70).

The polyribonucleotide may have a 5'OH at its 5' end, or a monophosphate at its 5' end. However, the type-I IFN inducing activity is strongly increased if the polyribonucleotide exhibits a diphosphate, triphosphate or a di-/ or triphosphate analogue (provided it does not abrogate the type-I IFN-inducing activity).

Therefore, the polyribonucleotide prepared in step (a) has a mono-, di-, or triphosphate or respective analogue attached to its 5' end, and/or that the complementary polyribonucleotide prepared in step (b) has a mono-, di-, or triphosphate or respective analogue attached to its 5' end. Since the effect of monophosphate appears to be marginal (cf. FIG. 3f in Goubau Nature 514: 372-375 (2014)), then the polyribonucleotide prepared in step (a) can have a di-, or triphosphate or respective analogue attached to its 5' end, and/or that the complementary polyribonucleotide prepared in step (b) can have a di-, or triphosphate or respective analogue attached to its 5' end. In another embodiment the polyribonucleotide prepared in step (a) has a triphosphate or respective analogue attached to its 5' end, and/or the complementary polyribonucleotide prepared in step (b) has a triphosphate or respective analogue attached to its 5' end. In another embodiment, both the polyribonucleotide prepared in step (a) and the complementary polyribonucleotide prepared in step (b) have a triphosphate attached to the 5' end.

Even though it was recently demonstrated that cap structures are tolerated (Schuberth-Wagner et al., Immunity 43(1): 41-51 (2015)), the 5' triphosphate is preferably free of any cap structure.

As set out above, the complementary polyribonucleotide of step (b) is at least 80% complementary to the polyribonucleotide of step (a) over the whole length of the polyribonucleotide of step (a). However, in certain embodiments, the percentage complementarity is higher such as at least 82% complementary to the polyribonucleotide of step (a) over the whole length of the polyribonucleotide of step (a), or at least 84%, or at least 86%, or at least 88%, or at least 90%, or at least 91%, or at least 92%, or at least 93%, or at least 94%, or at least 95%, or at least 96%, or at least 97%, or at least 98%, or at least 99%, or wherein the complementary polyribonucleotide in step (b) is fully complementary to the polyribonucleotide of step (a) over the whole length of the polyribonucleotide of step (a). If annealed, the complementary polyribonucleotide can result in a 3'-overhang of at most 2 nucleotides at the 5'end of the polyribonucleotide; or at most 1 nucleotide; or the complementary polyribonucleotide in step (b) forms a blunt end with the 5'-end of the polyribonucleotide of step (a), or two blunt ends with the polyribonucleotide of step (a).

The triphosphate/triphosphate analogue generally comprises the structure of formula (I)

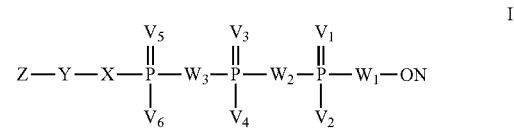

In this group, $V_1$, $V_3$ and $V_5$ are independently selected from 0, S and Se. Preferably, $V_1$, $V_3$ and $V_5$ are O. $V_2$, $V_4$ and $V_6$ are in each case independently selected from OH, $OR^1$, SH, $SR^1$, F, $NH_2$, $NHR^1$, $N(R^1)_2$ and $BH_3^-M^+$. Preferably, $V_2$, $V_4$ and $V_6$ are OH. $R^1$ may be $C_{1-6}$ alkyl, $C_{2-6}$ alkenyl, $C_{2-6}$ alkynyl, $C_{2-6}$ acyl or a cyclic group, e.g. a $C_{3-8}$ cyclo(hetero)alkyl group, a $C_{3-8}$ cyclo(hetero)alkenyl group, phenyl or $C_{5-6}$ heteroaryl group, wherein heteroatoms are selected from N, O and S. Further, two $R^1$ may form a ring, e.g. a 5- or 6-membered ring together with an N-atom bound thereto. $R^1$ may also comprise substituents such as halo, e.g. F, Cl, Br or I, O(halo)$C_{1-2}$ alkyl and—in the case of cyclic groups—(halo)$C_{1-2}$ alkyl. $M^+$ may be an inorganic or organic cation, e.g. an alkali metal cation or an ammonium or amine cation. $W_1$ may be O or S.

Preferably, $W_1$ is O. $W_2$ may be O, S, NH or $NR^2$. Preferably, $W_2$ is O. $W_3$ may be O, S, NH, $NR^2$, $CH_2$, CHHal or $C(Hal)_2$. Preferably, $W_3$ is O, $CH_2$ or $CF_2$. $R^2$ may be selected from groups as described for $R^1$ above. Hal may be F, Cl, Br or I. As noted above, according to an especially preferred embodiment $V_1$, $V_2$, $V_3$, $V_4$, $V_5$, $V_6$, $W_1$, $W_2$ and $W_3$ are O. Further suitable triphosphate analoga are described in the claims of WO 2009/060281.

Various methods for producing polyribonucleotides are known in the art. Chemical synthesis is the preferred method of preparation. The particular method or process of chemical synthesis is not important. However, it is preferred that the synthesized polyribonucleotides are purified and quality-controlled such that the polyribonucleotide preparation contains essentially a homogenous population of oligonucleotides having essentially the same chemical identity (or chemical composition), including the same nucleotide sequence, backbone, modifications, length, and end structures. In particular, the respective single-stranded as well as the annealed double-stranded polyribonucleotides may exhibit a purity of at least 90%, more preferably of at least 91%, more preferably of at least 92%, more preferably of at least 93%, more preferably of at least 94%, more preferably of at least 95%, more preferably of at least 96%, more preferably of at least 97%, more preferably of at least 98%, and most preferably of at least 99%.

The polyribonucleotides can be purified by any standard methods in the art, such as capillary gel electrophoresis and HPLC. Synthetic polyribonucleotides, either single-stranded or double-stranded, obtained from most commercial sources contain 5' OH. These synthetic oligonucleotides can be modified at the 5' end to bear a 5' triphosphate by any appropriate methods known in the art. The preferred method for 5' triphosphate attachment is that developed by János Ludwig and Fritz Eckstein (J Org Chem, 1989), or the method described on pages 4-14 and FIG. 1 in WO 2012/130886, or on pages 15-21 and in Examples 1-4 of WO 2014/049079.

Alternatively, in vitro transcription can be employed. However, in order to obtain the single strands to prepare the double-stranded polyribonucleotide by in vitro transcription, measures need to be taken to ensure that each intended in vitro transcribed single strand is indeed single-stranded. Aberrant transcripts may be generated in vitro using an RNA polymerase. For example, it is hypothesized that an RNA transcript generated by an RNA polymerase in vitro may fold back onto itself and prime RNA-dependent RNA synthesis, leading to the generation of aberrant transcripts of undefined and/or non-uniform lengths and sequences. Therefore, in principle, any measure that would prevent RNA synthesis primed by the RNA transcript itself can be employed.

For example, a single stranded polyribonucleotide is designed to have a sequence X1-X2-X3- . . . Xm-2-Xm-1-Xm, wherein m is the length of the oligonucleotide, wherein the sequence has no or minimal self-complementarity, wherein X1, X2, X3, . . . , Xm are chosen from 1, 2 or 3 of the 4 conventional nucleotides A, U, C and G, wherein at least one of the nucleotides that are complementary to any of Xm-2, Xm-1, and Xm, i.e., Ym-2, Ym-1, and Ym, is not among the 1, 2, or 3 nucleotides chosen for X1, X2, X3, . . . , Xm.

An appropriate DNA template for generating such an ssRNA oligonucleotide can be generated using any appropriate methods known in the art. An in vitro transcription reaction is set up using the DNA template and a nucleotide mixture which does not contain the complementary nucleotide(s) which is(are) not comprised in X1-X2-X3- . . . Xm-2-Xm-1-Xm. Any appropriate in vitro transcription conditions known in the art can be used. Due to the absence of the complementary nucleotide, no aberrant RNA-primed RNA synthesis can take place. As a result, a single-stranded population of X1-X2-X3- . . . -Xm can be obtained. The resulting ssRNA preparation can be purified by any appropriate methods known in the art and an equal amount of two purified ssRNA preparations with complementary sequence can be annealed to obtain an essentially homogenous population of a double-stranded RNA oligonucleotide of desired sequence.

It is also possible to synthesize the two strands forming the double-stranded oligonucleotide using different methods. For example, one strand can be prepared by chemical synthesis and the other by in vitro transcription. Furthermore, if desired, an in vitro transcribed ssRNA can be treated with a phosphatase, such as calf intestine phosphatase (CIP), to remove the 5' triphosphate.

The polyribonucleotide may contain any naturally-occurring, synthetic, modified nucleotides, or a mixture thereof, in order to increase the stability and/or delivery and/or the selectivity for RIG-I, and/or other properties of the polyribonucleotide. In doing so, it is at the same time generally attempted to minimize a reduction in the type I IFN-inducing activity of the polyribonucleotide. The polyribonucleotide may contain any naturally-occurring, synthetic, modified internucleoside linkages, or a mixture thereof, as long as the linkages do not compromise the type I IFN-inducing activity of the polyribonucleotide. The 5' phosphate groups of the polyribonucleotide may be modified as long as the modification does not compromise the type I IFN-inducing activity of the oligonucleotide. For example, one or more of the oxygen (O) in the phosphate groups may be replaced with a sulfur (S); the triphosphate group may be modified with the addition of one or more phosphate group(s).

The oligonucleotide may be modified covalently or non-covalently to improve its chemical stability, resistance to nuclease degradation, ability to cross cellular and/or sub-cellular membranes, target (organ, tissue, cell type, subcellular compartment)-specificity, pharmacokinetic properties, biodistribution, reduce its toxic side effects, optimize its elimination or any combinations thereof. For example, phosphorothioate linkage(s) and/or pyrophosphate linkage(s) may be introduced to enhance the chemical stability and/or the nuclease resistance of an RNA oligonucleotide. In another example, the RNA oligonucleotide may be covalently linked to one or more lipophilic group(s) or molecule(s), such as a lipid or a lipid-based molecule, preferably, a cholesterol, folate, anandamide, tocopherol, palmitate, or a derivative thereof. The lipophilic group or molecule is preferably not attached to the blunt end bearing the 5'phosphate groups. Preferably, the modification does not comprise the type I IFN-inducing activity of the oligonucleotide. Alternatively, a reduction in the type I IFN-inducing activity of the oligonucleotide caused by the modification is off-set by an increase in the stability and/or delivery and/or other properties as described above.

The polyribonucleotide may comprise further terminal and/or internal modifications, e.g. cell specific targeting entities covalently attached thereto. Those entities may promote cellular or cell-specific uptake and include, for example vitamins, hormones, peptides, oligosaccharides and analogues thereof. Targeting entities may e.g. be attached to modified nucleotide or non-nucleotidic building blocks by methods known to the skilled person. For example, a targeting moiety as described on pages 5-9 in WO 2012/039602 may be attached to the non-phosphorylated 5'-end of the polyribonucleotide. Moreover, nanostructure scaffolds comprising cell targeting moieties as described in Brunner et al., (Angew Chem Int Ed., 2015) may be linked to the non-tri-phosphorylated end of the polyribonucleotide.

According to a preferred embodiment modifications establish and/or enhance the selectivity of the polyribonucleotide towards a given target. In a particularly preferred embodiment the RIG-I selectivity of the polyribonucleotide is established or enhanced. Methods to determine the RIG-I selectivity of a given oligonucleotide are described in detail in Examples 5-8 of WO 2014/049079 and/or are known to the person skilled in the art.

According to another preferred embodiment the chemical modifications maintain or enhance the chemical stability of the polyribonucleotide. A person skilled in the art knows methods for determining the chemical stability of a given polyribonucleotide. Such methods are also described, e.g., in Examples 5-8 of WO 2014/049079.

According to a preferred embodiment the chemical modifications of the polyribonucleotide are independently selected from the group comprising halogenation, in particular F-halogenation, 2'-O-alkylation, in particular 2'-O-methylation, and/or phosphorothioate modifications of internucleotide linkages.

The following modifications are known in the field, and can be introduced into the polyribonucleotide(s) using routine measures only:

Internucleotide linkages: phosphodiester, phosphorothioate, $N_3$ phosphoramidate, boranophosphate, 2,5-phosphodiester, amide-linked, phosphonoacetate (PACE), morpholino, peptide nucleic acid (PNA).

The following sugar modifications are known in the field, and can be introduced into the polyribonucleotide(s) using routine measures only: RNA, DNA, 2'-O-ME, 2'F-RNA, 2'-F-ANA, 4'S-RNA, UNA, LNA, 4'S-FANA, 2'-O-MOE, 2'-O-allyl, 2'-O-ethylamine, 2'-O-cyanoethyl, 2'-O-acetalester, 4'-C-aminomethyl-2'-O-methyl RNA, 2'-azido, MC, ONA, tc-DNA, CeNA, ANA, HNA and 2',4' bridged ribosides such as, but not limited to methylene-cLNA, N-MeO-amino BNA, N-Me-aminooxy BNA, 2',4'-BNANC.

Additional modified nucleotides which may be suitably used are 2'-deoxy-2'-fluoro modified nucleotide, abasic nucleotide, 2'-amino-modified nucleotide, 2'-alkyl-modified nucleotide, and non-natural base comprising nucleotide. Particularly F-halogenation and phosphorothioate modifications increase the stability of the oligonucleotide, while 2'-O-methylation establishes or increases RIG-I selectivity of the polyribonucleotide. 2'-O-methylations are also able to modify the immunogenicity of RNA and/or stability. In a preferred embodiment, a polyribonucleotide only comprises one or two 2'-O-methylations per strand, more preferably one 2'-O-methylation per strand or even more preferably one per duplex molecule.

The 2'-F substitution is particularly preferred. At the 2' position of the ribose the hydroxyl group is substituted for fluorine. 2'-F substitutions in RNAs particularly result in an enhanced stability against nuclease digestion. A 2'-fluoro-substitution may particularly augment a RIG-I-dependent immune stimulation.

Phosphorothioate compounds in general relate to phosphorothioate modifications of internucleotide linkages. Phosphorothioate-modified compounds having a modification at a terminal end of the oligonucleotide are especially preferred. During phosphorothioate modification the non-binding oxygen atom of the bridging phosphate is substituted for a sulfur atom in the backbone of a nucleic acid. This substitution reduces the cleavability by nucleases at this position significantly and results in a higher stability of the nucleic acid strand.

The term "RIG-I agonist" as used herein relates to a polyribonucleotide comprising a double-stranded section of at least 21 base-pairs which includes the nucleotide at the 5'-end, and which often bears a triphosphate at said 5'-end. Said 5'-end comprises a 3'-overhang of at most 2 nucleotides, more preferably at most 1 nucleotide, and most preferably said 5'-end is a blunt end.

RIG-I agonistic activity can be measured by quantitation of IFNα or IP10 levels in cell culture supernatant using the human IFN alpha matched antibody pairs ELISA (eBioscience, San Diego, Calif., USA) or IP10 using the human matched antibody pairs ELISA respectively (BD Biosciences, Franklin Lakes, N.J., USA), or by IFNβ-mRNA detection via pPCR. Here, IFNα levels in cell culture supernatant of PBMCs treated with the RIG-I agonist are compared to IFNα levels in cell culture supernatant of a control, e.g. untreated cells or cells treated with an irrelevant polyribonucleotide for which is known that it does not induce type I IFN secretion. For the treatment with the RIG-I agonist, RNA is transfected into cells using Lipofectamine 2000 according to manufacturer's instructions (Invitrogen).

For example, human primary peripheral blood mononuclear cells (PBMCs) are isolated from fresh buffy coats obtained from healthy volunteers according to standard protocols (Schuberth-Wagner et al., Immunity 43(1): 41-51 (2015), the content of which is incorporated herein by reference). PBMCs ($2.6 \times 10^6$ cells/ml) are seeded in 96-well plates and maintained in RPMI1640 supplemented with 10% FCS, 1.5 mM L-glutamine and 1× penicillin/streptomycin. PBMCs are then stimulated once with 5 nM of the RIG-I agonist and conditioned medium is collected after 17 hrs and measured for IFNα levels using the human IFN alpha matched antibody pairs ELISA (eBioscience, San Diego, Calif., USA). In order to prevent endosomal TLR activation, PBMCs can be pre-treated with 5 µg/ml chloroquine (Sigma Aldrich) for at least 1 hr. A RIG-I agonist is capable of inducing at least 50 pg/ml IFNα, more preferably at least 100 pg/ml IFNα, even more preferably at least 150 pg/ml IFNα. In even more preferred embodiments, the RIG-I agonist is capable of inducing at least 200 pg/ml IFNα, more preferably at least 250 pg/ml IFNα, even more preferably at least 500 pg/ml, still more preferably at least 1000 pg/ml IFNα, and in a most preferred embodiment at least 2000 pg/ml IFNα.

Alternatively, CaSki cells (Cell Lines Services; Germany) are stimulated once or twice depending on the duration of the experiment (3 or 6d). For the long term experiment (6d), CaSki cells are treated on d0 and d3. Thereafter, cell culture supernatants are collected and measured for IP10 levels using the human IP-10 matched antibody pairs ELISA (BD Biosciences, Franklin Lakes, N.J., USA). Alternatively the induction of IFNβ mRNA can be measured via qPCR analysis, using routine measures only.

In some embodiments, the RIG-I agonist has one blunt end which bears a 5' triphosphate and one end with a 5' or 3' overhang, wherein the 5' or 3' overhang is composed of deoxyribonucleotides and contains defined sequence motifs recognized by TLR9 as known in the field. In preferred embodiments, the 5' or 3' overhang of the RIG-I agonist comprises one or more unmethylated CpG dinucleotides. The RIG-I agonist may contain one or more of the same or different structural motif(s) or molecular signature(s) recognized by TLR3, TLR7, TLR8 and TLR9 as known in the field.

By "fully complementary", it is meant that the annealed double-stranded polyribonucleotide is not interrupted by any single-stranded structures. A polyribonucleotide section is fully complementary when the two strands forming the section have the same length and the sequences of the two strands are 100% complementary to each other. As established in the art, two nucleotides are said to be complementary to each other if they can form a base pair, either a Waston-Crick base pair (A-U, G-C) or a wobble base pair (U-G, U-A, I-A, I-U, I-C). Mismatch of one or two nucleotides may be tolerated in the double-stranded section of the polyribonucleotide in that the IFN-inducing activity of the polyribonucleotide is not significantly reduced. The mismatch is preferably at least 6 bp, more preferably at least 12 bp, even more preferably at least 18 pb away from the 5'-end bearing the 5-mer sequence.

In one embodiment, the double- or single-stranded RNA oligonucleotide contains one or more GU wobble base pairs instead of GC or UA base pairing. In a preferred embodiment, at least 1, 2, 3, 4, 5%, preferably at least 10, 15, 20, 25, 30%, more preferably at least 35, 40, 45, 50, 55, 60%, even more preferably at least 70, 80, or 90% of the adenosine (A) and/or guanosine (G) in the oligonucleotide is replaced with inosine (I).

Also provided is a RIG-I agonist obtainable by the method of the present disclosure.

Preferably, said RIG-I agonist is a polyribonucleotide comprising at least one synthetic or modified internucleoside linkage such as phosphodiester, phosphorothioate, N3 phosphoramidate, boranophosphate, 2,5-phosphodiester, amide-linked, phosphonoacetate (PACE), morpholino, peptide nucleic acid (PNA), or a mixture thereof, provided the linkage(s) do not compromise the type I IFN-inducing activity of the polyribonucleotide. In a more preferred embodiment, the said RIG-I agonist is a polyribonucleotide comprising phosphorothioate linkage(s) and/or pyrophosphate linkage(s). Optionally, the RIG-I agonist may comprise at least one modified nucleotide selected from pseudouridine, 2-thiouridine, 2'-fluorine-dNTP, 2'-O-methylated NTP.

The following modifications are known in the field, and can be introduced into the polyribonucleotide(s) using routine measures only:

Internucleotide linkages: phosphodiester, phosphorothioate, $N_3$ phosphoramidate, boranophosphate, 2,5-phosphodiester, amide-linked, phosphonoacetate (PACE), morpholino, peptide nucleic acid (PNA).

The following sugar modifications are known in the field, and can be introduced into the polyribonucleotide(s) using routine measures only: RNA, DNA, 2'-O-ME, 2'F-RNA, 2'F-ANA, 4'S-RNA, UNA, LNA, 4'S-FANA, 2'-O-MOE, 2'-O-allyl, 2'-O-ethylamine, 2'-O-cyanoethyl, 2'-O-acetal-ester, 4'-C-aminomethyl-2'-O-methyl RNA, 2'-azido, MC, ONA, tc-DNA, CeNA, ANA, HNA and 2',4' bridged ribosides such as, but not limited to methylene-cLNA, N-MeO-amino BNA, N-Me-aminooxy BNA, 2',4'-BNANC.

Additional modified nucleotides which may be suitably used are 2'-deoxy-2'-fluoro modified nucleotide, abasic nucleotide, 2'-amino-modified nucleotide, 2'-alkyl-modified nucleotide, and non-natural base comprising nucleotide. Particularly F-halogenation and phosphorothioate modifications increase the stability of the oligonucleotide, while 2'-O-methylation establishes or increases RIG-I selectivity of the polyribonucleotide. 2'-O-methylations are also able to modify the immunogenicity of RNA and/or stability. In a preferred embodiment, a polyribonucleotide only comprises one or two 2'-O-methylations per strand, more preferably one 2'-O-methylation per strand or even more preferably one per duplex molecule.

The 2'-F substitution is particularly preferred. At the 2' position of the ribose the hydroxyl group is substituted for fluorine. 2'-F substitutions in RNAs particularly result in an enhanced stability against nuclease digestion. A 2'-fluoro-substitution may particularly augment a RIG-I-dependent immune stimulation.

Alternatively, the polyribonucleotide of the present disclosure may be free of modifications selected from the group of modifications, consisting of pseudouridine, and 2-thiouridine.

Pharmaceutical Composition

A further aspect of the present invention relates to a pharmaceutical composition comprising a RIG-I agonist obtainable by a method of the present disclosure. The pharmaceutical composition described herein may further comprise pharmaceutically acceptable carriers, diluents, and/or adjuvants.

The pharmaceutical composition may be formulated in any way that is compatible with its therapeutic application, including intended route of administration, delivery format and desired dosage. Optimal pharmaceutical compositions may be formulated by a skilled person according to common general knowledge in the art, such as that described in Remington's Pharmaceutical Sciences (18th Ed., Gennaro A R ed., Mack Publishing Company, 1990).

The pharmaceutical composition may be formulated for instant release, controlled release, timed-release, sustained release, extended release, or continuous release.

The pharmaceutical composition may be administered by any route known in the art, including, but not limited to, topical, enteral and parenteral routes, provided that it is compatible with the intended application. Topic administration includes, but is not limited to, epicutaneous, inhalational, intranasal, vaginal administration, enema, eye drops, and ear drops. Enteral administration includes, but is not limited to, oral, rectal administration and administration through feeding tubes. Parenteral administration includes, but is not limited to, intravenous, intraarterial, intramuscular, intracardiac, subcutaneous, intraosseous, intradermal, intrathecal, intraperitoneal, transdermal, transmucosal, intratumoral, and inhalational administration.

In a preferred embodiment, the RIG-I agonist or pharmaceutical composition of the present disclosure is for local (e.g., mucosa, skin) applications, such as in the form of a spray (i.e., aerosol) preparation. In another preferred embodiment, the RIG-I agonist or pharmaceutical composition of the present disclosure is for intratumoral administration in the treatment of visceral tumors. The pharmaceutical composition may, for example, be formulated for intravenous or subcutaneous administration, and therefore preferably comprises an aqueous basis (buffers, isotonic solutions etc.), one or more stabilizer, one or more cryoprotective, one or more bulking agent, one or more excipient like salt, sugar, sugar alcohol, one or more tonicity agent, and if needed one or more preserving agent. The pharmaceutical composition may also comprise one or more transfection reagent, which enables an effective and protected transport of the RIG-I agonist into the cytosol of the cell where the RIG-I receptor is located. Transfection or complexation reagents are also referred to as "carrier" or "delivery vehicle" in the art.

Buffer solutions are aqueous solutions of a mixture of a weak acid and its conjugate base, or vice versa. This buffer solution only causes slight pH changes when a small amount of a strong acid or base is added to the system. Buffer solutions are used as a means of keeping pH at a nearly constant value in a wide variety of chemical applications. Buffers used for a drug product formulation mainly contain liquids and substances that are listed in the Pharmacopoeia and which are non-toxic to the cell or mammal being exposed to at the dosages and concentrations employed. These buffer systems are also called "biological buffers" and often include, but are not limited to, substances like maleic-, phosphoric-, lactic-, malic-, citric-, succinic-, acetic-, formic-, pivalic-, boric- and picolinicacid, sodium acetate, sodium chloride, potassium chloride, acetone, ammonium sulfate, ammonium acetate, copper sulfate, phthalate, pyridine, piperazine, histidine, MES, Tris, HEPES, imidazole, MOPS, BES, DIPSO, TAPSO, TEA, Glycine, ethanolamine, CAPSO, and piperidine.

Besides buffer systems also other solutions/liquids which are common for pharmaceutical use are also used for the formulation of the RIG-I agonist, e.g. sodium chloride (NaCl 0.9%), Glucose 5%, phosphate buffered saline, (Krebs-)Ringer solution or water for Injections (WFI). With regard to the pharmaceutical composition of the present disclosure, a trehalose based Tris-phosphate buffer is preferred. Trehalose or other sugars or sugar alcohols like sucrose are very often used as cryoprotectants, especially if the final drug product is desired as a lyophilized formulation.

Moreover, anti-oxidants including ascorbic acid, low molecular weight (less than about 10 residues) polypeptides; proteins such as serum albumin, gelatine or immunoglobulins; hydrophilic polymers such as polyvinylpyrolidone, aminoacids such as glycine, glutamine, asparagine, arginine or lysine; monosaccharides, disaccharides and other carbohydrates including glucose, mannose or dextrins, gelating agents such as EDTA, sugar, alcohols such as mannitol or sorbitol; salt-forming counterions such as sodium; and/or non-ionic surfactants such as TWEEN, polyethylene or polyethylene glycol are also often included to improve stability of final pharmaceutical composition.

The delivery vehicle in an oligonucleotide based drug product formulation is a complexation reagent which forms a complex with the oligonucleotide and facilitates the delivery of the oligonucleotide into the cells.

Any delivery vehicle which is compatible with the intended use of the pharmaceutical composition can be employed. Examples of complexation reagents include a wide range of different polymers (branched and linear), liposomes, lipids, peptides and biodegradable microspheres. According to an especially preferred embodiment the compound of the invention is dissolved in sterile deionized water before it is complexed to a linear polyethylenimine (in vivo-jetPEI™ (PolyPlus)) which leads to a formation of positive charged polyplexes which facilitates the transfer and the uptake of the oligonucleotide into the cells. But also other polymers like dendrimers, branched polymers, viromers or other modified polymers are possible carrier systems for a RIG-I targeting oligonucleotide. Besides polymers also lipid based transfection reagents are able to complex or encapsulate the oligonucleotide. This group of delivery vehicles include neutral or mono- and polycationic lipids, lipid nanoparticles (LNP), liposomes, virosomes, stable-nucleic-acid-lipid particles (SNALPs), SICOMATRIX® (CSL Limited), poly (D,L-lactide-co-glycoliic acid PLGA) and also modified lipid reagents. Furthermore, also polycationic peptides like poly-L-Lysine, poly-L-Arginine or protamine do have the ability to delivery oligonucleotides into cells.

In addition to being delivered by a delivery agent, the oligonucleotide and/or the pharmaceutical composition can be delivered into cells via physical means such as electroporation, shock wave administration, ultrasound triggered transfection, and gene gun delivery with gold particles.

The pharmaceutical composition may further comprise another reagent such as a reagent that only stabilizes the oligonucleotide. Examples of a stabilizing reagent include a protein that complexes with the oligonucleotide to form an iRNP, chelators such as EDTA, salts, and RNase inhibitors.

In another embodiment, the delivery agent is a virus, preferably a replication-deficient virus. The oligonucleotide to be delivered is contained in the viral capsule and the virus may be selected based on its target specificity. Examples of useful viruses include polymyxoviruses which target upper respiratory tract epithelia and other cells, hepatitis B virus which targets liver cells, influenza virus which targets epithelial cells and other cells, adenoviruses which targets a number of different cell types, papilloma viruses which targets epithelial and squamous cells, herpes virus which targets neurons, retroviruses such as HIV which targets $CD4^+$ T cells, dendritic cells and other cells, modified Vaccinia Ankara which targets a variety of cells, and oncolytic viruses which target tumor cells. Examples of oncolytic viruses include naturally occurring wild-type Newcastle disease virus, attenuated strains of reovirus, vesicular stomatitis virus (VSV), and genetically engineered mutants of herpes simplex virus type 1 (HSV-1), adenovirus, poxvirus and measles virus.

In another embodiment the delivery agent is a virus like particle. In a further preferred embodiment, the virus-like particle is a recombinant virus-like particle. Also preferred, the virus-like particle is free of a lipoprotein envelope. Preferably, the recombinant virus-like particle comprises, or alternatively consists of, recombinant proteins of Hepatitis B virus, measles virus, Sindbis virus, Rotavirus, Foot-and-Mouth-Disease virus, Retrovirus, Norwalk virus or human Papilloma virus, RNA-phages, Qβ-phage, GA-phage, fr-phage, AP205-phage and Ty.

In addition to being delivered by a delivery agent, the oligonucleotide and/or the pharmaceutical composition can be delivered into cells via physical means such as electroporation, shock wave administration, ultrasound triggered transfection, and gene gun delivery with gold particles.

In certain embodiments, the pharmaceutical composition further comprises one or more pharmaceutically active therapeutic agent(s). Alternatively, the RIG-I agonist or the pharmaceutical composition of the present disclosure are for use in a combination treatment with one or more pharmaceutically active therapeutic agent(s). Examples of a pharmaceutically active agent include immunostimulatory agents, immunomodulatory agents, vaccines, anti-viral agents, antibiotics, anti-fungal agents, anti-parasitic agents, anti-tumor agents, cytokines, chemokines, growth factors, anti-angiogenic factors, chemotherapeutic agents, antibodies, checkpoint inhibitors, and gene silencing agents. Preferably, the pharmaceutically active agent is selected from the group consisting of an immunomodulatory agent, an anti-viral agent and an anti-tumor agent. The more than one pharmaceutically active agents may be of the same or different category. The RIG-I agonist or the pharmaceutical composition of the present disclosure are also contemplated for use in combination with radiation treatment, ultrasound treatment, and/or heat- or thermo-treatment. The above-mentioned vaccines can be proteins, attenuated viruses, live viruses, epitopes, or mRNAs. In another embodiment the RIG-I agonist itself is used as an adjuvant in vaccines, in accordance with, e.g. Pasquale et al. Vaccines 2015; 3: 320-343. In certain embodiments, the pharmaceutical composition further comprises retinoid acid, IFN-α and/or IFN-β. Without being bound by any theory, retinoid acid, IFN-α and/or IFN-β are capable of sensitizing cells for type-I IFN production, possibly through the upregulation of RIG-I expression.

The pharmaceutical composition may be use for prophylactic and/or therapeutic purposes. For example, a spray (i.e., aerosol) preparation may be used to strengthen the anti-viral capability of the nasal and the pulmonary mucosa.

Such a composition and/or formulation according to the invention can be administered to a subject in need thereof, particularly a human patient, in a sufficient dose for the treatment of the specific conditions by suitable means or a healthy human for prophylaxis or adjuvant activity. For example, the composition and/or formulation according to the invention may be formulated as a pharmaceutical composition together with pharmaceutically acceptable carriers, diluents and/or adjuvants. Therapeutic efficiency and toxicity may be determined according to standard protocols. The pharmaceutical composition may be administered systemically, e.g. intraperitoneally, intramuscularly, or intravenously or locally such as intranasally, subcutaneously, intradermally or intrathecally. The dose of the composition and/or formulation administered will, of course, be dependent on the subject to be treated and on the condition of the subject such as the subject's weight, the subject's age and the type and severity of the disease or disorder to be treated, the manner of administration and the judgement of the prescribing physician.

In a preferred embodiment the pharmaceutical composition is administered intradermally. It is especially preferred that the composition is administered intradermally via tattooing, microneedling and/or microneedle patches.

The RIG-I agonist of the present disclosure is preferably dissolved and diluted to the desired concentration in sterile, deionized water (purified water) and is then applied on the shaved, ethanol-disinfected skin using a pipetting device, and subsequently tattooed into the skin. For tattooing, for example, the water-based pharmaceutical composition according to the invention is intradermally injected into the skin, using a (medical) tattoo device fitted with a multi-needle (single use) needle-tip (such as a 9-needle, single-use tip).

The typical tattooing procedure is as follows: After the water-based pharmaceutical composition is pipetted onto the shaved and ethanol cleaned skin, it is introduced into the tattoo machine's multi-needle tip by placing the running needle tip (running at a speed of, for example, 100-120 Hz, in particular at 100 Hz) gently on top of the droplet of water-based pharmaceutical composition. Once the droplet of water-based pharmaceutical composition is completely adsorbed in the running needle tip, and hence resides in between the running needles, the running tip is gently moved back and forth over the skin, by holding the now filled needle tip in an exact 90 degree angle to the skin. Using this method, the water-based pharmaceutical composition is completely tattooed into the skin. For instance, for 50-100 µl of water-based pharmaceutical composition this typically takes 10-15 seconds, over a skin area of 2-4 square centimeters. The benefit of this treatment over standard single intradermal bolus injection, is that the water-based pharmaceutical composition is evenly injected over a larger area of skin, and is more evenly and more precisely divided over the target tissue: By using a 9-needle tip at 100 Hz for 10 seconds, this method ensures 9000 evenly dispersed intradermal injections in the treated skin.

Of course, a person skilled in the art may deviate from and adjust the procedure, depending on the patient or part of the body to be treated. The microneedling procedure may be carried out in close analogy to the tattooing procedure. However, with microneedling the tattoo needle-tip is replaced by a microneedling tip, which ensures more superficial intradermal administration. The water-based pharmaceutical composition is in principle pipetted onto the shaved and ethanol cleaned skin and then administered intradermally using the microneedling tip, in analogy to the tattoo procedure. Microneedling does not have necessity to prior adsorption of the pharmaceutical composition in between the microneedling needles.

Additionally, it is envisioned that fractional laser technology (PMC2921736) with, or otherwise harbouring, the pharmaceutical composition can be used for transdermal/intradermal delivery. This may have the specific advantage that the intradermal delivery of the pharmaceutical composition can be enhanced as the laser-generated cutaneous channels provide an enlarged cutaneous surface area suggesting that this might substantiate the efficacy.

In Vitro Applications

The present application provides the in vitro use of the RIG-I agonist described above. In particular, the present application provides the use of at least one RIG-I agonist of the present disclosure for inducing an anti-viral response, in particular, a type I IFN response, more specifically, an IFN-α/β or IP10 response, in vitro. The present application also provides the use of at least one RIG-I agonist obtainable by the methods of the present disclosure for inducing apoptosis of a tumor cell in vitro.

The present disclosure provides an in vitro method for stimulating an anti-viral response, in particular, a type I IFN response, more specifically, an IFN-α, IFN-β or IP10 response in a cell, comprising the steps of (a) mixing at least one RIG-I agonist obtainable by the methods of the present disclosure and as described above with a complexation agent; and (b) contacting a cell with the mixture of (a), wherein the cell expresses RIG-I.

The cells may express RIG-I endogenously and/or exogenously from an exogenous nucleic acid (RNA or DNA). The exogenous DNA may be a plasmid DNA, a viral vector, or a portion thereof. The exogenous DNA may be integrated into the genome of the cell or may exist extra-chromosomally. The cells include, but are not limited to, primary immune cells, primary non-immune cells, and cell lines. Immune cells include, but are not limited to, peripheral blood mononuclear cells (PBMC), plasmacytoid dendritic cells (PDC), myeloid dendritic cells (MDC), macrophages, monocytes, B cells, natural killer cells, granulocytes, $CD4^+$ T cells, $CD8^+$ T cells, and NKT cells. Non-immune cells include, but are not limited to, fibroblasts, endothelial cells, epithelial cells such as keratinocytes, and tumor cells. Cell lines may be derived from immune cells or non-immune cells. Further examples of suitable cell lines can be found in the examples section below.

The present disclosure also provides an in vitro method for inducing apoptosis of a tumor cell, comprising the steps of: (a) mixing at least one RIG-I agonist obtainable by the methods of the present disclosure and as described above with a complexation agent; and (b) contacting a tumor cell with the mixture of (a). The tumor cell may be a primary tumor cell freshly isolated from a vertebrate animal having a tumor or a tumor cell line. Alternatively, the cell may also be a virus infected cell.

In Vivo Applications

The present application provides the in vivo use of the oligonucleotide preparation of the invention described above.

In particular, the present application provides at least one RIG-I agonist obtainable by the methods of the present disclosure and as described above for use in inducing an anti-viral response, in particular, a type I IFN response, more specifically, an IFN-α and β response, in a vertebrate animal, in particular, a mammal. The present application further provides at least one RIG-I agonist obtainable by the methods of the present disclosure and as described above for use in inducing apoptosis of a tumor cell in a vertebrate animal, in particular, a mammal. The present application additionally provides at least one RIG-I agonist obtainable by the methods of the present disclosure and as described above for use in preventing and/or treating a disease and/or disorder in a vertebrate animal, in particular, a mammal, in medical and/or veterinary practice. The diseases and/or disorders include, but are not limited to, infections, tumors/cancers, and immune disorders.

Infections include, but are not limited to, viral infections, bacterial infections, parasitic infections, fungal infections and prion infection. Viral infections include, but are not limited to, infections by hepatitis C, hepatitis B, influenza virus, herpes simplex virus (HSV), human immunodeficiency virus (HIV), respiratory syncytial virus (RSV), vesicular stomatitis virus (VSV), cytomegalovirus (CMV), poliovirus, encephalomyocarditis virus (EMCV), human papillomavirus (HPV), west nile virus, zika virus, SARS, and smallpox virus. In one embodiment, the infection is an upper respiratory tract infection caused by viruses and/or bacteria, in particular, flu, more specifically, bird flu. Bacterial infections include, but are not limited to, infections by streptococci, staphylococci, *E. coli*, *B. anthracis*, and *pseudomonas*. In one embodiment, the bacterial infection is an intracellular bacterial infection which is an infection by an intracellular bacterium such as mycobacteria (tuberculosis), chlamydia, mycoplasma, listeria, and an facultative intracelluar bacterium such as *Staphylococcus aureus*. Parasitic infections include, but are not limited to, worm infections, in particular, intestinal worm infection.

In a preferred embodiment, the infection is a viral infection or an intracellular bacterial infection. In a more preferred embodiment, the infection is a viral infection by hepatitis C, hepatitis B, influenza virus, RSV, HPV, HSV1, HSV2, and CMV.

In this context, the RIG-I agonist or pharmaceutical composition comprising same is also contemplated for use in the treatment of condylomata warts, which are HPV-related.

Tumors include both benign and malignant tumors (i.e., cancer). Cancers include, but are not limited to biliary tract cancer, brain cancer, breast cancer, cervical cancer, choriocarcinoma, colon cancer, endometrial cancer, esophageal cancer, gastric cancer, intraepithelial neoplasm, leukemia, lymphoma, liver cancer, lung cancer, melanoma, myelomas, neuroblastoma, oral cancer, ovarian cancer, pancreatic cancer, prostate cancer, rectal cancer, sarcoma, skin cancer, testicular cancer, thyroid cancer and renal cancer.

In certain embodiments, the cancer is selected from hairy cell leukemia, chronic myelogenous leukemia, acute lymphoblastic leukemia cutaneous T-cell leukemia, acute myeloid leukemia, chronic myeloid leukemia, non-Hodgkin's lymphoma, multiple myeloma, follicular lymphoma, malignant melanoma, squamous cell carcinoma, renal cell carcinoma, prostate carcinoma, bladder cell carcinoma, breast carcinoma, ovarian carcinoma, non-small cell lung cancer, small cell lung cancer, hepatocellular carcinoma, basaliom, colon carcinoma, cervical dysplasia, head and neck cancer, mamma carcinoma, bile duct cancer, bone cancers, esophageal cancer, gastric cancer, lymphoma, Merkel cell carcinoma, mesothelioma, pancreatic cancer, parathyroid cancer, multiple myeloma, rectal cancer, testicular cancer, vaginal cancer and Kaposi's sarcoma (AIDS-related and non-AiDS related) as well as all metastatic variants thereof.

In this context, the RIG-I agonist or pharmaceutical composition comprising same is also contemplated for use in the treatment of precancer actinic keratosis (the current treatment of which is ingenol-mebutate via necrosis/apoptosis).

Immune disorders include, but are not limited to, allergies, autoimmune disorders, and immunodeficiencies. Allergies include, but are not limited to, respiratory allergies, contact allergies and food allergies, and may further encompass allergy related conditions such as asthma, in particular allergic asthma, dermatitis, in particular atopic dermatitis and eczematous dermatitis, and allergic encephalomyelitis. Autoimmune diseases include, but are not limited to, multiple sclerosis, diabetes mellitus, arthritis (including rheumatoid arthritis, juvenile rheumatoid arthritis, osteoarthritis, psoriatic arthritis and psoriasis), encephalomyelitis, myasthenia gravis, systemic lupus erythematosis, autoimmune thyroiditis, psoriasis, Sjogren's Syndrome, Crohn's disease, aphthous ulcer, iritis, conjunctivitis, keratoconjunctivitis, ulcerative colitis, systemic and cutaneous lupus erythematosus, scleroderma, vaginitis, proctitis, drug eruptions, leprosy reversal reactions, erythema nodosum leprosum, autoimmune uveitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Graves' disease, sarcoidosis, primary biliary cirrhosis, uveitis posterior, and interstitial lung fibrosis.

Immunodeficiencies include, but are not limited to, spontaneous immunodeficiency, acquired immunodeficiency (including AIDS), drug-induced immunodeficiency or immunosuppression (such as that induced by immunosuppressants used in transplantation and chemotherapeutic agents used for treating cancer), and immunosuppression caused by chronic hemodialysis, trauma or surgical procedures.

In a preferred embodiment, the immune disorder is multiple sclerosis.

In certain embodiments, the oligonucleotide is used in combination with one or more pharmaceutically active agents such as immunostimulatory agents, anti-viral agents, antibiotics, anti-fungal agents, anti-parasitic agents, anti-tumor agents, cytokines, chemokines, growth factors, anti-angiogenic factors, chemotherapeutic agents, antibodies, checkpoint-inhibitors, and gene silencing agents. Preferably, the pharmaceutically active agent is selected from the group consisting of an immunostimulatory agent, an anti-viral agent and an anti-tumor agent. The more than one pharmaceutically active agents may be of the same or different category.

The invention also provides at least one RIG-I agonist obtainable by the methods of the present disclosure and as described above for use as a vaccine adjuvant. In one embodiments, the RIG-I agonist is used in combination with an anti-viral vaccine, an anti-bacterial vaccine, and/or an anti-tumor vaccine, wherein the vaccine can be prophylactic and/or therapeutic. The vaccine composition may be a vaccine in the field of oncology, immune disorders, autoimmune diseases, asthma, or allergy and infection.

The pharmaceutical composition may be used in combination with one or more prophylactic and/or therapeutic treatments of diseases and/or disorders such as infection, tumor, and immune disorders. The treatments may be pharmacological and/or physical (e.g., surgery, radiation, ultrasound treatment, and/or heat- or thermo-treatment).

Vertebrate animals include, but are not limited to, fish, amphibians, birds, and mammals. Mammals include, but are not limited to, rats, mice, cats, dogs, horses, sheep, cattle, cows, pigs, rabbits, non-human primates, and humans. In a preferred embodiment, the mammal is human.

The invention is further described by the following embodiments:
1. A method for producing a RIG-I agonist, comprising the steps of
   (a) preparing a first polyribonucleotide with 21-300 nucleotides in length, which polyribonucleotide starts at the 5' end with a sequence selected from

| | |
   |---|---|
   | 5'-gbucndnwnnnnnnnnwnsnn-3', | (SEQ ID NO: 12) |
   | 5'-gucuadnwnnnnnnnnwnsnn-3', | (SEQ ID NO: 13) |
   | 5'-guagudnwnnnnnnnnwnsnn-3', | (SEQ ID NO: 14) |
   | 5'-gguaadnwnnnnnnnnwnsnn-3', | (SEQ ID NO: 15) |
   | 5'-ggcagdnwnnnnnnnnwnsnn-3', | (SEQ ID NO: 16) |
   | 5'-gcuucdnwnnnnnnnnwnsnn-3', | (SEQ ID NO: 17) |
   | 5'-gcccadnwnnnnnnnnwnsnn-3', and | (SEQ ID NO: 18) |
   | 5'-gcgcudnwnnnnnnnnwnsnn-3'; | (SEQ ID NO: 19) |

(b) preparing a second polyribonucleotide with 21-300 nucleotides in length which is at least 80% complementary to the first polyribonucleotide of step (a) over the whole length of the first polyribonucleotide of step (a), and which, if annealed to the first polyribonucleotide of step (a), exhibits a 3' overhang of at most 2 nucleotides, more preferably at most 1 nucleotide, and most preferably forms a blunt end with the 5' end of the polyribonucleotide of step (a); and
   (c) annealing the first polyribonucleotide of step (a) with the second polyribonucleotide of step (b), thereby obtaining a RIG-I agonist.
2. The method of embodiment 1, wherein in the sequence of the polyribonucleotide of step (a) the ribonucleotide at position 6 is u.
3. The method of embodiment 1 or 2, wherein in the sequence of the polyribonucleotide of step (a) the ribonucleotide at position 7 is g.
4. The method of embodiment 1, wherein in the sequence of the polyribonucleotide of step (a) the ribonucleotide at position 6 is g, and the ribonucleotide at position 7 is c.
5. The method of any one of embodiments 1-4, wherein in the sequence of the polyribonucleotide of step (a) the ribonucleotide at position 8 is a.
6. The method of any one of embodiments 1-5, wherein in the sequence of the polyribonucleotide of step (a) the ribonucleotide at position 9 is a.
7. The method of any one of embodiments 1-6, wherein in the sequence of the polyribonucleotide of step (a) the ribonucleotide at position 17 is u, and/or wherein the sequence at the 5'end of the polyribonucleotide in step (a) is selected from

| | |
   |---|---|
   | 5'-gbucndnwnnnnnnnnnunsnn-3', | (SEQ ID NO: 95) |
   | 5'-gucuadnwnnnnnnnnnunsnn-3', | (SEQ ID NO: 96) |
   | 5'-guagudnwnnnnnnnnnunsnn-3', | (SEQ ID NO: 97) |
   | 5'-gguaadnwnnnnnnnnnunsnn-3', | (SEQ ID NO: 98) |
   | 5'-ggcagdnwnnnnnnnnnunsnn-3', | (SEQ ID NO: 99) |
   | 5'-gcuucdnwnnnnnnnnnunsnn-3', | (SEQ ID NO: 100) |
   | 5'-gcccadnwnnnnnnnnnunsnn-3', and | (SEQ ID NO: 101) |
   | 5'-gcgcudnwnnnnnnnnnunsnn-3'. | (SEQ ID NO: 102) |

8. The method of any one of embodiments 1-7, wherein in the sequence of the polyribonucleotide of step (a) the ribonucleotide at position 18 is u.
9. The method of any one of embodiments 1-8, wherein in the sequence of the polyribonucleotide of step (a) the ribonucleotide at position 19 is c.
10. The method of embodiment 1, wherein the sequence at the 5'end of the polyribonucleotide in step (a) is selected from

| | |
   |---|---|
   | 5'-gbucnugaannnnnnnuucnn-3', | (SEQ ID NO: 20) |
   | 5'-gucuaugaannnnnnnuucnn-3', | (SEQ ID NO: 21) |
   | 5'-guaguugaannnnnnnuucnn-3', | (SEQ ID NO: 22) |
   | 5'-gguaaugaannnnnnnuucnn-3', | (SEQ ID NO: 23) |
   | 5'-ggcagugaannnnnnnuucnn-3', | (SEQ ID NO: 24) |
   | 5'-gcuucugaannnnnnnuucnn-3', | (SEQ ID NO: 25) |
   | 5'-gcccaugaannnnnnnuucnn-3', and | (SEQ ID NO: 26) |
   | 5'-gcgcuugaannnnnnnuucnn-3'; | (SEQ ID NO: 27) | preferably wherein the sequence at the 5'end of the polyribonucleotide in step (a) is 5'-gbucnugaannnnnnuucnn-3' (SEQ ID NO: 20), more preferably wherein the sequence at the 5'end of the polyribonucleotide in step (a) is 5'-gbucnugaaannnnnuuucnn-3' (SEQ ID NO: 66).
11. The method of any one of embodiments 1-10, wherein the polyribonucleotide in step (a) has a length of at most 250 nucleotides, preferably at most 200 nucleotides, more preferably at most 150 nucleotides, more preferably at most 100 nucleotides, more preferably at most 90 nucleotides, more preferably at most 80 nucleotides, more preferably at most 70 nucleotides, more preferably at most 60 nucleotides, more preferably at most 55 nucleotides, preferably at most 50 nucleotides, more preferably at most 45 nucleotides, more preferably at most 40 nucleotides, more preferably at most 38 nucleotides, such as 37 nucleotides, more preferably at most 36 nucleotides, such as 35 nucleotides, more preferably at most 34 nucleotides, such as 33 nucleotides, more preferably at most 32 nucleotides, such as 31 nucleotides, more preferably at most 30 nucleotides, such as 29 nucleotides, more preferably at most 28 nucleotides, such as 27 nucleotides, more preferably at most 26 nucleotides, such as 25 nucleotides, and most preferably 21-24 nucleotides.
12. The method of any one of embodiments 1-11, wherein the complementary polyribonucleotide in step (b) starts at the 5' end with a sequence as defined in embodiments 1-10 with regard to the polyribonucleotide of step (a), wherein said sequence at the 5' end of the complementary polyribonucleotide of step (b) differs or is the same as said sequence at the 5' end of the polyribonucleotide of step (a).
13. The method of any one of embodiments 1-12, wherein the complementary polyribonucleotide in step (b) is at least 82% complementary to the first polyribonucleotide of step (a) over the whole length of the first polyribonucleotide of step (a), preferably at least 84%, more preferably at least 86%, more preferably at least 88%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, and most preferably wherein the complementary polyribonucleotide in step (b) is fully complementary to the first polyribonucleotide of step (a) over the whole length of the first polyribonucleotide of step (a).

14. The method of any one of embodiments 1-13, wherein the complementary polyribonucleotide in step (b) has at most 2 nucleotides more in length than the polyribonucleotide of step (a); preferably at most 1 nucleotide more in length than the polyribonucleotide of step (a); and most preferably the complementary polyribonucleotide in step (b) has the same length than the polyribonucleotide of step (a).

15. The method of embodiment 14, wherein the annealed polyribonucleotide of step (c) has a blunt end at the 5'end of the polyribonucleotide of step (a).

16. The method of embodiment 15, wherein the annealed polyribonucleotide of step (c) has two blunt ends.

17. The method of embodiment 16, wherein the polyribonucleotide in step (a) has a length of 24 nucleotides.

18. The method of any one of embodiment 17, wherein in the polyribonucleotide of step (a) the ribonucleotide sequence at positions 20-24 is selected from 5'-ngavc-3', 5'-uagac-3', 5'-acuac-3', 5'-uuacc-3', 5'-cugcc-3', 5'-gaagc-3', 5'-ugggc-3' and 5'-agcgc-3'; preferably wherein the ribonucleotide sequence at positions 20-24 is 5'-ngavc-3'.

19. The method of embodiment 17 or 18, wherein in the sequence of the polyribonucleotide of step (a) the ribonucleotide at position 6 is g, the ribonucleotide at position 7 is a, and the ribonucleotide at position 8 is a; in particular wherein the ribonucleotide at position 9 is a.

20. The method of any one of embodiments 17-19, wherein in the sequence of the polyribonucleotide of step (a) the ribonucleotide at position 16 is u.

21. The method of any one of embodiments 17-20, wherein in the sequence of the polyribonucleotide of step (a) the ribonucleotide at position 17 is u the ribonucleotide at position 18 is g, and the ribonucleotide at position 19 is c.

22. The method of embodiment 17, wherein in the polyribonucleotide of step (a) the sequence at position 6-24 is 5'-ugaannnnnnnuucngavc-3' (SEQ ID NO: 3).

23. The method of embodiment 17, wherein in the polyribonucleotide of step (a) the sequence at position 6-24 is 5'-ugaannnnnnnuucngavc-3' (SEQ ID NO: 4).

24. The method of embodiment 23, wherein in the polyribonucleotide of step (a) the sequence at position 6-24 is 5'-ugaannnnnuucngavc-3' (SEQ ID NO: 5).

25. The method of embodiment 17, wherein in the polyribonucleotide of step (a) the sequence at position 6-24 is 5'-gaaannnnnnnuucngavc-3' (SEQ ID NO: 6), in particular 5'-gaaannnnnnuucngavc-3' (SEQ ID NO: 67), more particular 5'-gaaannnnnuucngavc-3' (SEQ ID NO: 68).

26. The method of embodiment 17, wherein the first RNA sequence of step (a) is 5'-gbucnugaannnnnnnuucnnnnn-3' (SEQ ID NO: 7), in particular wherein the first RNA sequence of step (a) is 5'-gbucnugaannnnnnnuucngavc-3' (SEQ ID NO: 8).

27. The method of embodiment 17, wherein the first RNA sequence of step (a) is 5'-gbucnugaannnnnnnnuucngavc-3' (SEQ ID NO: 9).

28. The method of embodiment 27, wherein the first RNA sequence of step (a) is 5'-gbucnugaannnnnnuuucngavc-3' (SEQ ID NO: 10).

29. The method of embodiment 17 wherein the first RNA sequence of step (a) is 5'-gbucngaaannnnnnnuucngavc-3' (SEQ ID NO: 11).

30. The method of embodiment 29, wherein the first RNA sequence of step (a) is 5'-gbucngaaannnnnnuucngavc-3' (SEQ ID NO: 69).

31. The method of embodiment 30, wherein the first RNA sequence of step (a) is 5'-gbucngaaannnnnuucngavc-3' (SEQ ID NO: 70).

32. The method of any one of embodiments 1-31, wherein the polyribonucleotide prepared in step (a) has a mono-, di-, or triphosphate or respective analogue attached to its 5' end; preferably a triphosphate.

33. The method of any one of embodiments 1-32, wherein the complementary polyribonucleotide prepared in step (b) has a mono-, di-, or triphosphate or respective analogue attached to its 5' end; preferably a triphosphate.

34. The method of embodiment 1, wherein the first RNA sequence of step (a) is

5'-guucugcaaucagcuauacguuau-3'     (SEQ ID NO: 104)
or

5'-guucugcaaucagcuaaacguuau-3'.    (SEQ ID NO: 103)

35. The method of embodiment 34, wherein the first RNA sequence of step (a) is (SEQ ID NO: 108)
3P-5'-g$_{PTO}$u$_{PTO}$ucu$_m$gcaa$_f$ucag$_f$cuauacguu$_{PTO}$a$_{PTO}$u-3'
or
                                    (SEQ ID NO: 107)
3P-5'-g$_{PTO}$u$_{PTO}$ucu$_m$gcaa$_f$ucag$_f$cuaaacguu$_{PTO}$a$_{PTO}$u-3', the nucleotide indexed m is 2'-O-methylated;

the nucleotide indexed f is 2'-fluoro;

the index PTO between two nucleotides indicates that said two nucleotides are linked by a phosphothioate bond; and 3P-5' is a 5'-triphosphate.

36. The method of embodiment 34 or 35, wherein the second RNA sequence of step (b) is fully complementary to the first RNA sequence of step (a) and is 5'-auaacguuuagcugauugcagaac-3';    (SEQ ID NO: 105)
or 5'-aaauaacguuuagcugauugcagaac-3';  (SEQ ID NO: 106)
or 5'-auaacguauagcugauugcagaac-3';    (SEQ ID NO: 115)
or 5'-aaauaacguauagcugauugcagaac-3'.  (SEQ ID NO: 116)

37. The method of embodiment 36, wherein the second RNA sequence of step (b) is (SEQ ID NO: 109)
5'-a$_{PTO}$u$_{PTO}$a$_m$acguu$_f$uagc$_f$ugauugcagaac-3'-P,
or (SEQ ID NO: 110)
5'-a$_{PTO}$u$_{PTO}$a$_m$acguu$_f$uagc$_f$ugauugcagaac-3',
or (SEQ ID NO: 111)
5'-aaa$_{PTO}$u$_{PTO}$a$_m$acguu$_f$uagc$_f$ugauugcagaac-3'-P,
or (SEQ ID NO: 112)
5'-aaa$_{PTO}$u$_{PTO}$a$_m$acguu$_f$uagc$_f$ugauugcagaac-3',
or (SEQ ID NO: 117)
5'-a$_{PTO}$u$_{PTO}$a$_m$acgua$_f$uagc$_f$ugauugcagaac-3'-P,
or (SEQ ID NO: 118)
5'-a$_{PTO}$u$_{PTO}$a$_m$acgua$_f$uagc$_f$ugauugcagaac-3',
or (SEQ ID NO: 119)
5'-aaa$_{PTO}$u$_{PTO}$a$_m$acgua$_f$uagc$_f$ugauugcagaac-3'-P,
or (SEQ ID NO: 120)
5'-aaa$_{PTO}$u$_{PTO}$a$_m$acgua$_f$uagc$_f$ugauugcagaac-3';

wherein the nucleotide indexed m is 2'-O-methylated; the nucleotide indexed f is 2'-fluoro; the index PTO between two nucleotides indicates that said two nucleotides are linked by a phosphothioate bond; and 3'-P is a 3'-monophosphate.

38. The method of embodiment 37, wherein the first RNA sequence of step (a) is 3P-5'-g$_{PTO}$u$_{PTO}$ucu$_m$gcaa$_f$ucag$_f$cuauacguu$_{PTO}$a$_{PTO}$u-3' (SEQ ID NO: 108) and the second RNA sequence of step (b) is 5'-a$_{PTO}$u$_{PTO}$a$_m$acgua$_f$uagc$_f$ugauugcagaac-3'-P (SEQ ID NO: 117).

39. The method of embodiment 37, wherein the first RNA sequence of step (a) is 3P-5'-g$_{PTO}$u$_{PTO}$ucu$_m$gcaa$_f$ucag$_f$cuauacguu$_{PTO}$a$_{PTO}$u-3' (SEQ ID NO: 108) and the second RNA sequence of step (b) is 5'-a$_{PTO}$u$_{PTO}$a$_m$acgua$_f$uagc$_f$ugauugcagaac-3' (SEQ ID NO: 118).

40. The method of embodiment 37, wherein the first RNA sequence of step (a) is 3P-5'-g$_{PTO}$u$_{PTO}$ucu$_m$gcaa$_f$ucag$_f$cuauacguu$_{PTO}$a$_{PTO}$u-3'-OH (SEQ ID NO: 108) and the second RNA sequence of step (b) is 5'-aaa$_{PTO}$u$_{PTO}$a$_m$acgua$_f$uagc$_f$ugauugcagaac-3'-P (SEQ ID NO: 119).

41. The method of embodiment 37, wherein the first RNA sequence of step (a) is 3P-5'-g$_{PTO}$u$_{PTO}$ucu$_m$gcaa$_f$ucag$_f$cuauacguu$_{PTO}$a$_{PTO}$u-3' (SEQ ID NO: 108) and the second RNA sequence of step (b) is 5'-aaa$_{PTO}$u$_{PTO}$a$_m$acgua$_f$uagc$_f$ugauugcagaac-3' (SEQ ID NO: 120).

42. The method of embodiment 37, wherein the first RNA sequence of step (a) is 3P-5'-g$_{PTO}$u$_{PTO}$ucu$_m$gcaa$_f$ucag$_f$cuaaacguu$_{PTO}$a$_{PTO}$u-3' (SEQ ID NO: 107) and the second RNA sequence of step (b) is 5'-a$_{PTO}$u$_{PTO}$a$_m$acguu$_f$uagc$_f$ugauugcagaac-3'-P (SEQ ID NO: 109).

43. The method of embodiment 37, wherein the first RNA sequence of step (a) is 3P-5'-g$_{PTO}$u$_{PTO}$ucu$_m$gcaa$_f$ucag$_f$cuaaacguu$_{PTO}$a$_{PTO}$u-3' (SEQ ID NO: 107) and the second RNA sequence of step (b) is 5'-a$_{PTO}$u$_{PTO}$a$_m$acguu$_f$uagc$_f$ugauugcagaac-3' (SEQ ID NO: 110).

44. The method of embodiment 37, wherein the first RNA sequence of step (a) is 3P-5'-g$_{PTO}$u$_{PTO}$ucu$_m$gcaa$_f$ucag$_f$cuaaacguu$_{PTO}$a$_{PTO}$u-3' (SEQ ID NO: 107) and the second RNA sequence of step (b) is 5'-aaa$_{PTO}$u$_{PTO}$a$_m$acguu$_f$uagc$_f$ugauugcagaac-3'-P (SEQ ID NO: 111).

45. The method of embodiment 37, wherein the first RNA sequence of step (a) is 3P-5'-g$_{PTO}$u$_{PTO}$ucu$_m$gcaa$_f$ucag$_f$cuaaacguu$_{PTO}$a$_{PTO}$u-3' (SEQ ID NO: 107) and the second RNA sequence of step (b) is 5'-aaa$_{PTO}$u$_{PTO}$a$_m$acguu$_f$uagc$_f$ugauugcagaac-3' (SEQ ID NO: 112).

46. A RIG-I agonist, obtainable by the method of any one of embodiments 1-45.

47. The RIG-I agonist of embodiment 46, wherein the RIG-I agonist is a polyribonucleotide which comprises at least one synthetic or modified internucleoside linkage such as phosphodiester, phosphorothioate, N3 phosphoramidate, boranophosphate, 2,5-phosphodiester, amide-linked, phosphonoacetate (PACE), morpholino, peptide nucleic acid (PNA), or a mixture thereof, provided the linkage(s) do not compromise the type I IFN-inducing activity of the polyribonucleotide, preferably wherein the polyribonucleotide comprises phosphorothioate linkage(s) and/or pyrophosphate linkage(s).

48. The RIG-I agonist of embodiment 46 or 47, wherein the RIG-I agonist is a polyribonucleotide which comprises at least one modified nucleotide selected from pseudouridine, 2-thiouridine, 2'-fluorine-dNTP, 2'-O-methylated NTP, in particular 2'-fluorine-dCTP, 2'-fluorine-dUTP, 2'-O-methylated CTP, and 2'-O-methylated UTP.

49. The RIG-I agonist of any of embodiments 46-48, wherein the first RNA sequence is 5'-guucugcaaucagcuauacguuau-3' (SEQ ID NO: 104) or 5'-guucugcaaucagcuaaacguuau-3' (SEQ ID NO: 103).

50. The RIG-I agonist of embodiment 49, wherein the first RNA sequence is (SEQ ID NO: 108)
3P-5'-g$_{PTO}$u$_{PTO}$ucu$_m$gcaa$_f$ucag$_f$cuauacguu$_{PTO}$a$_{PTO}$u-3'
or (SEQ ID NO: 107)
3P-5'-g$_{PTO}$u$_{PTO}$ucu$_m$gcaa$_f$ucag$_f$cuaaacguu$_{PTO}$a$_{PTO}$u-3', the nucleotide indexed m is 2'-O-methylated;

the nucleotide indexed f is 2'-fluoro;

the index PTO between two nucleotides indicates that said two nucleotides are linked by a phosphothioate bond; and 3P-5' is a 5'-triphosphate.

51. The RIG-I agonist of embodiment 49 or 50, wherein the second RNA sequence is fully complementary to the first RNA sequence of step (a) and is (SEQ ID NO: 105)
5'-auaacguuuagcugauugcagaac-3';
or (SEQ ID NO: 106)
5'-aaauaacguuuagcugauugcagaac-3';
or (SEQ ID NO: 115)
5'-auaacguauagcugauugcagaac-3';
or (SEQ ID NO: 116)
5'-aaauaacguauagcugauugcagaac-3'.

52. The RIG-I agonist of embodiment 51, wherein the second RNA sequence is

5'-a$_{PTO}$u$_{PTO}$a$_m$acguu$_f$uagc$_f$ugauugcagaac-3'-P, (SEQ ID NO: 109)
or 5'-a$_{PTO}$u$_{PTO}$a$_m$acguu$_f$uagc$_f$ugauugcagaac-3', (SEQ ID NO: 110)
or 5'-aaa$_{PTO}$u$_{PTO}$a$_m$acguu$_f$uagc$_f$ugauugcagaac-3'-P, (SEQ ID NO: 111)
or 5'-aaa$_{PTO}$u$_{PTO}$a$_m$acguu$_f$uagc$_f$ugauugcagaac-3', (SEQ ID NO: 112)
or 5'-a$_{PTO}$u$_{PTO}$a$_m$acgua$_f$uagc$_f$ugauugcagaac-3'-P, (SEQ ID NO: 117)
or 5'-a$_{PTO}$u$_{PTO}$a$_m$acgua$_f$uagc$_f$ugauugcagaac-3', (SEQ ID NO: 118)
or 5'-aaa$_{PTO}$u$_{PTO}$a$_m$acgua$_f$uagc$_f$ugauugcagaac-3'-P, (SEQ ID NO: 119)
or 5'-aaa$_{PTO}$u$_{PTO}$a$_m$acgua$_f$uagc$_f$ugauugcagaac-3'; (SEQ ID NO: 120)

wherein the nucleotide indexed m is 2'-O-methylated; the nucleotide indexed f is 2'-fluoro; the index PTO between two nucleotides indicates that said two nucleotides are linked by a phosphothioate bond; and 3'-P is a 3'-monophosphate.

53. The RIG-I agonist of embodiment 52, wherein the first RNA sequence is 3P-5'-g$_{PTO}$u$_{PTO}$ucu$_m$gcaa$_f$ucag$_f$cuauacguu$_{PTO}$a$_{PTO}$u-3' (SEQ ID NO: 108) and the second RNA sequence is 5'-a$_{PTO}$u$_{PTO}$a$_m$acgua$_f$uagc$_f$u-gauugcagaac-3'-P (SEQ ID NO: 117).

54. The RIG-I agonist of embodiment 52, wherein the first RNA sequence is 3P-5'-g$_{PTO}$u$_{PTO}$ucu$_m$gcaa$_f$ucag$_f$cuauacguu$_{PTO}$a$_{PTO}$u-3' (SEQ ID NO: 108) and the second RNA sequence is 5'-a$_{PTO}$u$_{PTO}$a$_m$acgua$_f$uagc$_f$u-gauugcagaac-3' (SEQ ID NO: 118).

55. The RIG-I agonist of embodiment 52, wherein the first RNA sequence is 3P-5'-g$_{PTO}$u$_{PTO}$ucu$_m$gcaa$_f$ucag$_f$cuauacguu$_{PTO}$a$_{PTO}$u-3' (SEQ ID NO: 108) and the second RNA sequence is 5'-aaa$_{PTO}$u$_{PTO}$a$_m$acgua$_f$uagc$_f$u-gauugcagaac-3'-P (SEQ ID NO: 119).

56. The RIG-I agonist of embodiment 52, wherein the first RNA sequence is 3P-5'-g$_{PTO}$u$_{PTO}$ucu$_m$gcaa$_f$ucag$_f$cuauacguu$_{PTO}$a$_{PTO}$u-3' (SEQ ID NO: 108) and the second RNA sequence is 5'-aaa$_{PTO}$u$_{PTO}$a$_m$acgua$_f$uagc$_f$u-gauugcagaac-3' SEQ ID NO: 120.

57. The RIG-I agonist of embodiment 52, wherein the first RNA sequence is 3P-5'-g$_{PTO}$u$_{PTO}$ucu$_m$gcaa$_f$ucag$_f$cuaaacguu$_{PTO}$a$_{PTO}$u-3' (SEQ ID NO: 107) and the second RNA sequence is 5'-a$_{PTO}$u$_{PTO}$a$_m$acguu$_f$uagc$_f$u-gauugcagaac-3'-P (SEQ ID NO: 109).

58. The method of embodiment 52, wherein the first RNA sequence is 3P-5'-g$_{PTO}$u$_{PTO}$ucu$_m$gcaa$_f$ucag$_f$cuaaacguu$_{PTO}$a$_{PTO}$u-3' (SEQ ID NO: 107) and the second RNA sequence is 5'-aaa$_{PTO}$u$_{PTO}$a$_m$acguu$_f$uagc$_f$u-gauugcagaac-3'-P (SEQ ID NO: 110).

59. The RIG-I agonist of embodiment 52, wherein the first RNA sequence is 3P-5'-g$_{PTO}$u$_{PTO}$ucu$_m$gcaa$_f$ucag$_f$cuaaacguu$_{PTO}$a$_{PTO}$u-3' (SEQ ID NO: 107) and the second RNA sequence is 5'-aaa$_{PTO}$u$_{PTO}$a$_m$acguu$_f$uagc$_f$u-gauugcagaac-3' (SEQ ID NO: 111).

60. The RIG-I agonist of embodiment 52, wherein the first RNA sequence is 3P-5'-g$_{PTO}$u$_{PTO}$ucu$_m$gcaa$_f$ucag$_f$cuaaacguu$_{PTO}$a$_{PTO}$u-3' (SEQ ID NO: 107) and the second RNA sequence is 5'-aaa$_{PTO}$u$_{PTO}$a$_m$acguu$_f$uagc$_f$u-gauugcagaac-3' (SEQ ID NO: 112).

61. The RIG-I agonist of any of embodiments 46-48, wherein the polyribonucleotide comprises at least one inosine.

62. A RIG-I agonist, wherein
(I) the first RNA sequence is 3P-5'-g$_{PTO}$u$_{PTO}$ucu$_m$gcaa$_f$ucag$_f$cuauacguu$_{PTO}$a$_{PTO}$u-3' (SEQ ID NO: 108) and the second RNA sequence is 5'-a$_{PTO}$u$_{PTO}$a$_m$acgua$_f$uagc$_f$u-gauugcagaac-3'-P (SEQ ID NO: 117); or
(II) the first RNA sequence is 3P-5'-g$_{PTO}$u$_{PTO}$ucu$_m$gcaa$_f$ucag$_f$cuauacguu$_{PTO}$a$_{PTO}$u-3' (SEQ ID NO: 108) and the second RNA sequence is 5'-a$_{PTO}$u$_{PTO}$a$_m$acgua$_f$uagc$_f$u-gauugcagaac-3' (SEQ ID NO: 118); or
(III) the first RNA sequence is 3P-5'-g$_{PTO}$u$_{PTO}$ucu$_m$gcaa$_f$ucag$_f$cuauacguu$_{PTO}$a$_{PTO}$u-3' (SEQ ID NO: 108) and the second RNA sequence is 5'-aaa$_{PTO}$u$_{PTO}$a$_m$acgua$_f$uagc$_f$ugauugcagaac-3'-P (SEQ ID NO: 119); or
(IV) the first RNA sequence is 3P-5'-g$_{PTO}$u$_{PTO}$ucu$_m$gcaa$_f$ucag$_f$cuauacguu$_{PTO}$a$_{PTO}$u-3' (SEQ ID NO: 108) and the second RNA sequence is 5'-aaa$_{PTO}$u$_{PTO}$a$_m$acgua$_f$uagc$_f$ugauugcagaac-3' (SEQ ID NO: 120); or
(V) the first RNA sequence is 3P-5'-g$_{PTO}$u$_{PTO}$ucu$_m$gcaa$_f$ucag$_f$cuaaacguu$_{PTO}$a$_{PTO}$u-3' (SEQ ID NO: 107) and the second RNA sequence is 5'-a$_{PTO}$u$_{PTO}$a$_m$acguu$_f$uagc$_f$u-gauugcagaac-3'-P (SEQ ID NO: 109); or
(VI) the first RNA sequence is 3P-5'-g$_{PTO}$u$_{PTO}$ucu$_m$gcaa$_f$ucag$_f$cuaaacguu$_{PTO}$a$_{PTO}$u-3' (SEQ ID NO: 107) and the second RNA sequence is 5'-a$_{PTO}$u$_{PTO}$a$_m$acguu$_f$uagc$_f$u-gauugcagaac-3' (SEQ ID NO: 110); or
(VII) the first RNA sequence is 3P-5'-g$_{PTO}$u$_{PTO}$ucu$_m$gcaa$_f$ucag$_f$cuaaacguu$_{PTO}$a$_{PTO}$u-3' (SEQ ID NO: 107) and the second RNA sequence is 5'-aaa$_{PTO}$u$_{PTO}$a$_m$acguu$_f$uagc$_f$ugauugcagaac-3'-P (SEQ ID NO: 111); or
(VIII) the first RNA sequence is 3P-5'-g$_{PTO}$u$_{PTO}$ucu$_m$gcaa$_f$ucag$_f$cuaaacguu$_{PTO}$a$_{PTO}$u-3' (SEQ ID NO: 107) and the second RNA sequence is 5'-aaa$_{PTO}$u$_{PTO}$a$_m$acguu$_f$uagc$_f$ugauugcagaac-3' (SEQ ID NO: 112).

63. A pharmaceutical composition comprising at least one RIG-I agonist of any one of embodiments 46-62, and a pharmaceutically acceptable carrier.

64. The pharmaceutical composition of embodiment 63, further comprising at least one agent selected from an anti-tumor agent, an immunostimulatory agent, an anti-viral agent, an anti-bacterial agent, a checkpoint-inhibitor, retinoic acid, IFN-α, and IFN-β.

65. The pharmaceutical composition of embodiment 63, wherein said composition is a vaccine composition.

66. A RIG-I agonist according to any one of embodiments 46-62, or a pharmaceutical composition according to any one of embodiment 63-65 for use in medicine.

67. A RIG-I agonist according to any one of embodiments 46-62, or a pharmaceutical composition according to any one of embodiment 63-65, for use in preventing and/or treating a disease or condition selected from a tumor, an infection, an allergic condition, and an immune disorder.

68. The pharmaceutical composition for use of embodiment 67, wherein the composition is prepared for administration in combination with at least one treatment selected from a prophylactic and/or a therapeutic treatment of a tumor, an infection, an allergic condition, and an immune disorder.

69. A RIG-I agonist according to any one of embodiments 46-62, or a pharmaceutical composition according to any one of embodiment 63-65, for use as a vaccine adjuvant.
70. An ex vivo method for inducing type I IFN production in a cell, comprising the step of contacting a cell expressing RIG-I with at least one RIG-I agonist according to any one of embodiments 46-62, optionally in mixture with a complexation agent.

The present invention is also illustrated by the Figures and following Examples. The Figures and Examples are for illustration purposes only and are by no means to be construed to limit the scope of the invention.

EXAMPLES

Figure 1:
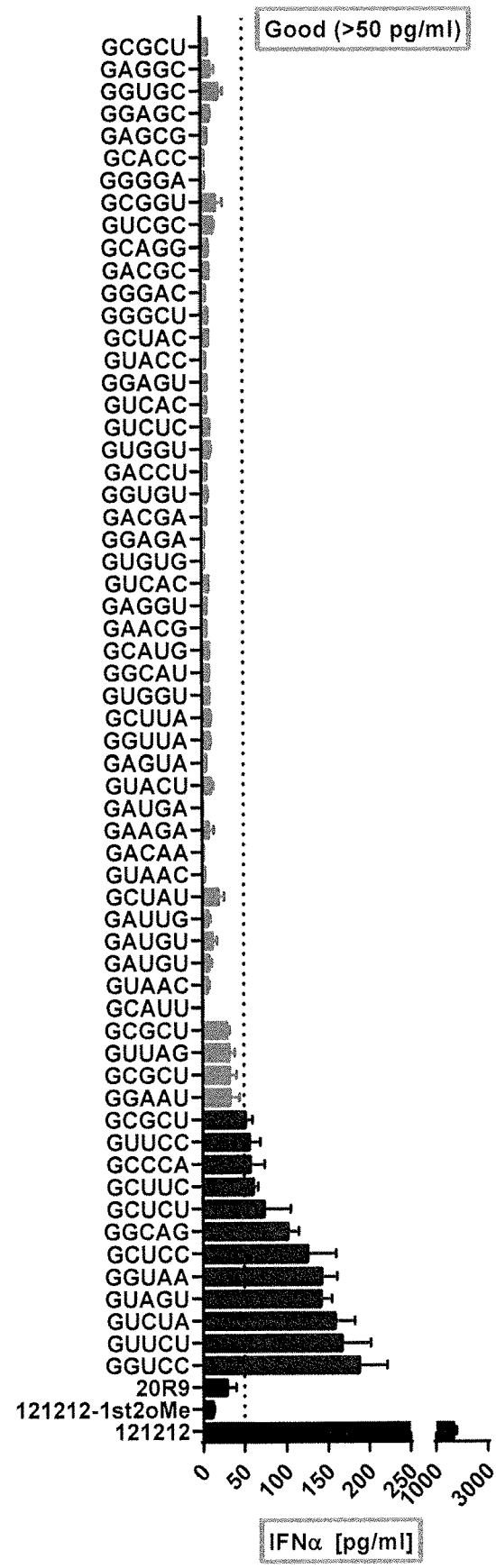
FIG. 1: Screening selected 5-mer sequences fused a 19-mer tail sequence (UGGAUGGUUGGCUAGGAUA) for IFNα induction in PBMCs.

Material and Methods
Cell Culture

The human airway epithelial cell line A549 and the human HPV16+ cervix epithelial cell line CaSki were both obtained from Cell Lines Services (Germany). A549-PGK-EGFP cells were generated at Cellomics Technology, LLC (Halethorpe, Md., USA). Human primary peripheral blood mononuclear cells (PBMCs) were isolated from fresh buffy coats obtained from healthy volunteers according to standard protocols (Schuberth-Wagner et al., 2015, Immunity). PBMCs ($2.6 \times 10^6$ cells/ml) were seeded in 96-well plates and maintained in RPMI1640 supplemented with 10% FCS, 1.5 mM L-glutamine and 1× penicillin/streptomycin. In some experiments, PBMCs were pre-treated with 2.5 mg/ml chloroquine (Sigma Aldrich) for at least 1 hr to prevent endosomal TLR activation. All cell culture reagents were obtained from Gibco.

Cell Stimulation

Chemically synthesized RNA oligonucleotides were purchased from Biomers (Ulm, Germany) and Axolabs (Kulmbach, Germany). RNA was transfected into cells using Lipofectamine 2000 according to manufacturers instructions (Invitrogen). PBMCs were stimulated once and conditioned medium was collected after 17 hrs. CaSki cells were stimulated once or twice depending on the duration of the experiment (3 or 6d). For the long term experiment (6d), CaSki cells were treated on d0 and d3.

Flowcytometric Quantitation of Intracellular EGFP

FACS-based quantitation of intracellular EGFP levels was performed according to standard protocols. Briefly, after stimulation for the indicated time points, A549-PGK-EGFP cells were collected, resuspended in PBS and subjected to flowcytometric analysis. Changes in fluorescence signals were measured using an Attune NxT acoustic focusing cytometer (Life Technologies).

XTT Assay To monitor changes of the cellular metabolic activity, the XTT assay was used according to the manufacturers instructions (Roche).

Real-Time RT-PCR

Steady state mRNA levels of HPV16E7 and IFNβ were quantified by real-time fluorescence detection using SYBR Select Master Mix (Life Technologies). Reactions in duplicate were analyzed in a Quant Studio 6 flex (Life Technologies). Specific primer pairs were as follows: HPV16E7 forward, 5'-AGTGTGACTCTACGCTTCGG-3 (SEQ ID NO: 30) and reverse, 5'-TGTGCCCATTAACAGGTCTT-3 (SEQ ID NO: 31), hIFNβ forward 5'-GT-CACTGTGCCTGGACCATA-3' (SEQ ID NO: 32) and reverse, 5'-AGAGGCACAGGCTAGGAGAT-3 (SEQ ID NO: 33), and hβ-Actin forward 5'-GA-GACCGCGTCCGCC-3 (SEQ ID NO: 34) and reverse, 5'-ATCATCCATGGTGAGCTGGC-3 (SEQ ID NO: 35).

IFNα ELISA

Conditioned cell culture supernatant derived from activated PBMCs was harvested at 17 hrs time point. Quantitation of IFNα levels in cell culture supernatant was performed using the human IFN alpha matched antibody pairs ELISA (eBioscience, San Diego, Calif., USA).

Example 1-5'-Sequences Influence on Immune Activation

Nucleic acid sensors efficiently trigger anti-viral and anti-cancer immune pathways to strengthen the body's defense mechanisms. Pharmacological activation of nucleic acid sensors such as TLRs and RIG-I emerged them as attractive targets to recover host homeostasis (Junt and Barchet, 2015, Nat Rev Immunol). Recent studies highlight structural features determining RIG-I activation: the phosphorylation status at the very 5' end (Schlee et al, Goubau et al), the oligonucleotide length (Schlee) and the 5' nucleotide (Schlee).

Structural determinants distinguishing strong from weak RIG-I ligands remain largely elusive and thus we aimed to analyze the influence of different 5-mer sequences at the very 5'-end sensed by RIG-I's basic patch region. Therefore, sixty 5-mer sequences with a G/C content ranging from 40-80% were generated randomly Subsequently, all 5-mer sequences were linked to a 19-mer random tail (5'-UG-GAUGGUUGGCUAGGAUA-3' (SEQ ID NO: 28)) constituting the 24-mer sense strand. The complementary antisense strand had a 5' two nucleotide overhang to allow directed recognition of the random 5-mer sequences through RIG-I. Screening revealed that only 12 out of 60 RIG-I ligands induced good IFNα release (threshold 50 pg/ml) from primary human PBMCs (FIG. 1, dark grey bars). Moreover, the effect appeared to be independent of the G/C content (FIG. 1). Comparative analysis of all 12 good 5-mer sequences showed that certain nucleotides at particular positions were preferred and a consensus motif for the 5-mer sequence (5'-$G_1$-no$A_2$-$U_3$-$C_4$-$N_5$-3') was elaborated:

| 5-mer sequences | | | | |
|---|---|---|---|---|
| G | G | U | C | C |
| G | U | U | C | U |
| G | U | C | U | A |
| G | U | A | G | U |
| G | G | U | A | A |
| G | C | U | C | C |
| G | G | C | A | G |
| G | C | U | C | U |
| G | C | U | U | C |
| G | C | C | C | A |
| G | U | U | C | C |
| G | C | G | C | U |
| Consensus | | | | |
| G | no A | U | C | N |

Of note, 41% of all 12 good 5-mer sequences were completely covered by the 5-mer consensus motif, whereas none of the weak 5-mer sequences contained this motif (FIG. 1).

Figure 2:
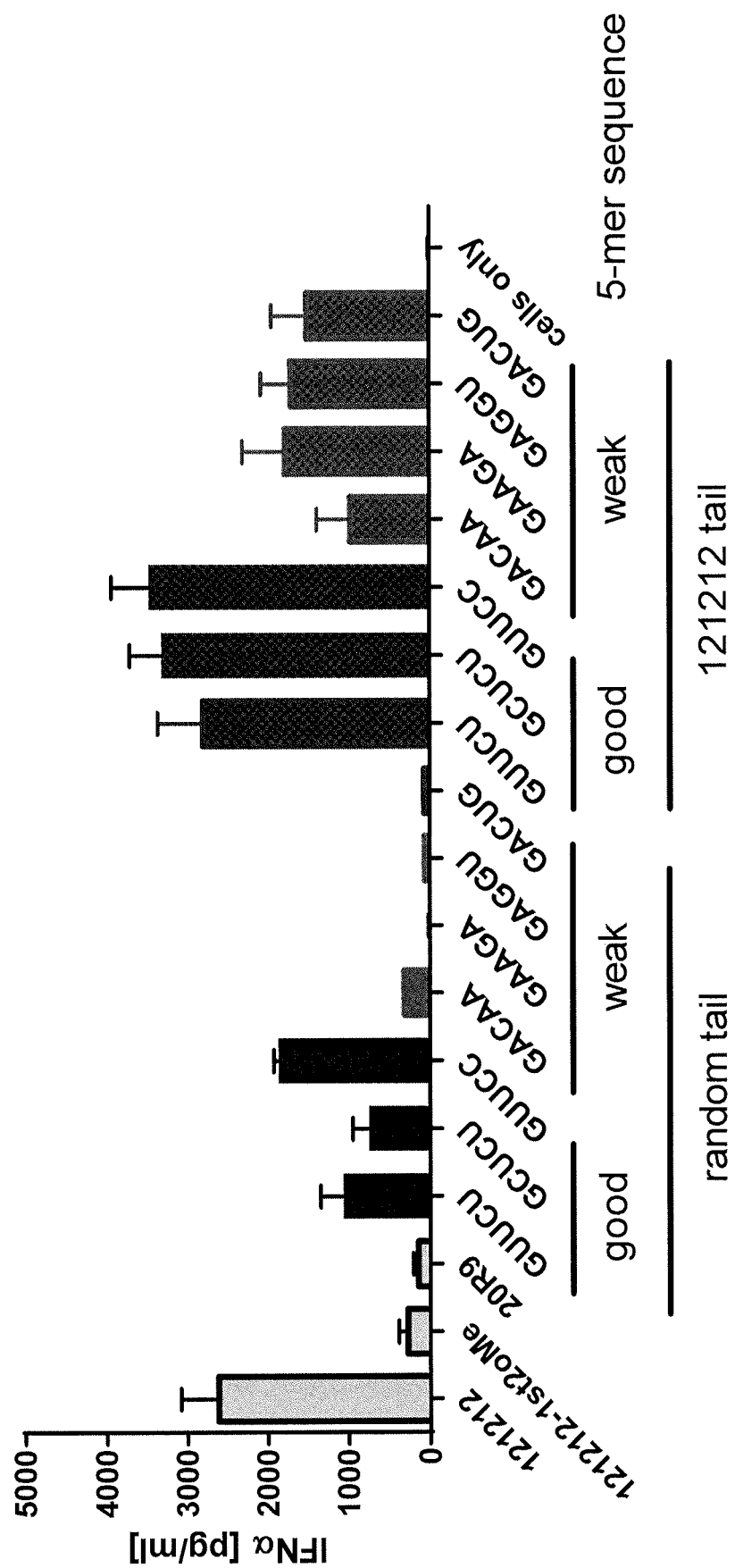
FIG. 2: Confirmation of suitability of 5-mer design in 2 independent 19-mer tail sequences (random: UGGAUG-GUUGGCUAGGAUA (SEQ ID NO: 28); 121212 tail: UGACCCUGAAGUUCAUCUU (SEQ ID NO: 29)).

To further substantiate our findings we linked both strong and weak 5-mer sequences to a set of independent 19-mer tail sequences (5'-UGACCCUGAAGUUCAUCUU-3' (SEQ ID NO: 36), 5'-UGACCCUGAAGUUCAUCU-3' (SEQ ID NO: 37), 5'-UCAAGGUGAACUUCAAGAU-3' (SEQ ID NO: 38), 5'-GGCUACGUCCAGGAGCGCA-3' (SEQ ID NO: 39)) and analyzed IFNα release from PBMCs. Indeed, we validated our previous findings and showed that 5-mer sequences considered as good were superior to those considered as weak in different 19-mer tail settings (FIGS. 2, 6B/C and 7B). Together, our data clearly demonstrated optimization of the 5' 5-mer sequence can promote RIG-I-mediated immune activation.

Figure 3:
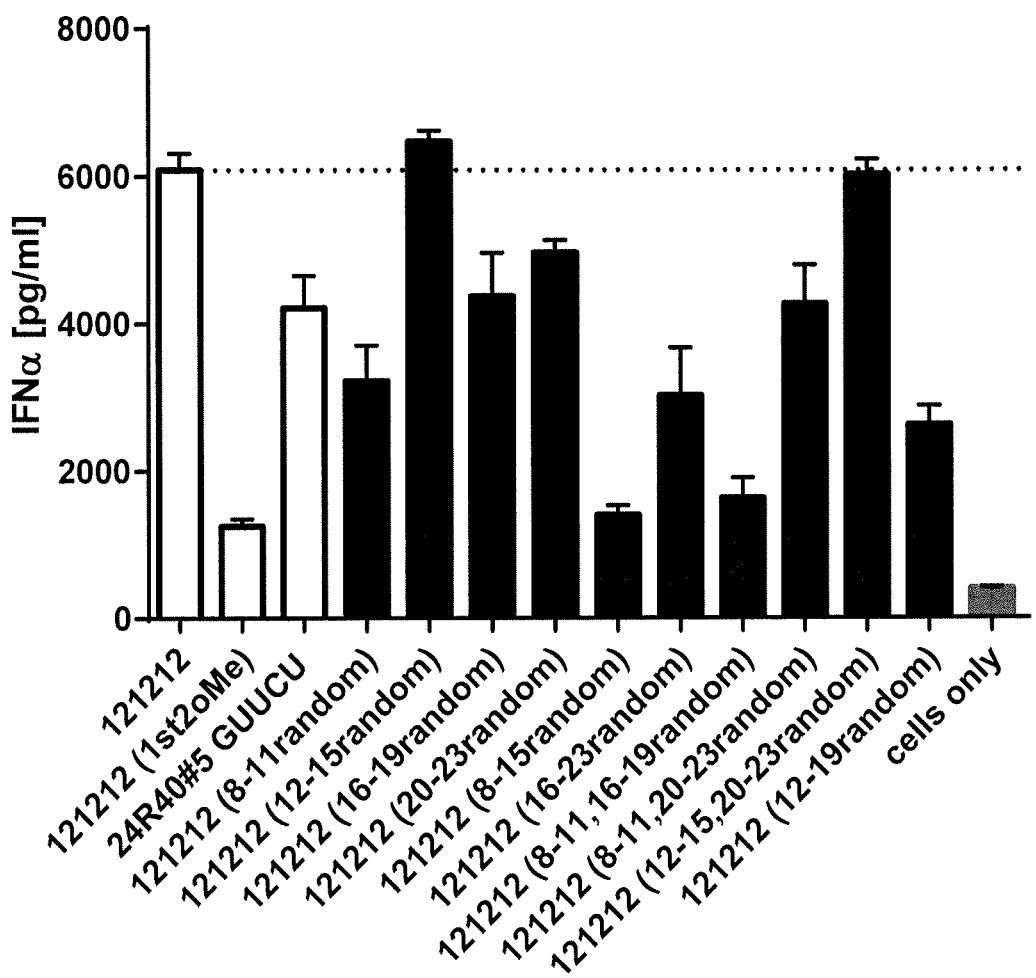
FIG. 3: Permutation of the 121212 tail (UGACC-CUGAAGUUCAUCUU (SEQ ID NO: 29)) by introducing 4-mer sequences from a random tail (UGGAUGGUUGGC-UAGGAUA (SEQ ID NO: 28)) as indicated in (A) and screening for IFNα induction (B).
Figure 4:
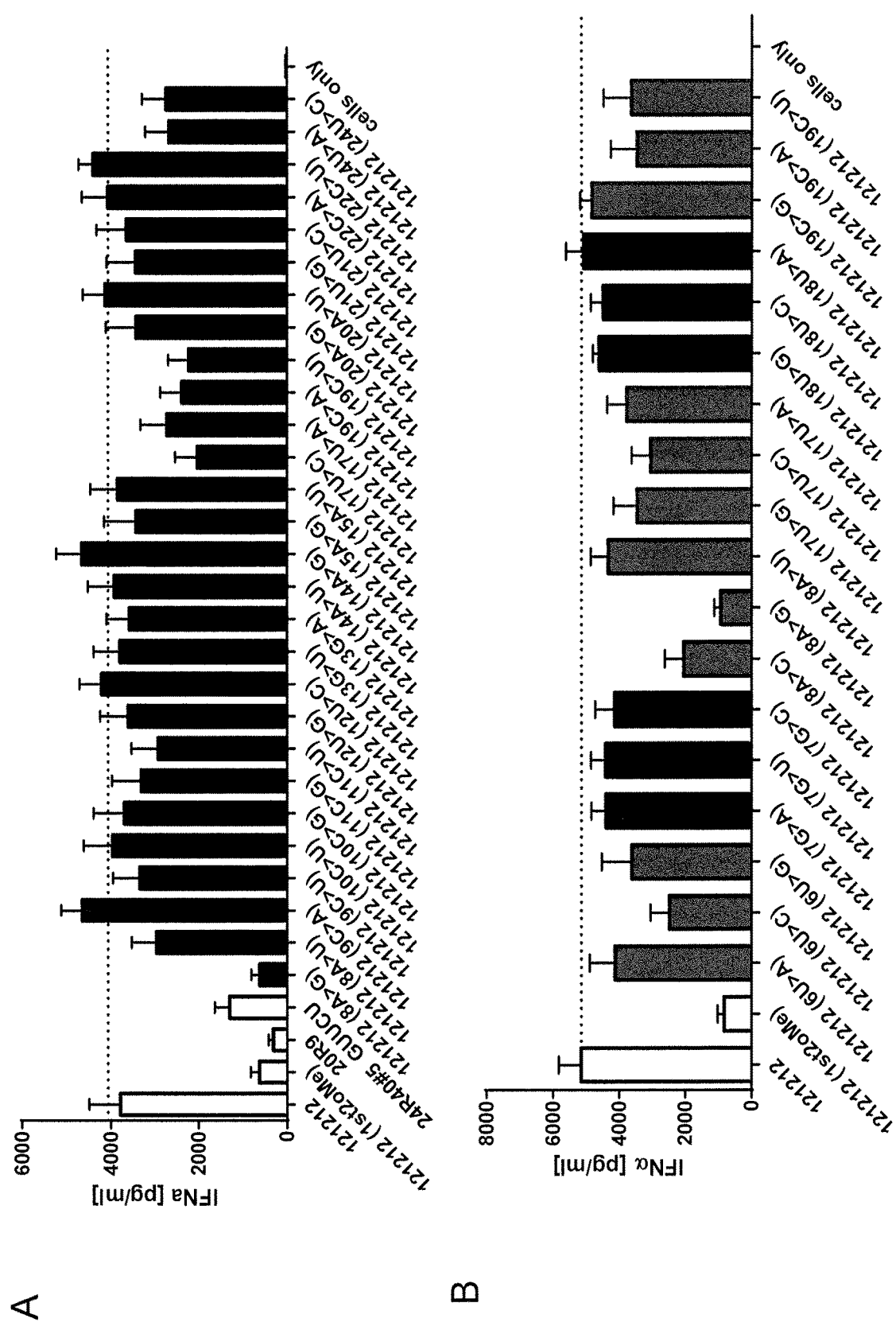
FIG. 4: Permutation of single nucleotides within the 121212 tail sequence (UGACCCUGAAGUUCAUCUU (SEQ ID NO: 29)) and screening for IFNα induction (A) and comprehensive analysis of the role of position 6-8 and positions 17-19 for IFNα induction (B).
Figure 5:
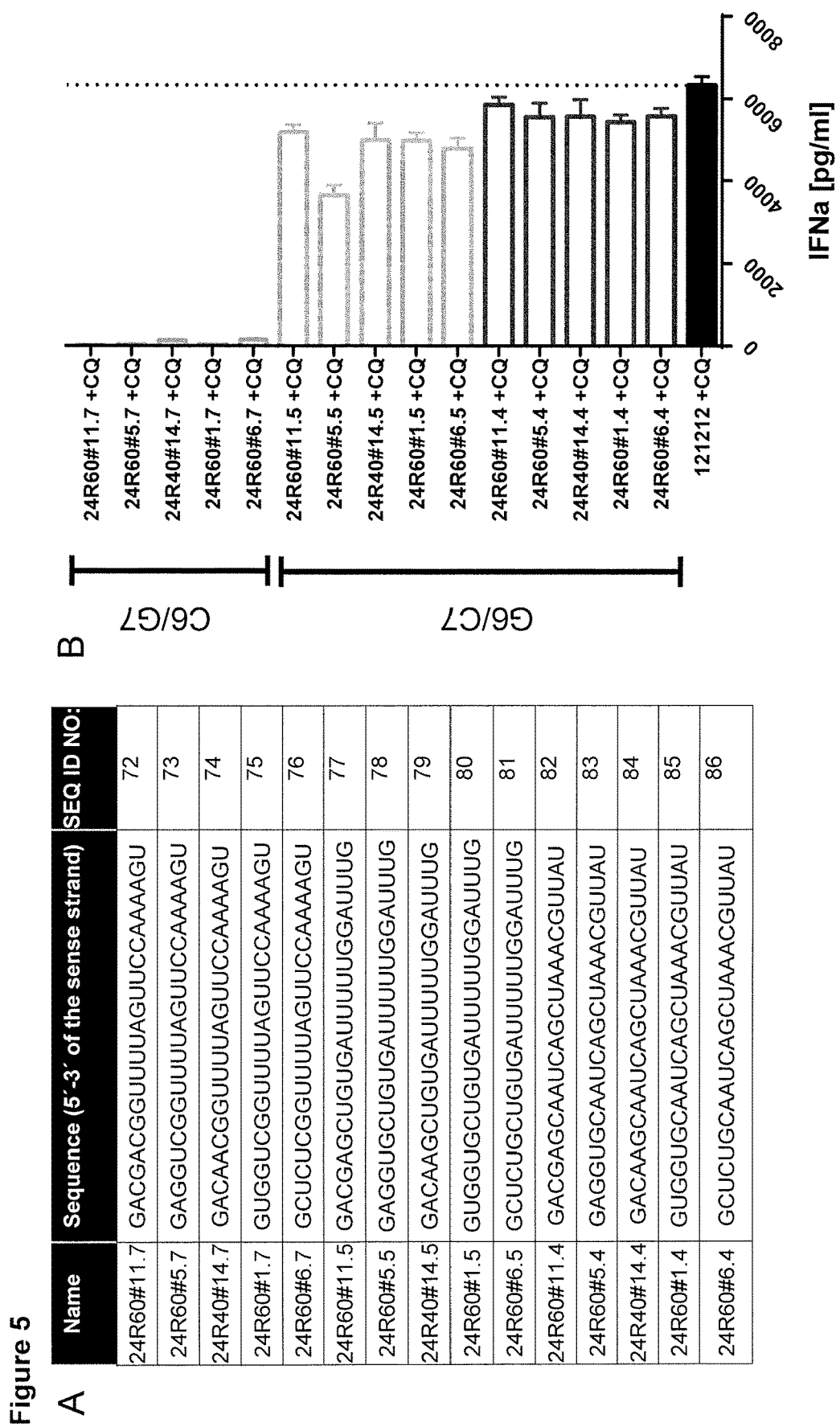
FIG. 5: Analyzing the role of a G/C or C/G doublet at position 6/7.

Example 2—Functional Boxes Reside within the Tail Sequence and Regulate Immune Activation The role of tail sequence inherent features had not been investigated as of yet. Thus, to explore whether functional structural elements within 19-mer tail sequence exist and how these might shape the immune response, the 121212 tail sequence was modified stepwise. Single or more 4-mer sequences were substituted by corresponding 4-mer cassettes derived from the random tail (5'-UGGAUG-GUUGGCUAGGAUA-3' (SEQ ID NO: 28)) (FIG. 3A). Analysis of these novel dsRNA sequences revealed that 4-mer substitutions at positions 8-11, 16-19, 20-23, 8-15, 16-23, 8-11/16-19, 8-11/20-23 and 12-19 (counted from the very 5' end of the RNA included the 5-mer sequence) are detrimental and negatively regulate RIG-I-induced IFNα release (FIG. 3B). We then set out to narrow down crucial sequence sections by changing single nucleotides within the 19-mer 121212 tail. In particular, nucleotide substitutions at the positions 6, 8, 17 and 19 within the 5'-GACGC UGACC-CUGAAGUUCAUCUU-3' (SEQ ID NO: 40) led to reduced IFNα induction (FIGS. 4A and B). Moreover, substitution of "u" at position 6 of 121212 for a "c" (final RNA sequence: 5'-GACGC CGACCCUGAAGUUCAUCUU-3' (SEQ ID NO: 71)) reduced IFNα induction by app. 50% as compared to the parent 121212 (FIG. 4B), indicating detrimental effects of $c_6/g_7$ doublets. This is further supported by data shown in FIG. 5, as a set of different dsRNAs having a c/g doublet at position 6/7 showed no up-regulation of IFNα. However, g6/c7 doublets do not compromise the IFNα induction (FIG. 5).

An adenosine at position 9 elevates the IFNα response (FIG. 4A). Together, sequence specific properties determine the agonist's inherent potential to promote inflammation.

Figure 6:
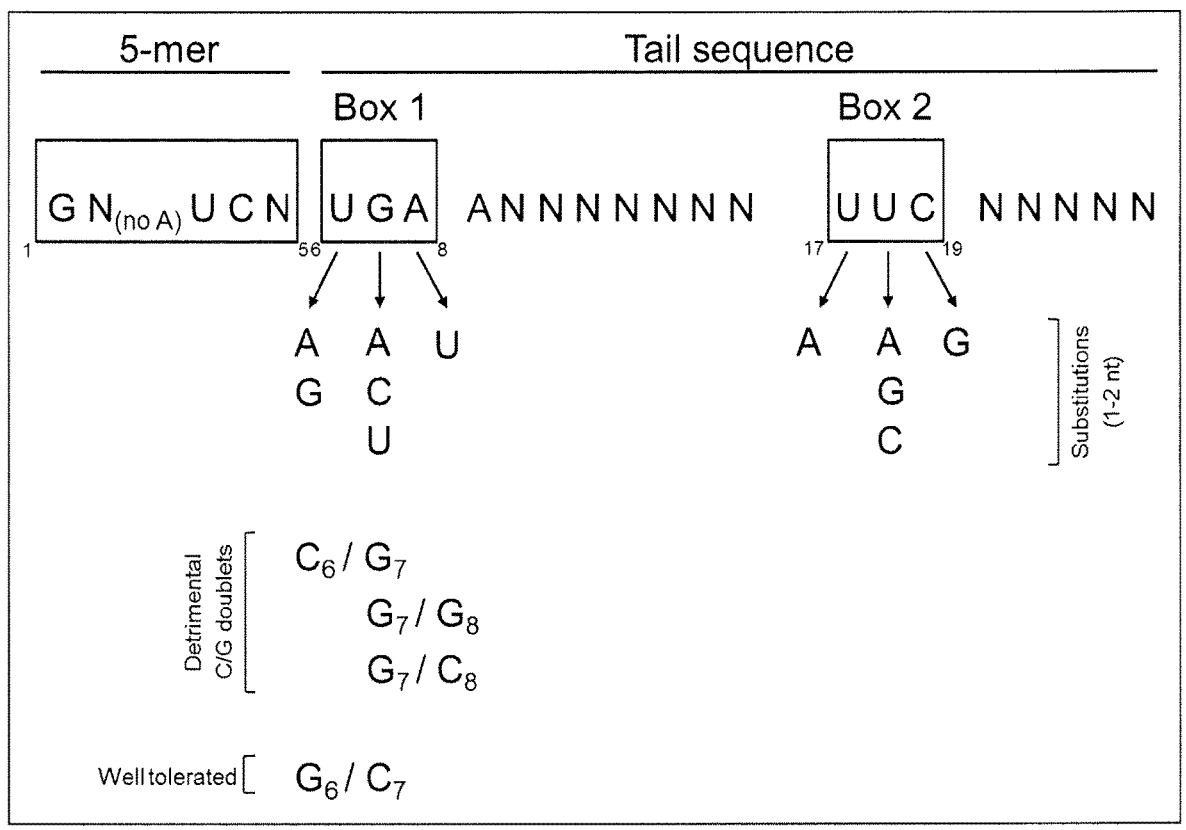
FIG. 6: Schematic overview of structural features required for optimal RIG-I agonism and detrimental sequence pattern.

Example 3—Combining Structural Features to Create a Design Rule for Optimal RIG-I Agonism Intense studies on optimal 5' 5-mer sequences and intramolecular nucleotide substitutions revealed important structural elements accounting for RIG-I agonism as described above. All elements identified were applied to a 24-mer sequence as shown in FIG. 6. The very 5' consensus 5-mer sequence is shown in the very left box. Regions 6-8 and 17-19 were assigned as box 1 (middle) and box 2 (very right), respectively and accepted nucleotide substituents with minor effects on immune stimulation are shown below. Moreover, detrimental nucleotide doublets in box 1 and their exact positions are indicated. Furthermore, adenosine at position 9 is highlighted (FIG. 6).

Here we presented the development of a novel design rule to predict highly versatile RIG-I-ligands. We identified a consensus 5-mer cassette (5'-$G_1$-no$A_2$-$U_3$-$C_4$-$N_5$-3') and a 19-mer tail sequence comprising two 3-nt boxes located at positions 6-8 (box 1) and 17-19 (box 2) within a 24-mer oligonucleotide backbone counted from the 5' end of the sense strand. Moreover, we revealed nucleotide doublets within box 1 that are detrimental and strongly counteract RIG-I-induced immunity.

Example 4—Assessment of Polyribonucleotides Obtained by the Design Rule of the Present Disclosure The following polyribonucleotides were designed following the design rule for RIG-I agonists of the present disclosure:

| Oligo-nucleotides | | Sequence (5'-3') | SEQ ID NO |
|---|---|---|---|
| 1 | Sense | 3P-$g_{PTO}u_{PTO}$ucu$_m$gcaa$_f$ucag$_f$cuaaacguu$_{PTO}a_{PTO}$u | 107 |
| | Antisense | $a_{PTO}u_{PTO}a_m$acguu$_f$uagc$_f$ugauugcagaac-P | 109 |
| 2 | Sense | 3P-$g_{PTO}u_{PTO}$ucu$_m$gcaa$_f$ucag$_f$cuaaacguu$_{PTO}a_{PTO}$u | 107 |
| | Antisense | $a_{PTO}u_{PTO}a_m$acguu$_f$uagc$_f$ugauugcagaac | 110 |

-continued

| Oligo-nucleotides | | Sequence (5'-3') | SEQ ID NO |
|---|---|---|---|
| 3 | Sense | 3P-g$_{PTO}$u$_{PTO}$ucu$_m$gcaa$_f$ucag$_f$cuaaacguu$_{PTO}$a$_{PTO}$u | 107 |
|   | Antisense | aaa$_{PTO}$u$_{PTO}$a$_m$acguu$_f$uagc$_f$ugauugcagaac-P | 111 |
| 4 | Sense | 3P-g$_{PTO}$u$_{PTO}$ucu$_m$gcaa$_f$ucag$_f$cuaaacguu$_{PTO}$a$_{PTO}$u | 107 |
|   | Antisense | aaa$_{PTO}$u$_{PTO}$a$_m$acguu$_f$uagc$_f$ugauugcagaac | 112 |
| 5 | Sense | 3P-g$_{PTO}$u$_{PTO}$ucu$_m$gcaa$_f$ucag$_f$cuauacguu$_{PTO}$a$_{PTO}$u | 108 |
|   | Antisense | a$_{PTO}$u$_{PTO}$a$_m$acguu$_f$uagc$_f$ugauugcagaac-P | 109 |
| 6 | Sense | 3P-g$_{PTO}$u$_{PTO}$ucu$_m$gcaa$_f$ucag$_f$cuauacguu$_{PTO}$a$_{PTO}$u | 108 |
|   | Antisense | a$_{PTO}$u$_{PTO}$a$_m$acguu$_f$uagc$_f$ugauugcagaac | 110 |
| 7 | Sense | 3P-g$_{PTO}$u$_{PTO}$ucu$_m$gcaa$_f$ucag$_f$cuauacguu$_{PTO}$a$_{PTO}$u | 108 |
|   | Antisense | aaa$_{PTO}$u$_{PTO}$a$_m$acguu$_f$uagc$_f$ugauugcagaac-P | 111 |
| 8 | Sense | 3P-g$_{PTO}$u$_{PTO}$ucu$_m$gcaa$_f$ucag$_f$cuauacguu$_{PTO}$a$_{PTO}$u | 108 |
|   | Antisense | aaa$_{PTO}$u$_{PTO}$a$_m$acguu$_f$uagc$_f$ugauugcagaac | 112 | the nucleotide indexed m is 2'-O-methylated;
the nucleotide indexed f is 2'-fluoro;
the index PTO between two nucleotides indicates that said two nucleotides are linked by a phosphothioate bond;
—P is a 3'-monophosphate;
3P— is a 5'triphosphate; and
—OH is a 3'-OH.

In certain assays, the following prior art RIG-I agonist (WO 2014/049079 A1) was used for comparison

| | | Sequence (5'-3) | SEQ ID NO |
|---|---|---|---|
| 3P-GFP2 1S2F | Sense | 3P-gacgcug$_f$acccugaa$_m$guucauc$_{PTO}$(u$_f$)$_{PTO}$u | 113 |
|   | Antisense | a$_{PTO}$a$_{PTO}$gaugaacuuc$_f$agggucagcg$_m$uc | 114 | the nucleotide indexed m is 2'-O-methylated;
the nucleotide indexed f is 2'-fluoro;
the index PTO between two nucleotides indicates that said two nucleotides are linked by a phosphothioate bond; and
3P— is a 5'triphosphate.

Metabolic Activity in Human Tumor Cells

The human adenocarcinoma cell line HT29 was obtained from Cell Lines Services (Germany), and the human melanoma cell line D04mel is available through the Australasian Biospecimen Network (Oncology) Cell Line Bank at the QIMR Berghofer Medical Research Institute. Human tumor cell lines D04 and HT29 were seeded at a density of $1\times10^4$ cells per well of a 96-well plate. Chemically synthesized RNA oligonucleotides were purchased from Biomers (Ulm, Germany), Axolabs (Kulmbach, Germany) or were produced internally. RNA was transfected into the cells using Lipofectamine 2000 according to manufacturer's instructions (Invitrogen). To monitor changes of the cellular metabolic activity, the cell cultures were assayed after 68 hours for metabolic activity using the XTT assay according to the manufacturer's instructions (Roche). The results are shown in the following table:

| | Metabolic activity IC$_{50}$ | |
|---|---|---|
| Oligonucleotides | in D04 cells [$\times 10^{-4}$ nM] | in HT29 cells [$\times 10^{-2}$ nM] |
| 1 | 0.3 | 4 |
| 2 | 0.9 | 3 |
| 3 | 1 | 2 |
| 4 | 0.03 | 0.9 |
| 5 | 0.4 | 2 |
| 6 | 0.07 | 0.3 |
| 7 | 0.3 | 0.6 |
| 8 | 0.6 | 1 |
| 3P-GFP2 1S2F | 1 | |

The IC$_{50}$ of oligonucleotides-5, 6, 7 and 8 is generally lower as compared to oligonucleotides 1, 2, 3 and 4. In D04 cells, the polyribonucleotides designed in accordance with the design rule of the present disclosure show an IC$_{50}$ which is lower than the IC$_{50}$ of the prior art RIG-I agonist 3P-GFP2 1S2F.

Metabolic Activity in Murine Tumor Cells

Murine cell lines CT26 and B16 were seeded at a density of $4\times10^4$ cells per well of a 96-well plate. Chemically synthesized RNA oligonucleotides were purchased from Biomers (Ulm, Germany), Axolabs (Kulmbach, Germany) or were produced internally. RNA was transfected into the cells using Lipofectamine 2000 according to manufacturer's instructions (Invitrogen). To monitor changes of the cellular metabolic activity, the cell cultures were assayed after 68 hours for metabolic activity using the XTT assay according to the manufacturer's instructions (Roche). The results are shown in the following table:

| Oligonucleotides | Metabolic activity IC$_{50}$ | |
|---|---|---|
| | in B16 cells [×10$^{-2}$ nM] | in HT29 cells [×10$^{-2}$ nM] |
| 1 | 0.05 | 0.4 |
| 2 | 0.06 | 0.3 |
| 3 | 0.04 | 0.4 |
| 4 | 0.04 | 0.2 |
| 5 | 0.004 | 0.4 |
| 6 | 0.0008 | 0.2 |
| 7 | 0.007 | 0.3 |
| 8 | 0.0001 | 0.001 |
| 3P-GFP2 1S2F | 7 | 4 |

The IC$_{50}$ of oligonucleotides 5, 6, 7 and 8 is lower as compared to oligonucleotides 1, 2, 3 and 4. The polyribonucleotides designed in accordance with the design rule of the present disclosure show an IC$_{50}$ which is lower than the IC$_{50}$ of the prior art RIG-I agonist 3P-GFP2 1S2F.

Induction of Apoptosis in Human D04 Cells

To monitor apoptosis, human D04 cells were seeded at a density of 3×10$^4$ cells/well into 96 well plates and were treated with agonists as described above. After 48 hours both adherent and floating cells were collected. Cells were washed with cell staining buffer and finally resuspended in Annexin V binding buffer. 2.5 µl/well APC-Annexin V and 2.5 µl/well 7-AAD were added. After 15 min incubation, 100 µl/well Annexin V binding buffer was added and the cells were analyzed using an Attune NxT acoustic focusing cytometer (Life Technologies). The results are shown in the following table:

| Oligonucleotides | Induction of Apoptosis EC$_{50}$ | | |
|---|---|---|---|
| | AV+/AAD− [nM] | AV+ AAD+ [nM] | AV− AAD− [nM] |
| 1 | 0.04 | 0.1 | 0.05 |
| 4 | 0.03 | 0.3 | 0.05 |
| 5 | 0.01 | 0.01 | 0.01 |
| 8 | 0.1 | 0.04 | 0.01 |
| 3P-GFP2 1S2F | 0.06 | 0.2 | 0.05 |

Induction of Apoptosis in Murine Colon 26 Cells

To monitor apoptosis, murine CT26 cells were seeded at a density of 3×10$^4$ cells/well into 96 well plates and were treated with agonists as described above. After 48 hours both adherent and floating cells were collected. Cells were washed with cell staining buffer and finally resuspended in Annexin V binding buffer. 2.5 µl/well APC-Annexin V and 2.5 µl/well 7-AAD were added. After 15 min incubation, 100 µl/well Annexin V binding buffer was added and the cells were analyzed using an Attune NxT acoustic focusing cytometer (Life Technologies). The results are shown in the following table:

| Oligonucleotides | Induction of Apoptosis EC$_{50}$ | |
|---|---|---|
| | AV+/AAD+ [nM] | AV− AAD− [nM] |
| 1 | 0.1 | 0.2 |
| 4 | 0.06 | 0.07 |
| 5 | 0.2 | 0.1 |
| 8 | 0.2 | 0.1 |
| 3P-GFP2 1S2F | 0.2 | 0.2 |

EC$_{50}$ in Human PBMC (IFNα ELISA)

Human primary peripheral blood mononuclear cells (PBMCs) were isolated from fresh buffy coats obtained from healthy volunteers according to standard protocols (Schuberth-Wagner et al., 2015, Immunity). PBMCs (4×10$^5$ cells/well) were seeded in 96-well plates and maintained in RPMI1640 supplemented with 10% FCS, 1.5 mM L-glutamine and 1× penicillin/streptomycin. All cell culture reagents were obtained from Gibco. Chemically synthesized RNA oligonucleotides were purchased from Biomers (Ulm, Germany), Axolabs (Kulmbach, Germany) or were produced internally. RNA was transfected into cells using Lipofectamine 2000 according to manufacturers instructions (Invitrogen). PBMCs were stimulated once and conditioned medium was collected after 17 hrs. Quantitation of IFNα levels in cell culture supernatant was performed using the human IFN alpha matched antibody pairs ELISA (eBioscience, San Diego, Calif., USA). The results are shown in the following table:

| Oligonucleotides | EC$_{50}$ in PBMC IFNα ELISA [nM] |
|---|---|
| 1 | 0.09 |
| 2 | 0.09 |
| 3 | 0.07 |
| 4 | 0.08 |
| 5 | 0.03 |
| 6 | 0.06 |
| 7 | 0.03 |
| 8 | 0.1 |
| 3P-GFP2 1S2F | 0.07 |

5, 6 and 7 show a EC$_{50}$ which is lower than for 1, 2 and 3, and which is lower than for 3P-GFP2 1S2F.

Figure 7:
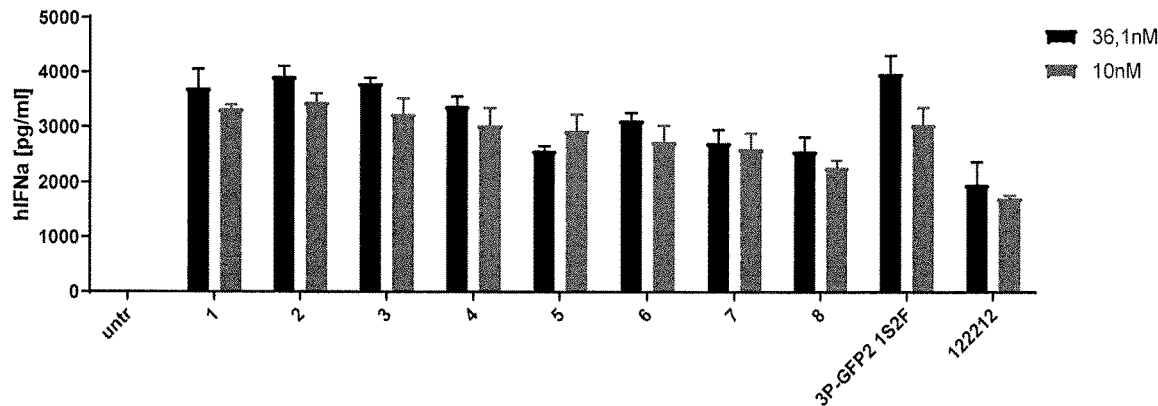
FIG. 7: The polyribonucleotides of Example 4 were tested for RIG-I selectivity. While the tested polyribonucleotides were capable of inducing IFNα (upper panel), no IFNα induction was obtained via TLR7 (middle panel) demonstrating a high selectivity of the tested ribonucleotides for RIG-I. Ribonucleotide 122212 was used as a positive control. The single strands of SEQ ID NO 107-112 and 117-120 did not activate TLR8 (lower panel). Ribonucleotide 122212 has the same sequence as ribonucleotide 121212, but carries a 5'-triphosphate in the sense strand.
Figure 7:
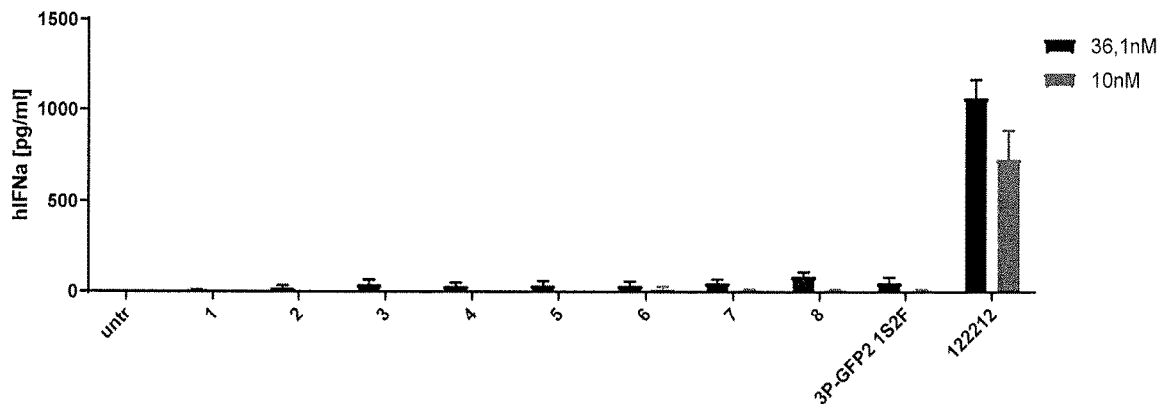
Figure 7:
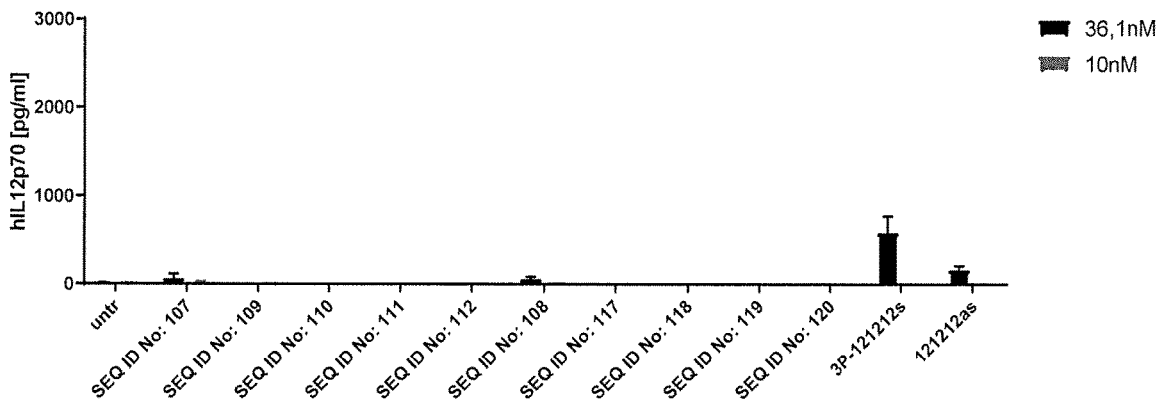

In order to assay the polyribonucleotides for their RIG-I selectivity, RNA was transfected into PBMCs using poly-L-arginine (Sigma Aldrich). RNA and poly-L-arginine were allowed to complex for 0 min and 20 min to trigger TLR7 and TLR8 activation, respectively. Supernatant was pulled after 17 hrs and the cytokine of interest was analyzed. Quantitation of IFNα levels in cell culture supernatant was performed using the human IFN alpha matched antibody pairs ELISA (eBioscience, San Diego, Calif., USA). As an indirect measure of TLR8 activation, IL-12p70 was quantified using the BD kit #555183. As can be seen in FIG. 7, induction of IFNα was specifically triggered via RIG-I but not by TLR 7 or TLR8. Ribonucleotide 122212 was used as a positive control.

LIST OF REFERENCES

WO 2008/017473
WO 2009/060281
WO 2009/141146
WO 2012/039602
WO 2012/130886

WO 2014/049079
Goulet et al., PLoS Pathog. 2013; 9(4):e1003298.
Amparo-Hagmann, PLoS 2013; 8(4): e62872.
Ranoa et al., Oncotarget 2016; 7(18): 26496-26515.
Buers et al., Cyt Grow Fac Rev. 2016; 29: 101-107.
Jang et al., Am J Hum Genet. 2015; 96(2): 266-274.
Martin et al., Leuk Lymphoma 2016; 58: 1686-1693.
Wu et al., Virology 2015; 482: 181-188.
Duewell et al., Cell Death Differ. 2014; 21(12): 1825-1837.
Schlee et al., Immunity 2009; 31: 25-34.
Pichlmair et al., Science 2006; 314: 997-1001.
Schlee, Immunobiology. 2013; 218(11): 1322-1335.
Wang et al., Nat Struct & Mol Biol, 2010; 17(7): 781-787.
Schuberth-Wagner et al., Immunity. 2015; 43(1):41-51.
Devarkar et al., PNAS 2016; 113(3): 596-601.
Louber et al., BMC Biol. 2015; 13: 54.
Ablasser et al., Nat Immunol. 2009; 10(10): 1065-1072.
Xue et al., PLoS One 2015; 10(2): e0115354.
van den Boom and Hartmann, Immunity 2013; 39(1): 27-37.
Han et al., Hepatology 2011; 54(4): 1179-1189.
Ellermeier et al., Cancer Research, 2013; 73(6):1709-1720.
Ebert et al., Gastroenterology, 2011; 141(2): 696-706.
Junt and Barchet, Nat Rev Immunol 2015; 15(9): 529-544.
Poeck et al., Nature Medicine, 2008; 14(11): 1256-1262.
Gold, J Clin Aesthet Dermatol. 2010; 3(12): 37-42.
Ludwig and Eckstein, J. Org. Chem., 1989, 54(3): 631-635.
Brunner et al., Angew Chem Int Ed Engl. 2015; 54(6): 1946-1949.
Kohlway et al., EMBO Rep. 2013; 14(9): 772-779.
Chiang et al., Journal of Virology, 2015; J Virol. 2015; 89(15): 8011-8025.
Schwarz et al., Cell, 2003; 115(2): 199-208.
Goubau et al Nature 2014; 514: 372-375.
Besch et al., Methods Mol Biol. 2014; 1169: 181-192.
Lin et al., J Virol. 2012; 86(19): 10359-10369.
Reikine et al., Front Immunol. 2014; 5: 324.
Pasquale et al. Vaccines 2015; 3: 320-343.

The invention claimed is:

1. A method for producing a RIG-I agonist, comprising the steps of
   (a) preparing a first polyribonucleotide with 21-300 nucleotides in length, which polyribonucleotide starts at the 5' end with a sequence selected from

```
                                              (SEQ ID NO: 12)
   5'-gbucndnwnnnnnnnnwnsnn-3', (SEQ ID NO: 13)
   5'-gucuadnwnnnnnnnnwnsnn-3', (SEQ ID NO: 14)
   5'-guagudnwnnnnnnnnwnsnn-3', (SEQ ID NO: 15)
   5'-gguaadnwnnnnnnnnwnsnn-3', (SEQ ID NO: 16)
   5'-ggcagdnwnnnnnnnnwnsnn-3', (SEQ ID NO: 17)
   5'-gcuucdnwnnnnnnnnwnsnn-3', (SEQ ID NO: 18)
   5'-gcccadnwnnnnnnnnwnsnn-3',
   and
                                              (SEQ ID NO: 19)
   5'-gcgcudnwnnnnnnnnwnsnn-3';
   ```

(b) preparing a second polyribonucleotide with 21-300 nucleotides in length which is at least 80% complementary to the first polyribonucleotide of step (a) over the whole length of the first polyribonucleotide of step (a), and which, when annealed to the first polyribonucleotide of step (a), exhibits either no 3' overhang, or a 3' overhang of 1 or 2 nucleotides; and
   (c) annealing the first polyribonucleotide of step (a) with the second polyribonucleotide of step (b), thereby obtaining a RIG-I agonist;

wherein "b" denotes g, c, or u, "d" denotes a, g, or u, "w" denotes a, or u, "s" denotes g or c, and "n" denotes any nucleotide base.

2. The method of claim 1, wherein in the sequence of the polyribonucleotide of step (a) the ribonucleotide at position 6 is u.

3. The method of claim 1, wherein in the sequence of the polyribonucleotide of step (a) the ribonucleotide at position 7 is g.

4. The method of claim 1, wherein in the sequence of the polyribonucleotide of step (a) the ribonucleotide at position 6 is g, and the ribonucleotide at position 7 is c.

5. The method of claim 1, wherein in the sequence of the polyribonucleotide of step (a) the ribonucleotide at position 8 is a.

6. The method of claim 1, wherein in the sequence of the polyribonucleotide of step (a) the ribonucleotide at position 9 is a.

7. The method of claim 1, wherein in the sequence of the polyribonucleotide of step (a) the ribonucleotide at position 17 is u, and wherein the sequence at the 5'end of the polyribonucleotide in step (a) is selected from

```
                                              (SEQ ID NO: 95)
   5'-gbucndnwnnnnnnnnunsnn-3', (SEQ ID NO: 96)
   5'-gucuadnwnnnnnnnnunsnn-3', (SEQ ID NO: 97)
   5'-guagudnwnnnnnnnnunsnn-3', (SEQ ID NO: 98)
   5'-gguaadnwnnnnnnnnunsnn-3', (SEQ ID NO: 99)
   5'-ggcagdnwnnnnnnnnunsnn-3', (SEQ ID NO: 100)
   5'-gcuucdnwnnnnnnnnunsnn-3', (SEQ ID NO: 101)
   5'-gcccadnwnnnnnnnnunsnn-3',
   and
                                              (SEQ ID NO: 102)
   5'-gcgcudnwnnnnnnnnunsnn-3'.
   ```

8. The method of claim 1, wherein in the sequence of the polyribonucleotide of step (a) the ribonucleotide at position 18 is u.

9. The method of claim 1, wherein in the sequence of the polyribonucleotide of step (a) the ribonucleotide at position 19 is c.

10. The method of claim 1, wherein the sequence at the 5' end of the polyribonucleotide in step (a) is selected from

```
                                              (SEQ ID NO: 20)
   5'-gbucnugaannnnnnnnuucnn-3',
   ```

```
                                                 (SEQ ID NO: 21)
5'-gucuaugaannnnnnnuucnn-3', (SEQ ID NO: 22)
5'-guaguugaannnnnnnuucnn-3', (SEQ ID NO: 23)
5'-gguaaugaannnnnnnuucnn-3', (SEQ ID NO: 24)
5'-ggcagugaannnnnnnuucnn-3', (SEQ ID NO: 25)
5'-gcuucugaannnnnnnuucnn-3', (SEQ ID NO: 26)
5'-gcccaugaannnnnnnuucnn-3', (SEQ ID NO: 27)
5'-gcgcuugaannnnnnnuucnn-3',
and (SEQ ID NO: 66)
5'-gbucnugaaannnnnnuuccnn-3'.
```

11. The method of claim 1, wherein
the polyribonucleotide in step (a) has a length of at most 30 nucleotides, or wherein the complementary polyribonucleotide in step (b) is at least 90% complementary to the first polyribonucleotide of step (a) over the whole length of the first polyribonucleotide of step (a), or
both the polyribonucleotide in step (a) has a length of at most 30 nucleotides and the complementary polyribonucleotide in step (b) is at least 90% complementary to the first polyribonucleotide of step (a) over the whole length of the first polyribonucleotide of step (a).

12. The method of claim 1, wherein the annealed polyribonucleotide of step (c) has two blunt ends, and a length of 24 nucleotides.

13. The method of claim 12, wherein in the polyribonucleotide of step (a) the ribonucleotide sequence at positions 20-24 is selected from 5'-ngavc-3', 5'-uagac-3', 5'-acuac-3', 5'-uuacc-3', 5'-cugcc-3', 5'-gaagc-3', 5'-ugggc-3' and 5'-agcgc-3', wherein "v" denotes a, g or c.

14. The method of claim 12, wherein in the sequence of the polyribonucleotide of step (a) the ribonucleotide at position 6 is g, the ribonucleotide at position 7 is a, and the ribonucleotide at position 8 is a.

15. The method of claim 14, wherein the ribonucleotide at position 9 is a.

16. The method of claim 12, wherein in the sequence of the polyribonucleotide of step (a) the ribonucleotide at position 16 is u.

17. The method of claim 12, wherein in the sequence of the polyribonucleotide of step (a) the ribonucleotide at position 17 is u the ribonucleotide at position 18 is g, and the ribonucleotide at position 19 is c.

18. The method of claim 12, wherein in the sequence of the polyribonucleotide of step (a) the sequence at position 6-24 is selected from

```
                                                 (SEQ ID NO: 3)
5'-ugaannnnnnnuucngavc-3', (SEQ ID NO: 4)
5'-ugaannnnnnnuucngavc-3', (SEQ ID NO: 5)
5'-ugaannnnnnuuucngavc-3', (SEQ ID NO: 6)
```

```
                                                 -continued
5'-gaaannnnnnnuucngavc-3', (SEQ ID NO: 67)
5'-gaaannnnnnnuucngavc-3',
and (SEQ ID NO: 68)
5'-gaaannnnnuuucngavc-3';
or
``` wherein the first RNA sequence of step (a) is selected from

```
                                                 (SEQ ID NO: 7)
5'-gbucnugaannnnnnnuucnnnnn-3', (SEQ ID NO: 8)
5'-gbucnugaannnnnnnuucngavc-3', (SEQ ID NO: 9)
5'-gbucnugaannnnnnnuucngavc-3', (SEQ ID NO: 10)
5'-gbucnugaannnnnnnuucngavc-3', (SEQ ID NO: 11)
5'-gbucngaaannnnnnnuucngavc-3', (SEQ ID NO: 69)
5'-gbucngaaannnnnnnuucngavc-3'
and (SEQ ID NO: 70)
5'-gbucngaaannnnnnuuucngavc-3'.
``` wherein "v" denotes a, g or c.

19. The method of claim 1, wherein the polyribonucleotide prepared in step (a) has a mono-, di-, or triphosphate or respective analogue attached to its 5' end.

20. The method of claim 19, wherein the polyribonucleotide prepared in step (a) has a triphosphate attached to its 5' end.

21. The method of claim 1, wherein the complementary polyribonucleotide prepared in step (b) has a mono-, di-, or triphosphate or respective analogue attached to its 5' end.

22. The method of claim 21, wherein the complementary polyribonucleotide prepared in step (b) has a triphosphate attached to its 5' end.

23. The method of claim 1, wherein the first RNA sequence of step (a) is

```
                                                 (SEQ ID NO: 104)
5'-guucugcaaucagcuauacguuau-3'
or (SEQ ID NO: 103)
5'-guucugcaaucagcuaaacguuau-3'.
```

24. The method of claim 23, wherein the first RNA sequence of step (a) is

```
                                                                    (SEQ ID NO: 108)
3P-5'-g_{PTO}u_{PTO}ucu_{m}gcaa_{f}ucag_{f}cuauacguu_{PTO}a_{PTO}u-3'
or (SEQ ID NO: 107)
3P-5'-g_{PTO}u_{PTO}ucu_{m}gcaa_{f}ucag_{f}cuaaacguu_{PTO}a_{PTO}u-3',
``` the nucleotide indexed m is 2'-O-methylated;
the nucleotide indexed f is 2'-fluoro;
the index PTO between two nucleotides indicates that said two nucleotides are linked by a phosphothioate bond; and
3P-5' is a 5'-triphosphate.

25. The method of claim 23, wherein the second RNA sequence of step (b) is fully complementary to the first RNA sequence of step (a) and is

```
5'-auaacguuuagcugauugcagaac-3';           (SEQ ID NO: 105)
or
5'-aaauaacguuuagcugauugcagaac-3';         (SEQ ID NO: 106)
or
5'-auaacguauagcugauugcagaac-3';           (SEQ ID NO: 115)
or
5'-aaauaacguauagcugauugcagaac-3'.         (SEQ ID NO: 116)
```

26. The method of claim 25, wherein the second RNA sequence of step (b) is

```
5'-a_PTO u_PTO a_m acguu_f uagc_f ugauugcagaac-3'-P,   (SEQ ID NO: 109)
or
5'-a_PTO u_PTO a_m acguu_f uagc_f ugauugcagaac-3',     (SEQ ID NO: 110)
or
5'-aaa_PTO u_PTO a_m acguu_f uagc_f ugauugcagaac-3'-P, (SEQ ID NO: 111)
or
5'-aaa_PTO u_PTO a_m acguu_f uagc_f ugauugcagaac-3',   (SEQ ID NO: 112)
or
5'-a_PTO u_PTO a_m acgua_f uagc_f ugauugcagaac-3'-P,   (SEQ ID NO: 117)
or
5'-a_PTO u_PTO a_m acgua_f uagc_f ugauugcagaac-3',     (SEQ ID NO: 118)
or
5'-aaa_PTO u_PTO a_m acgua_f uagc_f ugauugcagaac-3'-P, (SEQ ID NO: 119)
or
5'-aaa_PTO u_PTO a_m acgua_f uagc_f ugauugcagaac-3';   (SEQ ID NO: 120)
``` wherein the nucleotide indexed m is 2'-O-methylated; the nucleotide indexed f is 2'-fluoro; the index PTO between two nucleotides indicates that said two nucleotides are linked by a phosphothioate bond; and 3'-P is a 3'-monophosphate.

27. The method of claim 1, wherein
(I) the first RNA sequence of step (a) is 3P-5'-g_PTO u_PTO ucu_m gcaa_f ucag_f cuauacguu_PTO a_PTO u-3' (SEQ ID NO: 108) and the second RNA sequence of step (b) is 5'-a_PTO u_PTO a_m acgua_f uagc_f ugauugcagaac-3'-P (SEQ ID NO: 117); or
(II) the first RNA sequence of step (a) is 3P-5'-g_PTO u_PTO ucu_m gcaa_f ucag_f cuauacguu_PTO a_PTO u-3' (SEQ ID NO: 108) and the second RNA sequence of step (b) is 5'-a_PTO u_PTO a_m acgua_f uagc_f ugauugcagaac-3' (SEQ ID NO: 118); or
(III) the first RNA sequence of step (a) is 3P-5'-g_PTO u_PTO ucu_m gcaa_f ucag_f cuauacguu_PTO a_PTO u-3' (SEQ ID NO: 108) and the second RNA sequence of step (b) is 5'-aaa_PTO u_PTO a_m acgua_f uagc_f ugauugcagaac-3'-P (SEQ ID NO: 119); or
(IV) the first RNA sequence of step (a) is 3P-5'-g_PTO u_PTO ucu_m gcaa_f ucag_f cuauacguu_PTO a_PTO u-3' (SEQ ID NO: 108) and the second RNA sequence of step (b) is 5'-aaa_PTO u_PTO a_m acgua_f uagc_f ugauugcagaac-3' (SEQ ID NO: 120); or
(V) the first RNA sequence of step (a) is 3P-5'-g_PTO u_PTO ucu_m gcaa_f ucag_f cuauacguu_PTO a_PTO u-3' (SEQ ID NO: 107) and the second RNA sequence of step (b) is 5'-a_PTO u_PTO a_m acguu_f uagc_f ugauugcagaac-3'-P (SEQ ID NO: 109); or
(VI) the first RNA sequence of step (a) is 3P-5'-g_PTO u_PTO ucu_m gcaa_f ucag_f cuaaacguu_PTO a_PTO u-3' (SEQ ID NO: 107) and the second RNA sequence of step (b) is 5'-a_PTO u_PTO a_m acguu_f uagc_f ugauugcagaac-3' (SEQ ID NO: 110); or
(VII) the first RNA sequence of step (a) is 3P-5'-g_PTO u_PTO ucu_m gcaa_f ucag_f cuaaacguu_PTO a_PTO u-3' (SEQ ID NO: 107) and the second RNA sequence of step (b) is 5'-aaa_PTO u_PTO a_m acgcuu_f uagc_f ugauugcagaac-3'-P (SEQ ID NO: 111); or
(VIII) the first RNA sequence of step (a) is 3P-5'-g_PTO u_PTO ucu_m gcaa_f ucag_f cuaaacguu_PTO a_PTO u-3' (SEQ ID NO: 107) and the second RNA sequence of step (b) is 5'-aaa_PTO u_PTO a_m acguu_f uagc_f ugauugcagaac-3' (SEQ ID NO: 112).

28. A RIG-I agonist, obtainable by the method of claim 1; wherein the first RNA sequence is

```
5'-guucugcaaucagcuauacguuau-3'            (SEQ ID NO: 104)
or
5'-guucugcaaucagcuaaacguuau-3'.           (SEQ ID NO: 103)
```

29. The RIG-I agonist of claim 28, wherein the RIG-I agonist is a polyribonucleotide which comprises at least one synthetic or modified internucleoside linkage, selected from phosphodiester, phosphorothioate, N3 phosphoramidate, boranophosphate, 2,5-phosphodiester, amide-linked, phosphonoacetate (PACE), morpholino, peptide nucleic acid (PNA), or a mixture thereof, provided the linkage(s) do not compromise the type I IFN-inducing activity of the polyribonucleotide.

30. The RIG-I agonist of claim 29, wherein the polyribonucleotide comprises phosphorothioate linkage(s), pyrophosphate linkage(s), or both.

31. The RIG-I agonist of claim 28, wherein the RIG-I agonist is a polyribonucleotide which comprises at least one modified nucleotide selected from pseudouridine, 2-thiouridine, 2'-fluorine-dNTP, 2'-O-methylated NTP.

32. The RIG-I agonist of claim 28, wherein the first RNA sequence is
3P-5'-g_PTO u_PTO ucu_m gcaa_f ucag_f cuauacguu_PTO a_PTO u-3' (SEQ ID NO: 108) or
3P-5'-g_PTO u_PTO ucu_m gcaa_f ucag_f cuaaacguu_PTO a_PTO u-3' (SEQ ID NO: 107), wherein
the nucleotide indexed m is 2'-O-methylated;
the nucleotide indexed f is 2'-fluoro;
the index PTO between two nucleotides indicates that said two nucleotides are linked by a phosphothioate bond; and
3P-5' is a 5'-triphosphate.

33. The RIG-I agonist of claim 28, wherein the second RNA sequence is fully complementary to the first RNA sequence and is

```
                                      (SEQ ID NO: 105)
  5'-auaacguuuagcugauugcagaac-3';
  or (SEQ ID NO: 106)
  5'-aaauaacguuuagcugauugcagaac-3';
  or (SEQ ID NO: 115)
  5'-auaacguauagcugauugcagaac-3';
  or (SEQ ID NO: 116)
  5'-aaauaacguauagcugauugcagaac-3'.
```

34. The RIG-I agonist of claim 33, wherein the second RNA sequence is

```
                                      (SEQ ID NO: 109)
  5'-a_PTO u_PTO a_m acguu_f uagc_f ugauugcagaac-3'-P,
  or (SEQ ID NO: 110)
  5'-a_PTO u_PTO a_m acguu_f uagc_f ugauugcagaac-3',
  or (SEQ ID NO: 111)
  5'-aaa_PTO u_PTO a_m acguu_f uagc_f ugauugcagaac-3'-P,
  or (SEQ ID NO: 112)
  5'-aaa_PTO u_PTO a_m acguu_f uagc_f ugauugcagaac-3',
  or (SEQ ID NO: 117)
  5'-a_PTO u_PTO a_m acgua_f uagc_f ugauugcagaac-3'-P,
  or (SEQ ID NO: 118)
  5'-a_PTO u_PTO a_m acgua_f uagc_f ugauugcagaac-3',
  or (SEQ ID NO: 119)
  5'-aaa_PTO u_PTO a_m acgua_f uagc_f ugauugcagaac-3'-P,
  or (SEQ ID NO: 120)
  5'-aaa_PTO u_PTO a_m acgua_f uagc_f ugauugcagaac-3';
``` wherein the nucleotide indexed m is 2'-O-methylated;
the nucleotide indexed f is 2'-fluoro;
the index PTO between two nucleotides indicates that said two nucleotides are linked by a phosphothioate bond; and
3'-P is a 3'-monophosphate.

35. The RIG-I agonist of claim 33, wherein
(I) the first RNA sequence is 3P-5'-$g_{PTO}u_{PTO}$ucu$_m$gcaa$_f$ucag$_f$cuauacguu$_{PTO}a_{PTO}$u-3' (SEQ ID NO: 108) and the second RNA sequence is 5'-$a_{PTO}u_{PTO}a_m$acgua$_f$uagc$_f$u-gauugcagaac-3'-P (SEQ ID NO: 117); or
(II) the first RNA sequence is 3P-5'-$g_{PTO}u_{PTO}$ucu$_m$gcaa$_f$ucag$_f$cuauacguu$_{PTO}a_{PTO}$u-3' (SEQ ID NO: 108) and the second RNA sequence is 5'-$a_{PTO}u_{PTO}a_m$acgua$_f$uagc$_f$u-gauugcagaac-3' (SEQ ID NO: 118); or
(III) the first RNA sequence is 3P-5'-$g_{PTO}u_{PTO}$ucu$_m$gcaa$_f$ucag$_f$cuauacguu$_{PTO}a_{PTO}$u-3' (SEQ ID NO: 108) and the second RNA sequence is 5'-aaa$_{PTO}u_{PTO}a_m$acgua$_f$uagc$_f$ugauugcagaac-3'-P (SEQ ID NO: 119); or
(IV) the first RNA sequence is 3P-5'-$g_{PTO}u_{PTO}$ucu$_m$gcaa$_f$ucag$_f$cuauacguu$_{PTO}a_{PTO}$u-3' (SEQ ID NO: 108) and the second RNA sequence is 5'-aaa$_{PTO}u_{PTO}a_m$acgua$_f$uagc$_f$ugauugcagaac-3' (SEQ ID NO: 120); or
(V) the first RNA sequence is 3P-5'-$g_{PTO}u_{PTO}$ucu$_m$gcaa$_f$ucag$_f$cuaaacguu$_{PTO}a_{PTO}$u-3' (SEQ ID NO: 107) and the second RNA sequence is 5'-$a_{PTO}u_{PTO}a_m$acguu$_f$uagc$_f$u-gauugcagaac-3'-P (SEQ ID NO: 109); or
(VI) the first RNA sequence is 3P-5'-$g_{PTO}u_{PTO}$ucu$_m$gcaa$_f$ucag$_f$cuaaacguu$_{PTO}a_{PTO}$u-3' (SEQ ID NO: 107) and the second RNA sequence is 5'-$a_{PTO}u_{PTO}a_m$acguu$_f$uagc$_f$u-gauugcagaac-3' (SEQ ID NO: 110); or
(VII) the first RNA sequence is 3P-5'-$g_{PTO}u_{PTO}$ucu$_m$gcaa$_f$ucag$_f$cuaaacguu$_{PTO}a_{PTO}$u-3' (SEQ ID NO: 107) and the second RNA sequence is 5'-aaa$_{PTO}u_{PTO}a_m$acguu$_f$uagc$_f$ugauugcagaac-3'-P (SEQ ID NO: 111); or
(VIII) the first RNA sequence is 3P-5'-$g_{PTO}u_{PTO}$ucu$_m$gcaa$_f$ucag$_f$cuaaacguu$_{PTO}a_{PTO}$u-3' (SEQ ID NO: 107) and the second RNA sequence is 5'-aaa$_{PTO}u_{PTO}a_m$acguu$_f$uagc$_f$ugauugcagaac-3' (SEQ ID NO: 112).

36. A RIG-I agonist, wherein
(I) the first RNA sequence is 3P-5'-$g_{PTO}u_{PTO}$ucu$_m$gcaa$_f$ucag$_f$cuauacguu$_{PTO}a_{PTO}$u-3' (SEQ ID NO: 108) and the second RNA sequence is 5'-$a_{PTO}u_{PTO}a_m$acgua$_f$uagc$_f$u-gauugcagaac-3'-P (SEQ ID NO: 117); or
(II) the first RNA sequence is 3P-5'-$g_{PTO}u_{PTO}$ucu$_m$gcaa$_f$ucag$_f$cuauacguu$_{PTO}a_{PTO}$u-3' (SEQ ID NO: 108) and the second RNA sequence is 5'-$a_{PTO}u_{PTO}a_m$acgua$_f$uagc$_f$u-gauugcagaac-3' (SEQ ID NO: 118); or
(III) the first RNA sequence is 3P-5'-$g_{PTO}u_{PTO}$ucu$_m$gcaa$_f$ucag$_f$cuauacguu$_{PTO}a_{PTO}$u-3' (SEQ ID NO: 108) and the second RNA sequence is 5'-aaa$_{PTO}u_{PTO}a_m$acgua$_f$uagc$_f$ugauugcagaac-3'-P (SEQ ID NO: 119); or
(IV) the first RNA sequence is 3P-5'-$g_{PTO}u_{PTO}$ucu$_m$gcaa$_f$ucag$_f$cuauacguu$_{PTO}a_{PTO}$u-3' (SEQ ID NO: 108) and the second RNA sequence is 5'-aaa$_{PTO}u_{PTO}a_m$acgua$_f$uagc$_f$ugauugcagaac-3' (SEQ ID NO: 120); or
(V) the first RNA sequence is 3P-5'-$g_{PTO}u_{PTO}$ucu$_m$gcaa$_f$ucag$_f$cuaaacguu$_{PTO}a_{PTO}$u-3' (SEQ ID NO: 107) and the second RNA sequence is 5'-$a_{PTO}u_{PTO}a_m$acguu$_f$uagc$_f$u-gauugcagaac-3'-P (SEQ ID NO: 109); or
(VI) the first RNA sequence is 3P-5'-$g_{PTO}u_{PTO}$ucu$_m$gcaa$_f$ucag$_f$cuaaacguu$_{PTO}a_{PTO}$u-3' (SEQ ID NO: 107) and the second RNA sequence is 5'-$a_{PTO}u_{PTO}a_m$acguu$_f$uagc$_f$u-gauugcagaac-3' (SEQ ID NO: 110); or
(VII) the first RNA sequence is 3P-5'-$g_{PTO}u_{PTO}$ucu$_m$gcaa$_f$ucag$_f$cuaaacguu$_{PTO}a_{PTO}$u-3' (SEQ ID NO: 107) and the second RNA sequence is 5'-aaa$_{PTO}u_{PTO}a_m$acguu$_f$uagc$_f$ugauugcagaac-3'-P (SEQ ID NO: 111); or
(VIII) the first RNA sequence is 3P-5'-$g_{PTO}u_{PTO}$ucu$_m$gcaa$_f$ucag$_f$cuaaacguu$_{PTO}a_{PTO}$u-3' (SEQ ID NO: 107) and the second RNA sequence is 5'-aaa$_{PTO}u_{PTO}a_m$acguu$_f$uagc$_f$ugauugcagaac-3' (SEQ ID NO: 112).

37. A new pharmaceutical composition comprising at least one RIG-I agonist of claim 28, and a pharmaceutically acceptable carrier.

38. The pharmaceutical composition of claim 37, further comprising at least one agent selected from an anti-tumor agent, an immunostimulatory agent, an anti-viral agent, an anti-bacterial agent, a checkpoint-inhibitor, retinoic acid, IFN-α, and IFN-β.

39. The pharmaceutical composition of claim 37, wherein said composition is a vaccine composition.

40. A vaccine adjuvant, comprising a pharmaceutical composition according to claim 37.

41. An ex vivo method for inducing type I IFN production in a cell, comprising the step of contacting a cell expressing RIG-I with at least one RIG-I agonist according to claim 28.

42. A pharmaceutical composition comprising at least one RIG-I agonist of claim 36, and a pharmaceutically acceptable carrier.

43. An ex vivo method for inducing type I IFN production in a cell, comprising the step of contacting a cell expressing RIG-I with at least one RIG-I agonist according to claim 36.

\* \* \* \* \*